United States Patent
Zhang et al.

(10) Patent No.: US 11,286,248 B2
(45) Date of Patent: Mar. 29, 2022

(54) PYRAZINE-2(1H)-KETONE COMPOUND ACTING AS FGFR INHIBITOR

(71) Applicant: ZHANGZHOU PIEN TZE HUANG PHARMACEUTICAL CO., LTD., Fujian (CN)

(72) Inventors: Yang Zhang, Shanghai (CN); Zhifei Fu, Shanghai (CN); Miaorong Luo, Shanghai (CN); Zaifang Ren, Shanghai (CN); Dongjie Hu, Shanghai (CN); Jie Li, Shanghai (CN); Jian Li, Shanghai (CN); Shuhui Chen, Shanghai (CN)

(73) Assignee: ZHANGZHOU PIEN TZE HUANG PHARMACEUTICAL CO., LTD., Zhangzhou (CN)

( * ) Notice: Subject to any disclaimer, the term of this patent is extended or adjusted under 35 U.S.C. 154(b) by 68 days.

(21) Appl. No.: 16/968,546

(22) PCT Filed: Feb. 2, 2019

(86) PCT No.: PCT/CN2019/074576
§ 371 (c)(1),
(2) Date: Aug. 7, 2020

(87) PCT Pub. No.: WO2019/154364
PCT Pub. Date: Aug. 15, 2019

(65) Prior Publication Data
US 2021/0040070 A1      Feb. 11, 2021

(30) Foreign Application Priority Data
Feb. 8, 2018   (CN) .................... 201810130631.3

(51) Int. Cl.
| C07D 401/14 | (2006.01) |
| C07D 403/14 | (2006.01) |
| C07D 471/04 | (2006.01) |

(52) U.S. Cl.
CPC ......... C07D 403/14 (2013.01); C07D 401/14 (2013.01); C07D 471/04 (2013.01)

(58) Field of Classification Search
CPC .. C07D 401/14; C07D 403/14; C07D 413/14; C07D 471/04
See application file for complete search history.

(56) References Cited

U.S. PATENT DOCUMENTS

2006/0293339 A1   12/2006   Chakravarty et al.

FOREIGN PATENT DOCUMENTS

| CN | 101468965 A | 7/2009 |
| CN | 104540809 A | 4/2015 |
| CN | 107438607 A | 12/2017 |
| WO | WO-2007/058392 A1 | 5/2007 |
| WO | WO-2013/061081 A1 | 5/2013 |
| WO | 2014/011900 A2 | 1/2014 |
| WO | 2016/134320 A1 | 8/2016 |
| WO | WO-2017/070708 A1 | 4/2017 |

OTHER PUBLICATIONS

Extended European Search Report dated Sep. 29, 2021 issued in corresponding EP Application No. 19750681.9, 5 pages.
First Office Action dated Jul. 28, 2021 issued in corresponding CN Application No. 201980012023.5, with English translation, 6 pages.
International Search Report dated Apr. 28, 2019 issued in International Patent Application No. PCT/CN2019/074576, 7 pages.
Written Opinion of the International Searching Authority dated Apr. 28, 2019 issued in International Patent Application No. PCT/CN2019/074576, 8 pages.
Notice of Reasons for Refusal dated Nov. 2, 2021 issued in counterpart JP Application No. 2020-542948, with English translation, 3 pages.

Primary Examiner — Brian E McDowell
(74) Attorney, Agent, or Firm — Foley & Lardner LLP

(57) ABSTRACT

Disclosed are a compound as shown in formula (I), and an isomer thereof or a pharmaceutically acceptable salt thereof, and involved is the use thereof in the preparation of drugs for treating FGFR-associated diseases.

(I)

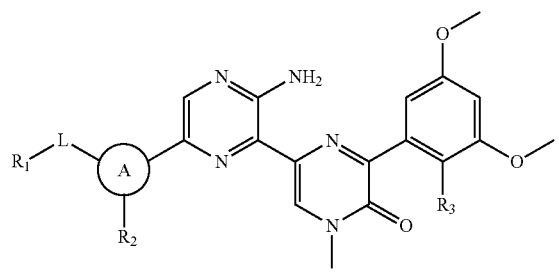

18 Claims, No Drawings

PYRAZINE-2(1H)-KETONE COMPOUND ACTING AS FGFR INHIBITOR

REFERENCE TO RELATED APPLICATION

The present application claims the following right of priority:

The present application is a 371 of PCT/CN2019/074576, filed on Feb. 2, 2019, which claims the right of priority to Chinese patent application CN 201810130631.3, filed on Feb. 8, 2018, the contents of which are incorporated herein by reference in their entireties.

TECHNICAL FIELD

The present invention relates to a compound as shown in formula (I), an isomer thereof or a pharmaceutically acceptable salt thereof, and relates to the use thereof in the manufacture of a medicament for treating FGFR-associated diseases.

BACKGROUND ART

Fibroblast growth factor receptor (FGFR) is a receptor for fibroblast growth factor (FGF) signaling, which is a family consisting of four members, FGFR1, FGFR2, FGFR3 and FGFR4, and is a glycoprotein composed of an extracellular immunoglobulin (Ig)-like domain, a hydrophobic transmembrane region, and an intracellular part containing a tyrosine kinase region. Fibroblast growth factor (FGF) plays an important role in many physiological adjustment processes such as cell proliferation, cell differentiation, cell migration, and angiogenesis through these receptors (FGFRs). There is a lot of evidences showing that the abnormality of FGF signaling pathway (high expression, gene amplification, gene mutation, chromosomal recombination, etc.) are directly correlated with many pathological processes such as tumor cell proliferation, migration, invasion and angiogenesis. Therefore, FGFR has become an important therapeutic target, and attracts a wide range of interests of research and development.

SUMMARY OF THE INVENTION

The present invention provides a compound as shown in formula (I), an isomer thereof or a pharmaceutically acceptable salt thereof, wherein

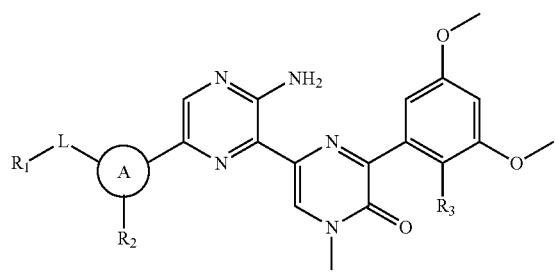

(I)

L is selected from a single bond, —CH$_2$—, —CH$_2$CH$_2$— and —NHC(=O)—;

R$_1$ is selected from H, C$_{1-6}$ alkyl, C$_{3-6}$ cycloalkyl and 5- to 6-membered heterocycloalkyl, wherein the C$_{1-6}$ alkyl, C$_{3-6}$ cycloalkyl and 5- to 6-membered heterocycloalkyl are optionally substituted with 1, 2 or 3 R$_a$;

R$_a$ is each independently selected from F, Cl, Br, I, OH, NH$_2$, CN, C$_{1-3}$ alkyl and C$_{1-3}$ heteroalkyl, wherein the C$_{1-3}$ alkyl and C$_{1-3}$ heteroalkyl are optionally substituted with 1, 2, or 3 R;

R is each independently selected from F, Cl, Br, I, OH, NH$_2$, CN, Me, CF$_3$ and

;

R$_2$ is selected from F, Cl, Br, I, OH, NH$_2$, CN, C$_{1-3}$ alkyl and C$_{1-3}$ heteroalkyl;

or R$_1$ and R$_2$ are connected together to form a 5- to 6-membered ring, wherein the 5- to 6-membered ring is optionally substituted with 1, 2 or 3 R;

R$_3$ is selected from H, F, Cl, Br, I, OH and NH$_2$;

ring A is selected from 5- to 6-membered heteroaryl; and the C$_{1-3}$ heteroalkyl, 5- to 6-membered heterocycloalkyl, 5- to 6-membered heteroaryl respectively comprise 1, 2 or 3 heteroatoms or heteroatomic groups independently selected from —O—, —NH—, —S— and N.

In some embodiments of the present invention, the above R$_a$ is each independently selected from F, Cl, Br, I, OH, NH$_2$, CN, C$_{1-3}$ alkyl and C$_{1-3}$ alkoxy, wherein the C$_{1-3}$ alkyl and C$_{1-3}$ alkoxy are optionally substituted with 1, 2, or 3 R, and other variables are as defined in the present invention.

In some embodiments of the present invention, the above R$_a$ is each independently selected from F, Cl, Br, I, OH NH$_2$, CN, Me, Et and

, wherein the Me, Et and

are optionally substituted with 1, 2, or 3 R, and other variables are as defined in the present invention.

In some embodiments of the present invention, the above R$_a$ is each independently selected from F, Cl, Br, I, OH, NH$_2$, CN, Me, CF$_3$,

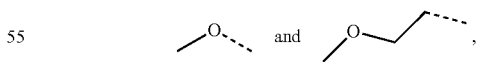

other variables are as defined in the present invention.

In some embodiments of the present invention, the above R$_1$ is selected from H, C$_{1-3}$ alkyl, C$_{3-6}$ cycloalkyl, piperidinyl and morpholinyl, wherein the C$_{1-3}$ alkyl, C$_{3-6}$ cycloalkyl, azetidinyl, piperidinyl and morpholinyl are optionally substituted with 1, 2 or 3 R$_a$, and other variables are as defined in the present invention.

In some embodiments of the present invention, the above R$_1$ is selected from H, Me,

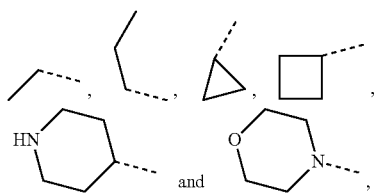

wherein the Me,

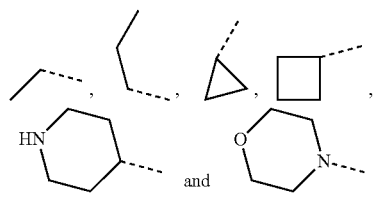

are optionally substituted with 1, 2, or 3 $R_a$, and other variables are as defined in the present invention.

In some embodiments of the present invention, the above $R_1$ is selected from H, Me,

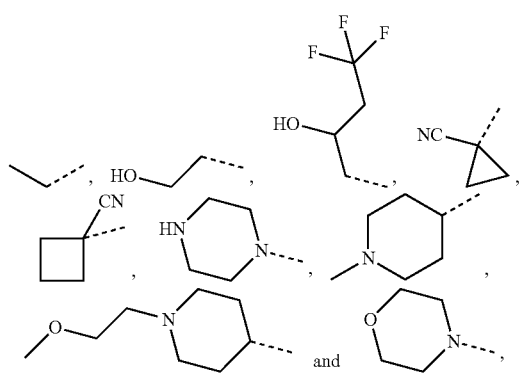

and other variables are as defined in the present invention.

In some embodiments of the present invention, the above $R_2$ is selected from H and Me, and other variables are as defined in the present invention.

In some embodiments of the present invention, the above structural unit $R_1$-L- is

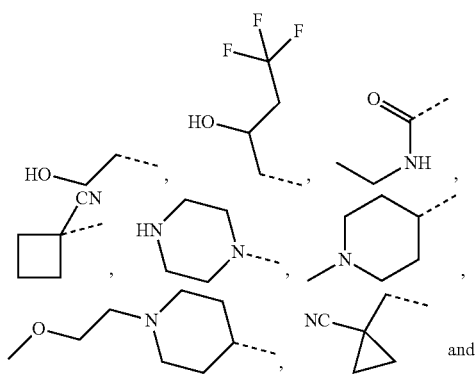

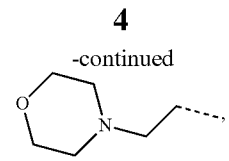

and other variables are as defined in the present invention.

In some embodiments of the present invention, the above ring A is selected from pyrazolyl, imidazolyl and pyridyl, and other variables are as defined in the present invention.

In some embodiments of the present invention, the above structural unit

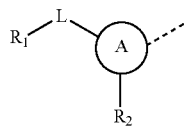

is selected from

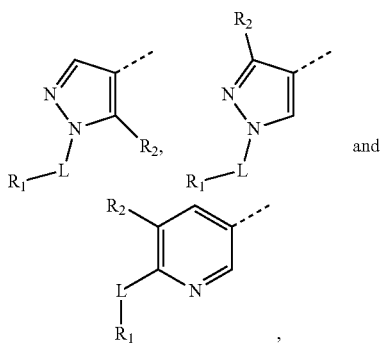

and other variables are as defined in the present invention.

In some embodiments of the present invention, the above $R_1$ and $R_2$ are connected together to form pyrrolidin-2-one, wherein the pyrrolidin-2-one is optionally substituted with 1, 2, or 3 R, and other variables are as defined in the present invention.

In some embodiments of the resent invention, the above $R_1$ and $R_2$ are connected together, the structural unit

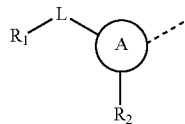

is selected from

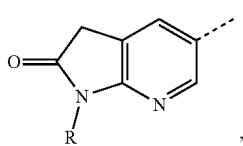

and other variables are as defined in the present invention.

In some embodiments of the resent invention the above structural unit is selected from

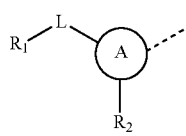

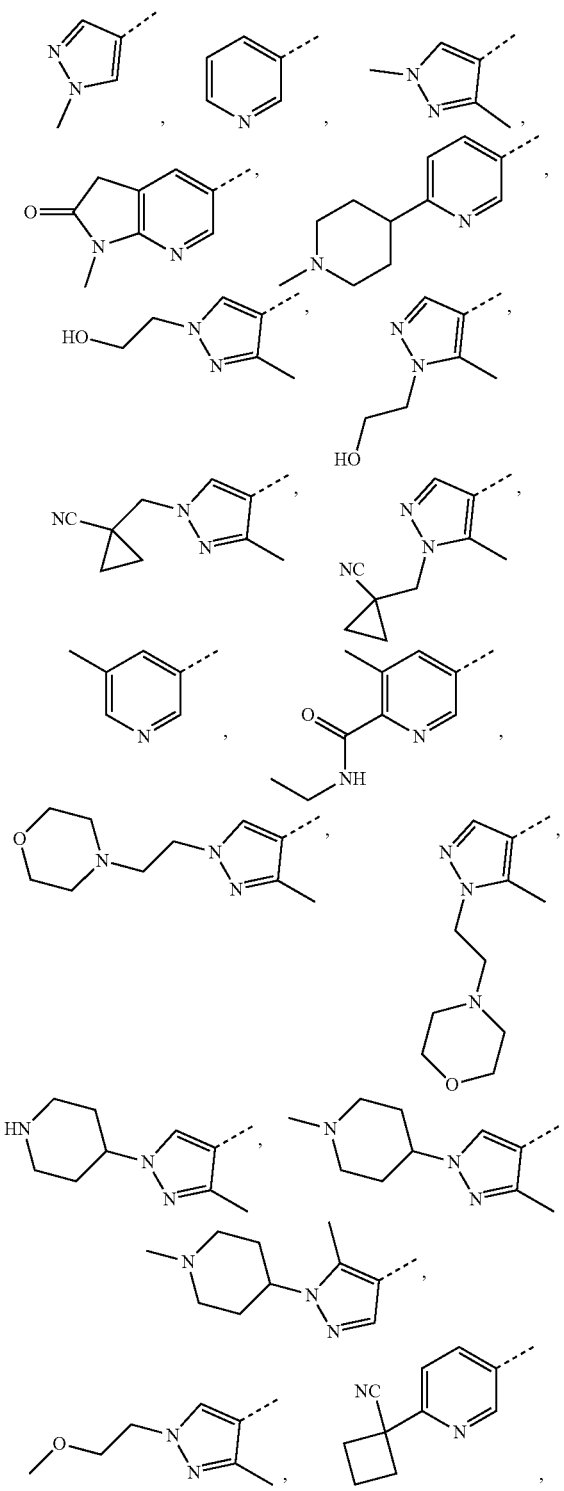

-continued

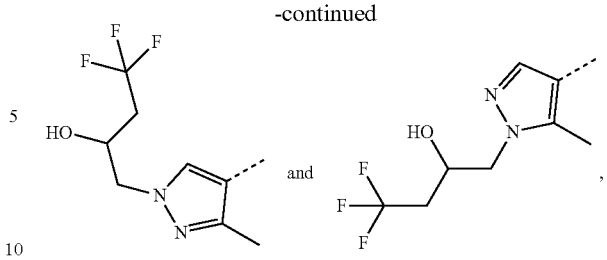

and other variables are as defined in the present invention.

In some embodiments of the present invention, the above compound, isomer thereof or pharmaceutically acceptable salt thereof is selected from

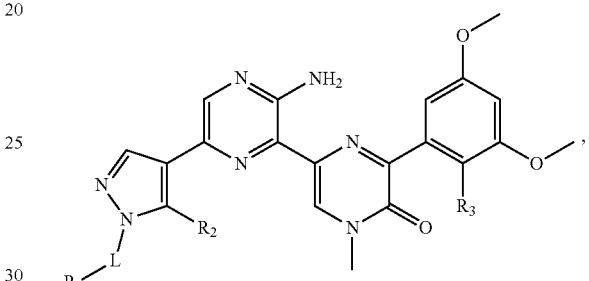

(I-1)

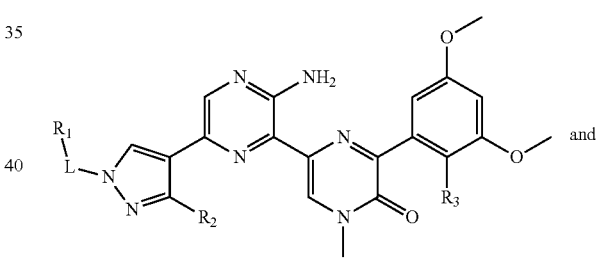

(I-2)

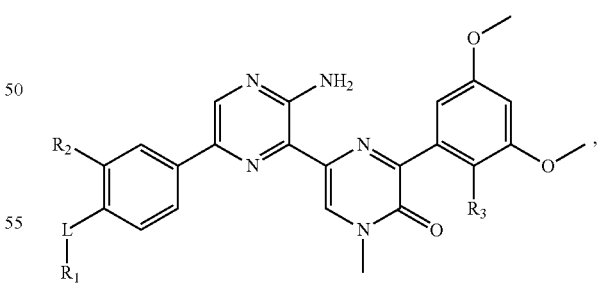

(I-4)

wherein $R_1$, $R_2$, $R_3$ and L are as defined in the present invention.

There are still some embodiments of the present invention derived from any combination of the above variables.

The present invention also provides a compound as shown in the following formulas, an isomer thereof or a pharmaceutically acceptable salt thereof:

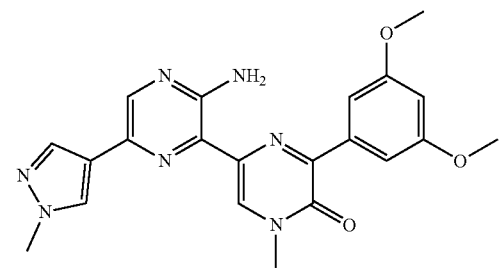
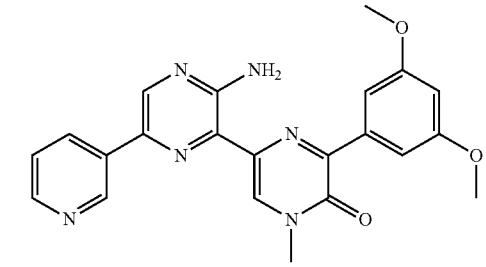
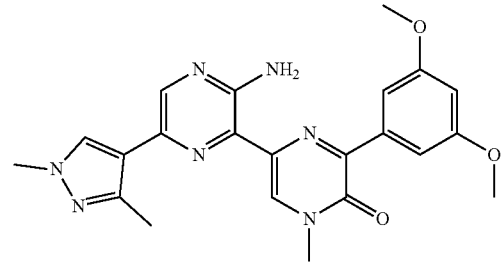
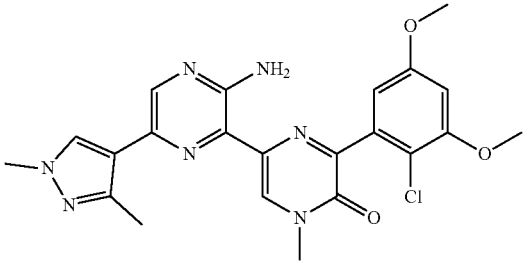
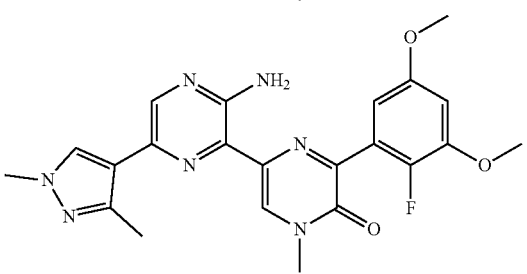
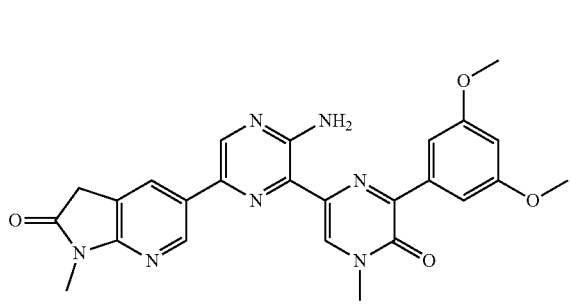
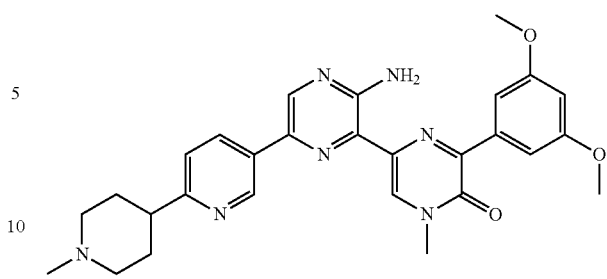
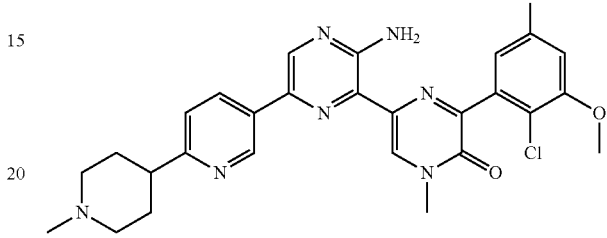
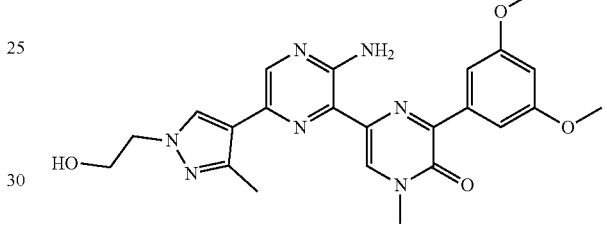
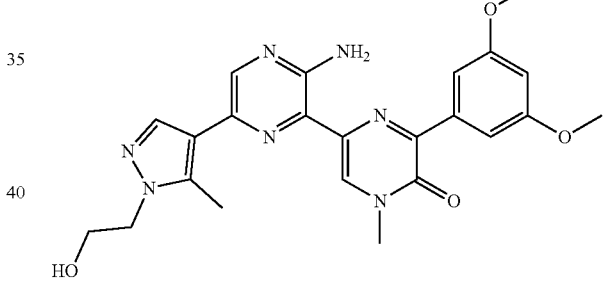
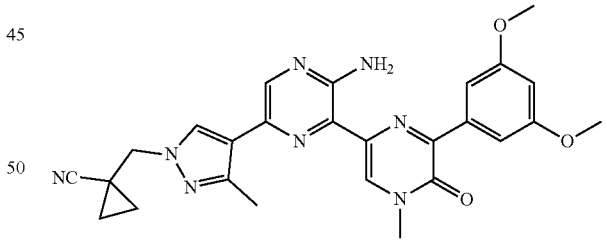
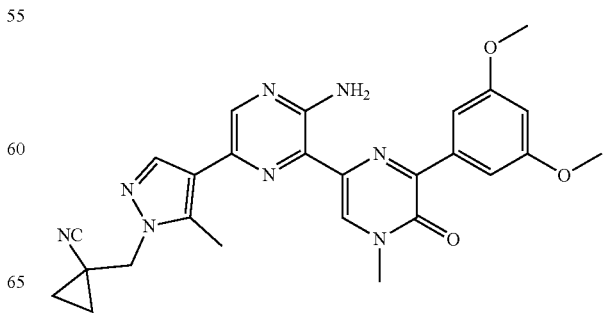

-continued
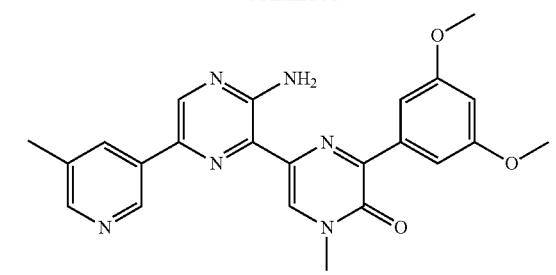
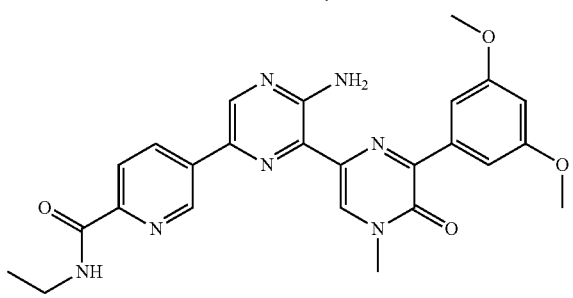
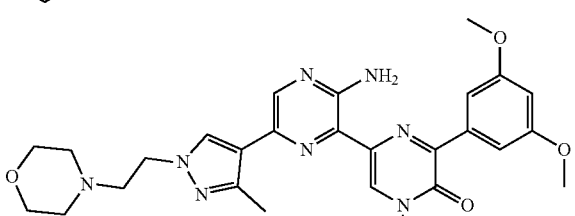
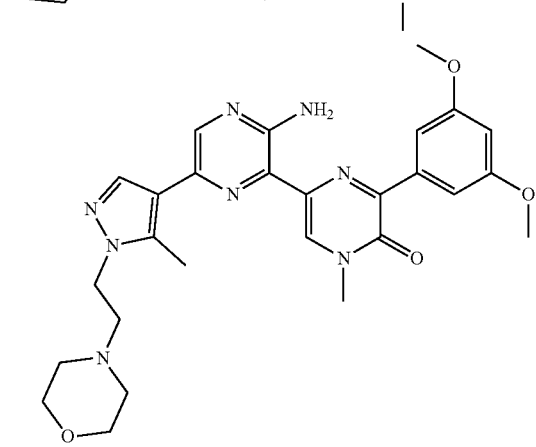
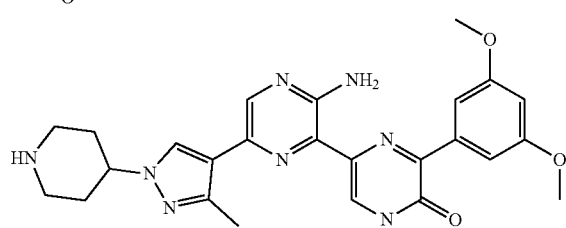
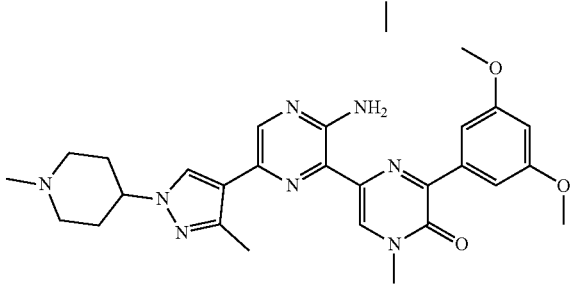
-continued
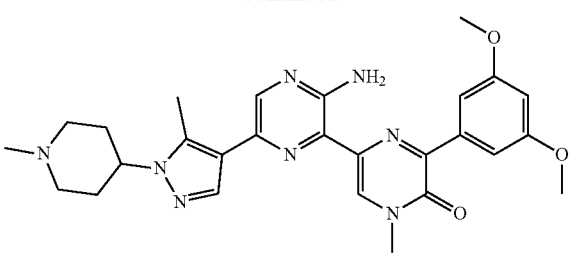
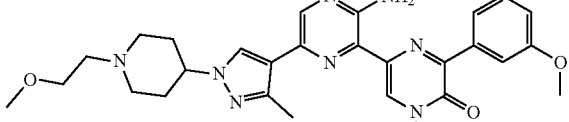
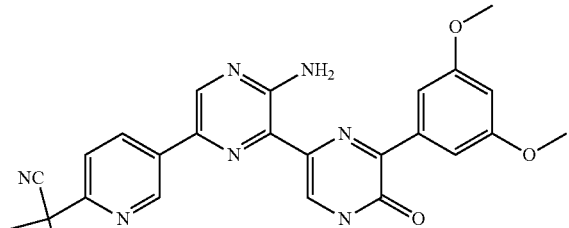
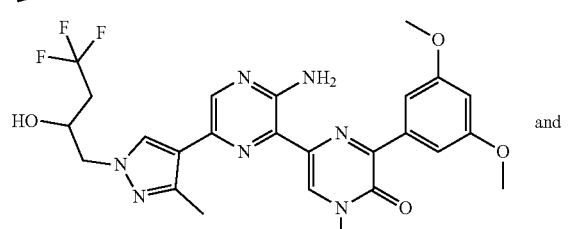
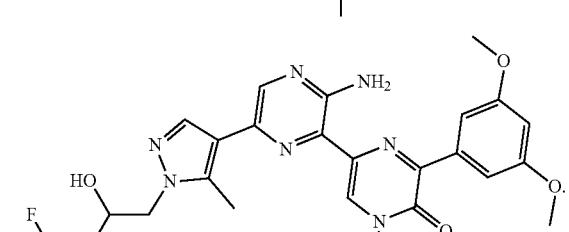
and
In some embodiments of the present invention, the above compound, isomer thereof or pharmaceutically acceptable salt thereof is selected from
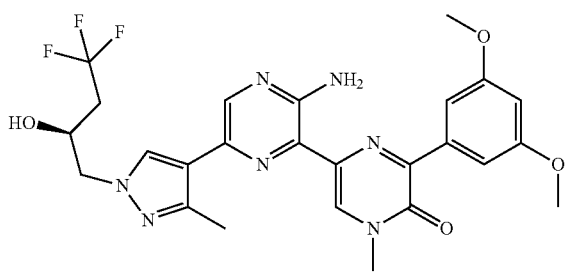

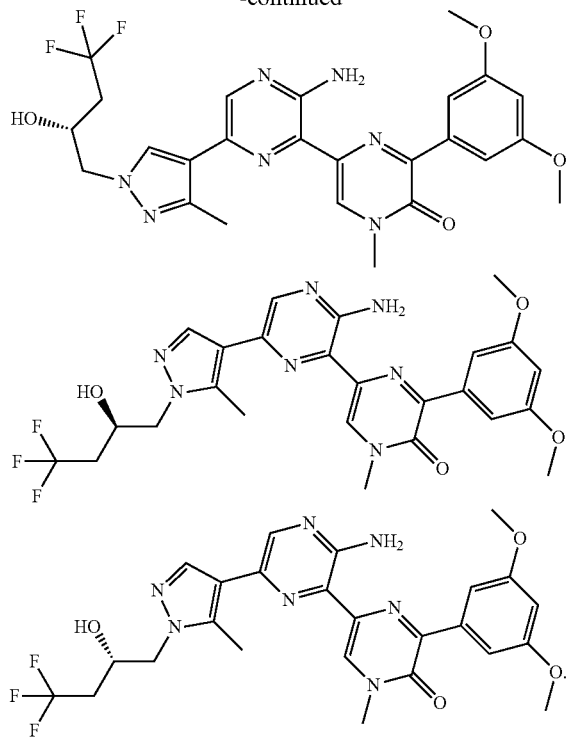

The present invention also relates to use of the above compound, isomer thereof or pharmaceutically acceptable salt thereof in the manufacture of a medicament for treating FGFR-associated diseases.

Technical Effects

The compounds of the present invention exhibit very high inhibitory activity against wild-type FGFR, and show a significantly better inhibitory activity and a higher selectivity on FGFR2 and FGFR3 than on FGFR1 and FGFR4.

Definition and Description

Unless otherwise stated, the following terms and phrases used herein are intended to have the following meanings. A specific term or phrase should not be considered uncertain or unclear unless specifically defined, but should be understood in its ordinary meaning. When a trade name appears herein, it is intended to refer to its corresponding trade product or its active ingredient. The term "pharmaceutically acceptable" as used herein refers to those compounds, materials, compositions and/or dosage forms, which are, within the scope of sound medical judgment, suitable for use in contact with human and animal tissues, without excessive toxicity, irritation, allergic reactions or other problems or complications, which is commensurate with a reasonable benefit/risk ratio.

The term "pharmaceutically acceptable salt" refers to a salt of the compound of the present invention, which is prepared from the compound having specific substituents found in the present invention with relatively non-toxic acids or bases. When compounds of the present invention contain relatively acidic functional groups, base addition salts can be obtained by contacting the neutral form of such compounds with a sufficient amount of base, either in pure solution or a suitable inert solvent. Pharmaceutically acceptable base addition salts include sodium, potassium, calcium, ammonium, organic amine or magnesium salts or similar salts. When compounds of the present invention contain relatively basic functional groups, acid addition salts can be obtained by contacting the neutral form of such compounds with a sufficient amount of acid, either in pure solution or a suitable inert solvent. Examples of pharmaceutically acceptable acid addition salts include salts of inorganic acids, which include, for example, hydrochloric acid, hydrobromic acid, nitric acid, carbonic acid, bicarbonate, phosphoric acid, monohydrogen phosphate, dihydrogen phosphate, sulfuric acid, hydrogen sulfate, hydroiodic acid and phosphorous acid; and salts of organic acids, which include, for example, acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, and methanesulfonic acid; and also include salts of amino acids (such as arginine), and salts of organic acids such as glucuronic acid. Certain compounds of the present invention contain both basic and acidic functional groups so that they can be converted to any of the base or acid addition salts.

The pharmaceutically acceptable salts of the present invention can be synthesized from a parent compound containing acid radicals or bases by means of conventional chemical methods. In general, the method for preparing such salts comprises: in water or an organic solvent or a mixture of both, reacting these compounds in free acid or base forms with a stoichiometric amount of a suitable base or acid to prepare the salts.

In addition to salt forms, the compounds provided by the invention also exist in prodrug forms. The prodrugs of the compounds described herein readily undergo chemical changes under physiological conditions to be converted to the compounds of the present invention. In addition, prodrugs can be converted to the compounds of the invention by chemical or biochemical methods in the in vivo environment.

Certain compounds of the present invention may exist in unsolvated or solvated forms, including hydrated forms. Generally speaking, the solvated form is equivalent to the unsolvated form, and both are included in the scope of the present invention.

The compounds of the present invention may exist in specific geometric or stereoisomeric forms. The present invention contemplates all such compounds, including cis and trans isomers, (−)- and (+)-enantiomers, (R)- and (S)-enantiomers, diastereomers, (D)-isomers, (L)-isomers, and racemic mixtures and other mixtures thereof, such as enantiomerically or diastereomerically enriched mixtures, all of which fall within the scope of the present invention. Additional asymmetric carbon atoms may be present in a substituent such as an alkyl group. All these isomers and mixtures thereof are included in the scope of the present invention.

Unless otherwise stated, the term "enantiomer" or "optical isomers" refers to stereoisomers that are mirror images of each other.

Unless otherwise stated, the term "cis-trans isomer" or "geometric isomer" is caused by the fact that double bonds or single bonds of ring-forming carbon atoms cannot rotate freely.

Unless otherwise stated, the term "diastereomers" refers to stereoisomers in which molecules have two or more chiral centers and are not mirror images of each other.

Unless otherwise stated, "(+)" represents right-handed, "(−)" represents left-handed, and "(±)" means racemic.

Unless otherwise stated, the wedge-shaped solid bond (⬧) and the wedge-shaped dotted bond (⬧) represent the absolute configuration of a stereoscopic center; the straight solid bond (⬧) and straight dotted bond (⬧) represent the relative configuration of a ⬧ stereoscopic center; the wavy line (⬧) represents the wedge-shaped solid bond (⬧) or the ⬧ wedge-shaped dotted bond (⬧); or the wavy line (⬧) represents the straight solid bond (⬧) and the straight dotted bond (⬧).

The compounds of the present invention may exist in specific. Unless otherwise stated, the term "tautomer" or "tautomeric form" means that at room temperature, isomers with different functional groups are in dynamic equilibrium and can be quickly converted to each other. Where tautomerization is possible (such as in solution), a chemical equilibrium of tautomers can be achieved. For example, proton tautomers (also known as prototropic tautomers) include interconversion via migration of a proton, such as keto-enol isomerization and imine-enamine isomerization. Valence tautomers include some interconversions by recombination of some of bond-forming electrons. A specific example of keto-enol tautomerization is the interconversion between two tautomers, pentane-2,4-dione and 4-hydroxypent-3-en-2-one.

Unless otherwise stated, the terms "rich in one isomer", "isomer enriched", "rich in one enantiomer" or "enantiomerically enriched" refer to the content of one of the isomers or enantiomers is less than 100%, and the content of the isomer or enantiomer is greater than or equal to 60%, or greater than or equal to 70%, or greater than or equal to 80%, or greater than or equal to 90%, or greater than or equal to 95%, or greater than or equal to 96%, or greater than or equal to 97%, or greater than or equal to 98%, or greater than or equal to 99%, or greater than or equal to 99.5%, or greater than or equal to 99.6%, or greater than or equal to 99.7%, or greater than or equal to 99.8%, or greater than or equal to 99.9%.

Unless otherwise stated, the term "isomer excess" or "enantiomeric excess" refers to the difference between the relative percentages of two isomers or two enantiomers. For example, if the content of one isomer or enantiomer is 90%, and the content of the other isomer or enantiomer is 10%, the isomer or enantiomer excess (ee value) is 80%.

Optically active (R)- and (S)-isomers and D and L isomers can be prepared using chiral synthesis or chiral reagents or other conventional techniques. If a particular enantiomer of a compound of the present invention is desired, it can be prepared by asymmetric synthesis or derivatization with a chiral auxiliary, wherein the resulting diastereomeric mixture is separated and the auxiliary groups are cleaved to provide pure desired enantiomers. Alternatively, where the molecule contains a basic functional group (such as an amino group) or an acidic functional group (such as a carboxyl group), diastereomeric salts can be formed with an appropriate optically active acid or base, followed by resolution of the diastereomers using conventional methods well known in the art, and subsequent recovery of the pure enantiomers. In addition, separation of enantiomers and diastereomers is frequently accomplished using chromatography, which uses chiral stationary phases, optionally in combination with chemical derivatization methods (e.g., formation of carbamates from amines). The compounds of the present invention may contain unnatural proportions of atomic isotopes at one or more of the atoms constituting the compound. For example, the compounds may be radiolabeled with radioactive isotopes, such as tritium ($^3H$), iodine-125 ($^{125}I$) or C-14 ($^{14}C$). For another example, the hydrogen can be substituted by heavy hydrogen to form deuterated drugs. The bond formed by deuterium and carbon is stronger than the bond formed by ordinary hydrogen and carbon. Compared with undeuterated drugs, deuterated drugs have reduced toxic side effects, increased drug stability, enhanced efficacy, prolonged biological half-life of drugs and other advantages. All isotopic variations of the compounds of the present invention, whether radioactive or not, are intended to be encompassed within the scope of the present invention. "Optional" or "optionally" means that the subsequently described event or circumstance may, but not necessarily occur, and that the description includes instances where said event or circumstance occurs and instances where said event or circumstance does not occur.

The term "substituted" means that any one or more hydrogen atoms on the designated atom is substituted by a substituent, which may include heavy hydrogen and hydrogen variants, provided that the valence state of the designated atom is normal, and the substituted compound is stable. Where the substituent is oxygen (i.e., =O), it means that two hydrogen atoms are substituted. Oxygen substitution does not occur on aromatic groups. The term "optionally substituted" means that it may or may not be substituted. Unless otherwise specified, the type and number of substituents may be arbitrary on the basis that they can be achieved in chemistry.

Where any variable (such as R) appears more than once in the composition or structure of a compound, its definition in each case is independent. Thus, for example, if a group is substituted with 0-2 R, the group can optionally be substituted with up to two R, and R in each case has independent options. In addition, combinations of substituents and/or variants thereof are permissible only if such combinations result in stable compounds.

When the number of a linking group is 0, such as —(CRR)$_0$—, it means that the linking group is a single bond.

When one of the variables is selected from a single bond, it means that the two groups to which it is connected are directly connected. For example, when L represents a single bond in A-L-Z, it means that the structure is actually A-Z.

When a substituent is vacant, it means that the substituent does not exist. For example, when X is vacant in A-X, it means that the structure is actually A. When the substituents listed do not indicate through which atom they are connected to the substituted group, such substituents can be bonded through any of the atoms thereof, for example, pyridyl as a substituent can be attached to the substituted group via any carbon atom on the pyridine ring.

When the linking group listed does not indicate the linking direction thereof, the linking direction is arbitrary, for example, the linking group L is -M-W— in

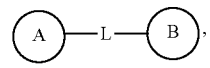

at this situation, -M-W— can connect ring A and ring B in the same direction as the reading order from left to right to form

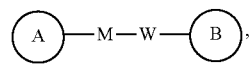

and can also connect ring A and ring B in the opposite direction as the reading order from left to right to form

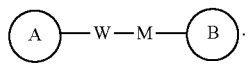

Combinations of the linking groups, substituents, and/or variants thereof permissible only if such combinations result in stable compounds.

Unless otherwise specified, the term "hetero" means a heteroatom or a heteroatomic group (i.e., an atomic groups containing a heteroatom), including atoms other than carbon (C) and hydrogen (H) as well as atomic groups containing such heteroatoms, for example, oxygen (O), nitrogen (N), sulfur (S), silicon (Si), germanium (Ge), aluminum (Al), boron (B), —O—, —S—, —C(=O)O—, —C(=O)—, —C(=S)—, —S(=O), —S(=O)$_2$—, and optionally substituted —C(=O)N(H)—, —N(H)—, —C(=NH)—, —S(=O)$_2$N(H)— or —S(=O)N(H)—.

Unless otherwise specified, "ring" means substituted or unsubstituted cycloalkyl, heterocycloalkyl, cycloalkenyl, heterocycloalkenyl, cycloalkynyl, heterocycloalkynyl, aryl, or heteroaryl. The ring includes a monocyclic ring, and also includes a spiro ring, a fused ring, a bridge ring and other bicyclic or polycyclic ring systems. The number of atoms in a ring is usually defined as the member number of the ring. For example, "5- to 7-membered ring" means that there are 5 to 7 atoms arranging in a circle. Unless otherwise specified, the ring optionally contains 1 to 3 heteroatoms. Therefore, "5- to 7-membered ring" includes, for example, phenyl, pyridyl, and piperidinyl; on the other hand, the term "5- to 7-membered heterocycloalkyl" includes pyridyl and piperidyl, but excludes phenyl. The term "ring" also includes ring systems containing at least one ring, each ring of which independently conforms to the above definition.

Unless otherwise specified, "5- to 6-membered ring" means cycloalkyl, heterocycloalkyl, cycloalkenyl, heterocycloalkenyl, cycloalkynyl, heterocycloalkynyl, aryl or heteroaryl consisting of 5 to 6 ring atoms. The ring includes a monocyclic ring, and also includes a spiro ring, a fused ring, a bridge ring and other bicyclic ring systems. Unless otherwise specified, the ring optionally contains 1, 2 or 3 heteroatoms independently selected from O, S and N. The 5- to 6-member ring includes 5 membered ring, 6 membered ring and the like. The "5- to 6-membered ring" includes, for example, phenyl, pyridyl, piperidinyl and the like; on the other hand, the term "5- to 6-membered heterocycloalkyl" includes piperidyl, but excludes phenyl. The term "ring" also includes ring systems containing at least one ring, each ring of which independently conforms to the above definition.

Unless otherwise specified, "C$_{3-6}$ cycloalkyl" means a saturated cyclic hydrocarbon group consisting of 3 to 6 carbon atoms, which comprises a monocyclic and bicyclic ring system, and the C$_{3-6}$ cycloalkyl includes C$_{3-5}$, C$_{4-5}$, and C$_{5-6}$ cycloalkyl; it can be monovalent, bivalent or multivalent. Examples of C$_{3-6}$ cycloalkyl include, but are not limited to, cyclopropyl, cyclobutyl, cyclopentyl and cyclohexyl.

Unless otherwise specified, the term "5- to 6-membered heterocycloalkyl" by itself or in combination with other terms respectively represents a saturated cyclic group consisting of 5 to 6 ring atoms, of which 1, 2, 3 or 4 ring atoms are heteroatoms independently selected from O, S and N, and the rest of which are carbon atoms, wherein the nitrogen atom is optionally quaternized, and the nitrogen and sulfur heteroatoms can be optionally oxidized (i.e., NO and S(O)$_p$, wherein p is 1 or 2). It comprises a monocyclic and bicyclic ring system, wherein the bicyclic system includes a spiro ring, a fused ring, and a bridge ring. In addition, in terms of the "5- to 6-membered heterocycloalkyl", the heteroatom may occupy the connection position of the heterocyclic alkyl to the remainder of the molecule. The 5- to 6-membered heterocycloalkyl includes 5-membered and 6-membered heterocycloalkyl. Examples of 5- to 6-membered heterocycloalkyl include, but are not limited to, pyrrolidinyl, pyrazolidinyl, imidazolidinyl, tetrahydrothienyl (including tetrahydrothien-2-yl and tetrahydrothien-3-yl), tetrahydrofuranyl (including tetrahydrofuran-2-yl), tetrahydropyranyl, piperidinyl (including 1-piperidinyl, 2-piperidinyl, and 3-piperidinyl), piperazinyl (including 1-piperazinyl and 2-piperazinyl), morpholinyl (including 3-morpholinyl and 4-morpholinyl), dioxanyl, dithianyl, isoxazolidinyl, isothiazolidinyl, 1,2-oxazinyl, 1,2-thiazinyl, hexahydropyridazinyl, homopiperazinyl or homopiperidinyl.

Unless otherwise specified, the terms "5- to 6-membered heteroaryl ring" and "5- to 6-membered heteroaryl" of the present invention can be used interchangeably, and the term "5- to 6-membered heteroaryl" represents a monocyclic group having a conjugated π-electron system and consisting of 5 to 6 ring atoms, of which 1, 2, 3, or 4 ring atoms are heteroatoms independently selected from O, S, and N, and the rest of which are carbon atoms, wherein nitrogen atoms are optionally quaternized, and nitrogen and sulfur heteroatoms can be optionally oxidized (i.e., NO and S(O)$_p$, wherein p is 1 or 2). The 5- to 6-membered heteroaryl can be connected to the remainder of the molecule via a heteroatom or a carbon atom. The 5- to 6-membered heteroaryl includes 5-membered and 6-membered heteroaryl. Examples of the 5- to 6-membered heteroaryl include, but are not limited to, pyrrolyl (including N-pyrrolyl, 2-pyrrolyl and 3-pyrrolyl), pyrazolyl (including 2-pyrazolyl and 3-pyrazolyl), imidazolyl (including N-imidazolyl, 2-imidazolyl, 4-imidazolyl and 5-imidazolyl), oxazolyl (including 2-oxazolyl, 4-oxazolyl and 5-oxazolyl), triazolyl (1H-1,2,3-triazolyl, 2H-1,2,3-triazolyl, 1H-1,2,4-triazolyl and 4H-1,2,4-triazolyl), tetrazolyl, isoxazolyl (3-isoxazolyl, 4-isoxazolyl and 5-isoxazolyl), thiazolyl (including 2-thiazolyl, 4-thiazolyl and 5-thiazolyl), furyl (including 2-furanyl and 3-furanyl), thienyl (including 2-thienyl and 3-thienyl), pyridyl (including 2-pyridyl, 3-pyridyl and 4-pyridyl), pyrazinyl or pyrimidinyl (including 2-pyrimidyl and 4-pyrimidyl).

Unless otherwise specified, the term "alkyl" is used to represent a linear or branched saturated hydrocarbon group. In some embodiments, the alkyl is C$_{1-12}$ alkyl. In other embodiments, the alkyl is C$_{1-6}$ alkyl. In other embodiments, the alkyl is C$_{1-3}$ alkyl. It may be mono-substituted (such as —CH$_2$F) or poly-substituted (such as —CF$_3$), and may be monovalent (such as methyl), divalent (such as methylene) or polyvalent (such as methine). Examples of alkyl include, but are not limited to, methyl (Me), ethyl (Et), propyl (including n-propyl and isopropyl), butyl (including n-butyl, isobutyl, s-butyl and t-butyl), pentyl (including n-pentyl, isopentyl and neopentyl) and hexyl.

Unless otherwise specified, the term "C$_{1-6}$ alkyl" is used to represent a linear or branched saturated hydrocarbon group consisting of 1 to 6 carbon atoms. The C$_{1-6}$ alkyl includes C$_{1-5}$, C$_{1-4}$, C$_{1-3}$, C$_{1-2}$, C$_{2-6}$, C$_{2-4}$, C$_6$ and C$_5$ alkyl; It can be monovalent (such as methyl), divalent (such as methylene) or multivalent (such as methine). Examples of C$_{1-6}$ alkyl include, but are not limited to, methyl (Me), ethyl (Et), propyl (including n-propyl and isopropyl), butyl (including n-butyl, isobutyl, s-butyl and t-butyl), pentyl (including n-pentyl, isopentyl and neopentyl) and hexyl.

Unless otherwise specified, the term "$C_{1-3}$ alkyl" is used to represent a linear or branched saturated hydrocarbon group consisting of 1 to 3 carbon atoms. The $C_{1-3}$ alkyl includes $C_{1-2}$ and $C_{2-3}$ alkyl; It can be monovalent (such as methyl), divalent (such as methylene) or multivalent (such as methine). Examples of $C_{1-3}$ alkyl include, but are not limited to, methyl (Me), ethyl (Et) and propyl (including n-propyl and isopropyl).

Unless otherwise specified, "alkenyl" is used to represent a linear or branched hydrocarbon group containing one or more carbon-carbon double bonds, which may be located at any position of the group. In some embodiments, the alkenyl is $C_{2-8}$ alkenyl. In other embodiments, the alkenyl is $C_{2-6}$ alkenyl. In other embodiments, the alkenyl is $C_{2-4}$ alkenyl. It may be mono-substituted or poly-substituted, and may be monovalent, divalent or polyvalent. Examples of alkenyl include, but are not limited to, vinyl, propenyl, butenyl, pentenyl, hexenyl, butadienyl, piperylene and hexadienyl.

Unless otherwise specified, "alkynyl" is used to represent a linear or branched hydrocarbon group containing one or more carbon-carbon triple bonds which may be located at any position of the group. In some embodiments, the alkynyl is $C_{2-8}$ alkynyl. In other embodiments, the alkynyl is $C_{2-6}$ alkynyl. In other embodiments, the alkenyl is $C_{2-4}$ alkynyl. It may be mono-substituted or poly-substituted, and may be monovalent, divalent or polyvalent. Examples of alkynyl include, but are not limited to, ethynyl, propynyl, butynyl and pentynyl.

Unless otherwise specified, the term "heteroalkyl" by itself or in combination with another term means a stable linear or branched alkyl atomic group consisting of a certain number of carbon atoms and at least one heteroatom or heteroatomic group, or a combination thereof. In some embodiments, the heteroatom is selected from B, O, N and S, wherein the nitrogen and sulfur atoms are optionally oxidized, and the nitrogen heteroatom is optionally quaternized. In other embodiments, the heteroatomic group is selected from —C(=O)O—, —C(=O)—, —C(=S)—, —S(=O), —S(=O)$_2$—, —C(=O)N(H)—, —N(H)—, —C(=NH)—, —S(=O)$_2$N(H)— and —S(=O)N(H)—. In some embodiments, the heteroalkyl is $C_{1-6}$ heteroalkyl. In other embodiments, the heteroalkyl is $C_{1-3}$ heteroalkyl. Heteroatom or heteroatomic group may be located at any internal position of heteroalkyl, including the connection positions of the alkyl to the remainder of the molecule. However, the terms "alkoxy", "alkylamino" and "alkylthio" (or thioalkoxy) are used in their conventional sense and refer to those alkyl groups attached to the remainder of the molecule via an oxygen atom, an amino group, or a sulfur atom, respectively. Examples of heteroalkyl include, but are not limited to, —OCH$_3$, —OCH$_2$CH$_3$, —OCH$_2$CH$_2$CH$_3$, —OCH$_2$(CH$_3$)$_2$, —CH$_2$—CH$_2$—O—CH$_3$, —NHCH$_3$, —N(CH$_3$)$_2$, —NHCH$_2$CH$_3$, —N(CH$_3$)(CH$_2$CH$_3$), —CH$_2$—CH$_2$—NH—CH$_3$, —CH$_2$—CH$_2$—N(CH$_3$)—CH$_3$, —SCH$_3$, —SCH$_2$CH$_3$, —SCH$_2$CH$_2$CH$_3$, —SCH$_2$(CH$_3$)$_2$, —CH$_2$—S—CH$_2$—CH$_3$, —CH$_2$—CH$_2$, —S(=O)—CH$_3$, —CH$_2$—CH$_2$—S(=O)$_2$—CH$_3$, —CH=CH—O—CH$_3$, —CH$_2$—CH=N—OCH$_3$ and —CH=CH—N(CH$_3$)—CH$_3$, wherein at most two heteroatoms may be continuous, such as —CH$_2$—NH—OCH$_3$.

Unless otherwise specified, the term "heteroalkenyl" by itself or in combination with another term means a stable linear or branched alkenyl atomic group consisting of a certain number of carbon atoms and at least one heteroatom or heteroatomic group, or a combination thereof. In some embodiments, the heteroatom is selected from B, O, N and S, wherein the nitrogen and sulfur atoms are optionally oxidized, and the nitrogen heteroatom is optionally quaternized. In other embodiments, the heteroatomic group is selected from —C(=O)O—, —C(=O)—, —C(=S)—, —S(=O), —S(=O)$_2$—, —C(=O)N(H)—, —N(H)—, —C(=NH)—, —S(=O)$_2$N(H)— and —S(=O)N(H)—. In some embodiments, the heteroalkenyl is $C_{2-6}$ heteroalkenyl. In other embodiments, the heteroalkyl is $C_{2-4}$ heteroalkenyl. Heteroatom or heteroatomic group may be located at any internal position of heteroalkenyl, including the connection positions of the alkenyl to the remainder of the molecule. However, the terms "alkenyloxy", "alkenylamino" and "alkenylthio" are used in their conventional sense and refer to those alkenyl groups attached to the remainder of the molecule via an oxygen atom, an amino group, or a sulfur atom, respectively. Examples of heteroalkenyl groups include, but are not limited to, —O—CH=CH$_2$, —O—CH=CHCH$_3$, —O—CH=C(CH$_3$)$_2$, —CH=CH—O—CH$_3$, —O—CH=CHCH$_2$CH$_3$, —CH$_2$—CH=CH—OCH$_3$, —NH—CH=CH$_2$, —N(CH=CH$_2$)—CH$_3$, —CH=CH—NH—CH$_3$, —CH=CH—N(CH$_3$)$_2$, —S—CH=CH$_2$, —S—CH=CHCH$_3$, —S—CH=C(CH$_3$)$_2$, —CH$_2$—S—CH=CH$_2$, —S(=O)—CH=CH$_2$ and —CH=CH—S(=O)$_2$—CH$_3$, wherein at most two heteroatoms can be continuous, such as —CH=CH—NH—OCH$_3$.

Unless otherwise specified, the term "heteroalkynyl" by itself or in combination with another term means a stable linear or branched alkynyl atomic group consisting of a certain number of carbon atoms and at least one heteroatom or heteroatomic group, or a combination thereof. In some embodiments, the heteroatom is selected from B, O, N and S, wherein the nitrogen and sulfur atoms are optionally oxidized, and the nitrogen heteroatom is optionally quaternized. In other embodiments, the heteroatomic group is selected from —C(=O)O—, —C(=O)—, —C(=S)—, —S(=O), —S(=O)$_2$—, —C(=O)N(H)—, —N(H)—, —C(=NH)—, —S(=O)$_2$N(H)— and —S(=O)N(H)—. In some embodiments, the heteroalkynyl is $C_{2-6}$ heteroalkynyl. In other embodiments, the heteroalkyl is $C_{2-4}$ heteroalkynyl. Heteroatom or heteroatomic group may be located at any internal position of heteroalkynyl, including the connection positions of the alkynyl to the remainder of the molecule. However, the terms "alkynyloxy", "alkynylamino" and "alkynylthio" are used in their conventional sense and refer to those alkynyl groups attached to the remainder of the molecule via an oxygen atom, an amino group, or a sulfur atom, respectively. Examples of heteroalkynyl include, but are not limited

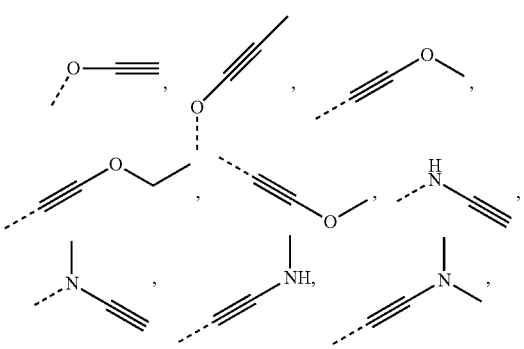

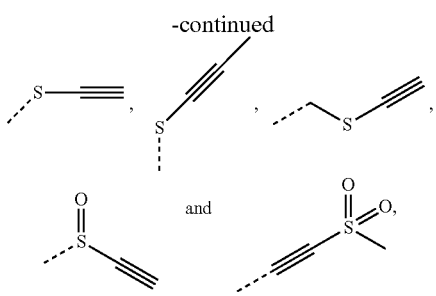

and at most two heteroatoms can be continuous, such as

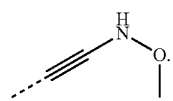

Unless otherwise specified, "cycloalkyl" includes any stable cyclic alkyl including a monocyclic, bicyclic or tricyclic ring system, wherein the bicyclic and tricyclic ring systems include a spiro ring, a fused ring, and a bridge ring. In some embodiments, the cycloalkyl is $C_{3-8}$ cycloalkyl. In other embodiments, the cycloalkyl is $C_{3-6}$ cycloalkyl. In other embodiments, the cycloalkyl is $C_{5-6}$ cycloalkyl. It may be mono-substituted or poly-substituted, and may be monovalent, divalent or polyvalent. Examples of the cycloalkyl include, but are not limited to, cyclopropyl, cyclobutyl, cyclopentyl, cyclohexyl, cycloheptyl, norbornyl, [2.2.2] bicyclooctane, and [4.4.0] bicyclodecane.

Unless otherwise specified, "cycloalkenyl" includes any stable cyclic alkenyl containing one or more unsaturated carbon-carbon double bonds at any position of the group, which includes a monocyclic, bicyclic or tricyclic system, wherein the bicyclic and tricyclic ring systems include a spiro ring, a fused ring, and a bridge ring, but any ring in the systems is non-aromatic. In some embodiments, the cycloalkenyl is $C_{3-8}$ cycloalkenyl. In other embodiments, the cycloalkenyl is $C_{3-6}$ cycloalkenyl. In other embodiments, the cycloalkenyl is $C_{5-6}$ cycloalkenyl. It may be mono-substituted or poly-substituted, and may be monovalent, divalent or polyvalent. Examples of the cycloalkenyl include, but are not limited to, cyclopentenyl and cyclohexenyl.

Unless otherwise specified, "cycloalkynyl" includes any stable cyclic alkynyl containing one or more carbon-carbon triple bonds at any position of the group, which includes a monocyclic, bicyclic or tricyclic ring system, wherein the bicyclic and tricyclic ring systems include a spiro ring, a fused ring, and a bridge ring. It may be mono-substituted or poly-substituted, and may be monovalent, divalent or polyvalent.

Unless otherwise specified, the term "heterocycloalkyl" by itself or in combination with other terms respectively represents a cyclized "heteroalkyl" group, which includes a monocyclic, bicyclic or tricyclic ring system, wherein the bicyclic and tricyclic ring systems include a spiro ring, a fused ring, and a bridge ring. In addition, in terms of the "heterocycloalkyl", the heteroatom may occupy the connection position of the heterocyclic alkyl to the remainder of the molecule. In some embodiments, the heterocycloalkyl is 4- to 6-membered heterocycloalkyl. In other embodiments, the heterocycloalkyl is 5- to 6-membered heterocycloalkyl. Examples of heterocycloalkyl include, but are not limited to, azetidinyl, oxetanyl, thiatanyl, pyrrolidinyl, pyrazolidinyl, imidazolidinyl, tetrahydrothienyl (including tetrahydrothiophene-2-yl and tetrahydrothiophen-3-yl), tetrahydrofuranyl (including tetrahydrofuran-2-yl), tetrahydropyranyl, piperidinyl (including 1-piperidinyl, 2-piperidinyl and 3-piperidinyl), piperazinyl (including 1-piperazinyl and 2-piperazinyl), morpholinyl (including 3-morpholinyl and 4-morpholinyl), dioxanyl, dithianyl, isoxazolidinyl, isothiazolidinyl, 1,2-oxazinyl, 1,2-thiazinyl, hexahydropyridazinyl, homopiperazinyl, homopiperidinyl or oxepanyl.

Unless otherwise specified, the term "heterocycloalkenyl" by itself or in combination with other terms respectively represents a cyclized "heteroalkenyl" group, which includes a monocyclic, bicyclic and tricyclic ring system, wherein the bicyclic and tricyclic ring systems include a spiro ring, a fused ring, and a bridge ring, but any ring in the systems is non-aromatic. In addition, in terms of the "heterocycloalkenyl", the heteroatom may occupy the connection position of the heterocycloalkenyl to the remainder of the molecule. In some embodiments, the heterocycloalkenyl is 4- to 6-membered heterocycloalkenyl. In other embodiments, the heterocycloalkenyl is 5- to 6-membered heterocycloalkenyl. Examples of heterocycloalkenyl include, but are not limited to,

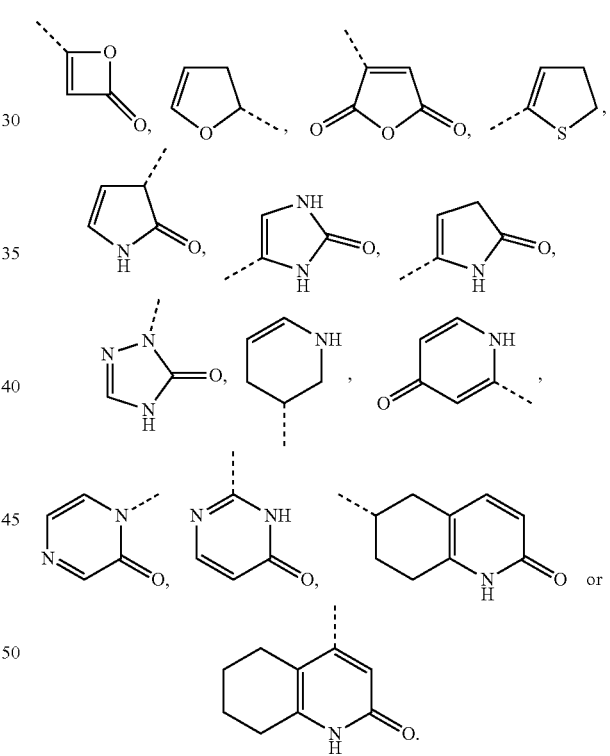

Unless otherwise specified, the term "heterocycloalkynyl" by itself or in combination with other terms respectively represents a cyclized "heteroalkynyl" group, which includes a monocyclic, bicyclic and tricyclic ring system, wherein the bicyclic and tricyclic ring systems include a spiro ring, a fused ring, and a bridge ring. In addition, in terms of the "heterocycloalkynyl", the heteroatom may occupy the connection position of the heterocycloalkynyl with the remainder of the molecule. In some embodiments, the heterocycloalkynyl is 4- to 6-membered heterocycloalkynyl. In other embodiments, the heterocycloalkynyl is 5- to 6-membered heterocycloalkynyl. Unless otherwise specified, the term "halo" or "halogen" by itself or as part of another substituent means a fluorine, chlorine, bromine or iodine atom. In addition, the term "haloalkyl" is intended to include monohaloalkyl and polyhaloalkyl. For example, the term "halo($C_1$-$C_4$)alkyl" is intended to include, but is not limited to, trifluoromethyl, 2,2,2-trifluoroethyl, 4-chlorobutyl and 3-bromopropyl. Unless otherwise specified, examples of haloalkyl include, but are not limited to: trifluoromethyl, trichloromethyl, pentafluoroethyl and pentachloroethyl.

"Alkoxy" represents the above alkyl having a specific number of carbon atoms connected via an oxygen bridge. Unless otherwise specified, $C_{1-6}$ alkoxy includes $C_1$, $C_2$, $C_3$, $C_4$, $C_5$ and $C_6$ alkoxy. In some embodiments, the alkoxy is $C_{1-3}$ alkoxy. Examples of alkoxy include, but are not limited to: methoxy, ethoxy, n-propoxy, isopropoxy, n-butoxy, sec-butoxy, tert-butoxy, n-pentoxy and S-pentoxy.

Unless otherwise specified, the terms "aromatic ring" and "aryl" in the present invention can be used interchangeably. The term "aromatic ring" or "aryl" means a polyunsaturated carbocyclic system, which may be a monocyclic, bicyclic or tricyclic system, in which at least one ring is aromatic, and the rings in the bicyclic and polycyclic ring systems are fused together. It may be mono-substituted or poly-substituted, and may be monovalent, divalent, or polyvalent. In some embodiments, the aryl is $C_{6-12}$ aryl. In other embodiments, the aryl is $C_{6-10}$ aryl. Examples of aryl include, but are not limited to, phenyl, naphthyl (including 1-naphthyl and 2-naphthyl). The substituent of any one of the above aryl ring systems is selected from the acceptable substituents described in the present invention.

Unless otherwise specified, the terms "heteroaryl ring" and "heteroaryl" of the present invention can be used interchangeably. The term "heteroaryl" refers to aryl (or aromatic ring) containing 1, 2, 3 or 4 heteroatoms independently selected from B, N, O and S, which may be a monocyclic, bicyclic or tricyclic ring system, wherein the nitrogen atom may be substituted or unsubstituted (i.e., N or NR, wherein R is H or other substituents already defined herein), and optionally quaternized, and the nitrogen and sulfur heteroatoms may be optionally oxidized (i.e., NO and $S(O)_p$, wherein p is 1 or 2). Heteroaryl can be connected to the remainder of the molecule via a heteroatom. In some embodiments, the heteroaryl is a 5- to 10-membered heteroaryl. In other embodiments, the heteroaryl is a 5- to 6-membered heteroaryl. Examples of the heteroaryl include, but are not limited to, pyrrolyl (including N-pyrrolyl, 2-pyrrolyl and 3-pyrrolyl), pyrazolyl (including 2-pyrazolyl and 3-pyrazolyl), imidazolyl (including N-imidazolyl, 2-imidazolyl, 4-imidazolyl and 5-imidazolyl), oxazolyl (including 2-oxazolyl, 4-oxazolyl and 5-oxazolyl), triazolyl (1H-1,2,3-triazolyl, 2H-1,2,3-triazolyl, 1H-1,2,4-triazolyl and 4H-1,2,4-triazolyl), tetrazolyl, isoxazolyl (3-isoxazolyl, 4-isoxazolyl, and 5-isoxazolyl), thiazolyl (including 2-thiazolyl, 4-thiazole and 5-thiazolyl), furyl (including 2-furanyl and 3-furanyl), thienyl (including 2-thienyl and 3-thienyl), pyridyl (including 2-pyridyl, 3-pyridyl and 4-pyridyl), pyrazinyl, pyrimidinyl (including 2-pyrimidinyl and 4-pyrimidinyl), benzothiazolyl (including 5-benzothiazolyl), purinyl, benzimidazolyl (including 2-benzimidazolyl), indolyl (including 5-indolyl), isoquinolinyl (including 1-isoquinolinyl and 5-isoquinolinyl), quinoxalinyl (including 2-quinoxalinyl and 5-quinoxalinyl), quinolinyl (including 3-quinolinyl and 6-quinolinyl), pyrazinyl, purinyl, and benzoxazolyl. The substituent of any one of the above heteroaryl ring systems is selected from the acceptable substituents described in the present invention.

Unless otherwise specified, the term "aralkyl" is intended to include those groups where an aryl group is attached to an alkyl group, and in some embodiments, the aralkyl is $C_{6-10}$ aryl-$C_{1-4}$ alkyl. In other embodiments, the aralkyl is $C_{6-10}$ aryl-$C_{1-2}$ alkyl. Examples of aralkyl include, but are not limited to, benzyl, phenethyl, and naphthylmethyl. "Aryloxy" and "arylthio" respectively represent those groups in which the carbon atom (such as methyl) in the aralkyl group is replaced by an oxygen or sulfur atom, and in some embodiments, the aryloxy is $C_{6-10}$ aryl-O—$C_{1-2}$ alkyl. In embodiments, the aryloxy is $C_{6-10}$ aryl-$C_{1-2}$ alkyl-O—. In other embodiments, the arylthio is $C_{6-10}$ aryl-S—$C_{1-2}$ alkyl. In other embodiments, the arylthio is $C_{6-10}$ aryl-$C_{1-2}$ alkyl-S—. Examples of aryloxy and arylthio include, but are not limited to, phenoxymethyl, 3-(1-naphthyloxy)propyl, and phenylthiomethyl.

Unless otherwise specified, the term "heteroaralkyl" is intended to include those groups where an heteroaryl group is attached to an alkyl group, and in some embodiments, the heteroaralkyl is 5- to 8-membered heteroaryl-$C_{1-4}$ alkyl. In other embodiments, the heteroaralkyl is 5- to 6-membered heteroaryl-$C_{1-2}$ alkyl. Examples of heteroaralkyl include, but are not limited to, pyrrolylmethyl, pyrazolylmethyl, pyridylmethyl, and pyrimidinylmethyl. "Heteroaryloxy" and "heteroarylthio" respectively represent those groups in which the carbon atom (such as methyl) in the heteroaralkyl group is replaced by an oxygen or sulfur atom, and in some embodiments, the heteroaryloxy is 5- to 8-membered heteroaryl-O—$C_{1-2}$ alkyl. In other embodiments, the heteroaryloxy is 5- to 6-membered heteroaryl-$C_{1-2}$ alkyl-O—. In some embodiments, the heteroarylthio is 5- to 8-membered heteroaryl-S—$C_{1-2}$ alkyl. In other embodiments, the heteroarylthio is 5- to 6-membered heteroaryl-$C_{1-2}$ alkyl-S—. Examples of heteroaryloxy and heteroarylthio include, but are not limited to, pyrroleoxymethyl, pyrazolyloxymethyl, 2-pyridyloxymethyl, pyrrolylmethyl, pyrazolylmethyl, and 2-pyridylthiomethyl.

Unless otherwise specified, $C_{n-n+m}$ or $C_n$-$C_{n+m}$ includes any specific case of n to n+m carbons, for example, $C_{1-12}$ includes $C_1$, $C_2$, $C_3$, $C_4$, $C_5$, $C_6$, $C_7$, $C_8$, $C_9$, $C_{10}$, $C_{11}$ and $C_{12}$, and also includes any range from n to n+m, for example, $C_{1-12}$ includes $C_{1-3}$, $C_{1-6}$, $C_{1-9}$, $C_{3-6}$, $C_{3-9}$, $C_{3-12}$, $C_{6-9}$, $C_{6-12}$, and $C_{9-12}$; Similarly, n– membered to n+m– membered means that the number of atoms in the ring is n to n+m, for example, a 3- to 12-membered ring includes a 3-membered ring, a 4-membered ring, a 5-membered ring, a 6-membered ring, a 7-membered ring, a 8-membered ring, a 9-membered ring, a 10-membered ring, a 11-membered ring, and a 12-membered ring, and also includes any range from n to n+m, for example, a 3- to 12-membered ring includes a 3- to 6-membered ring, a 3- to 9-membered ring, a 5- to 6-membered ring, a 5- to 7-membered ring, a 6- to 7-membered ring, a 6- to 8-membered ring, and a 6- to 10-membered ring.

The term "leaving group" refers to a functional group or atom that can be substituted by another functional group or atom through a substitution reaction (e.g., an affinity substitution reaction). For example, representative leaving groups include trifluoromethanesulfonate; chlorine, bromine and iodine; sulfonates, such as methanesulfonate, tosylate, p-bromobenzenesulfonate, and p-toluenesulfonate; and acyloxy, such as acetoxy and trifluoroacetoxy.

The term "protecting group" includes, but is not limited to, "amino protecting group", "hydroxy protecting group" or "mercapto protecting group". The term "amino protecting group" refers to a protecting group suitable for preventing side reactions occur at the nitrogen atom of an amino group.

Representative amino protecting groups include, but are not limited to: formyl; acyl, such as alkanoyl (e.g., acetyl, trichloroacetyl or trifluoroacetyl); alkoxycarbonyl, such as tert-butoxycarbonyl (Boc); aryl methoxycarbonyl, such as benzyloxycarbonyl (Cbz) and 9-fluorenylmethoxycarbonyl (Fmoc); aryl methyl, such as benzyl (Bn), triphenyl methyl (Tr), 1,1-bis-(4'-methoxyphenyl)methyl; silyl, such as trimethylsilyl (TMS) and tert-butyldimethylsilyl (TBS). The term "hydroxyl protecting group" refers to a protecting group suitable for preventing side reactions of a hydroxyl group. Representative hydroxyl protecting groups include, but are not limited to: alkyl, such as methyl, ethyl and tert-butyl; acyl, such as alkanoyl (e.g., acetyl); arylmethyl, such as benzyl (Bn), p-methoxybenzyl (PMB), 9-fluorenylmethyl (Fm) and diphenylmethyl (DPM); silyl, such as trimethylsilyl (TMS) and tert-butyldimethylsilyl (TBS).

The compounds of the present invention can be prepared by various synthetic methods well known to a person skilled in the art, including the specific embodiments listed below, the embodiments formed by the combination with other chemical synthesis methods, and equivalent alternative embodiments well known to a person skilled in the art, wherein the preferred embodiments include but are not limited to the examples of the present invention.

The solvents used in the present invention are commercially available. The present invention uses the following abbreviations: aq represents water; HATU represents O-(7-azabenzotriazol-1-yl)-N,N,N'N'-tetramethylurea hexafluorophosphate; EDC represents N-(3-dimethylaminopropyl)-N'-ethylcarbodiimide hydrochloride; m-CPBA represents 3-chloroperoxybenzoic acid; eq represents equivalent; CDI represents carbonyldiimidazole; DCM represents dichloromethane; PE represents petroleum ether; DIAD represents diisopropyl azodiformate; DMF represents N,N-dimethylformamide; DMSO represents dimethyl sulfoxide; EtOAc represents ethyl acetate; EtOH represents ethanol; MeOH represents methanol; CBz represents benzyloxycarbonyl, which is an amine protecting group; BOC represents tert-butoxycarbonyl, which is an amine protecting group; HOAc represents acetic acid; NaCNBH$_3$ represents sodium cyanoborohydride; r.t. represents room temperature; O/N represents overnight; THF represents tetrahydrofuran; Boc$_2$O represents di-tert-butyl dicarbonate; TFA represents trifluoroacetic acid; DIPEA represents diisopropylethylamine; SOCl$_2$ represents thionyl chloride; CS$_2$ represents carbon disulfide; TsOH represents p-toluenesulfonic acid; NFSI represents N-fluoro-N-(benzenesulfonyl)benzenesulfonamide; NCS represents 1-chloropyrrolidine-2,5-dione; n-Bu$_4$NF represents tetrabutylammonium fluoride; iPrOH represents 2-propanol; mp represents melting point; LDA represents lithium diisopropylamide; Pd(dba)$_2$ represents tris(dibenzylideneacetone)dipalladium; Xantphos represents 4,5-bisdiphenylphosphine-9,9-dimethylxanthene; Pd(dppf)Cl$_2$ represents [1,1'-bis(diphenylphosphino)ferrocene]palladium dichloride; AUC represents area under the blood drug concentration-time curve; AUC0-last represents area under the plasma concentration-time curve from time zero to the last detectable concentration time point; AUC0-inf represents area under the plasma concentration-time curve from time zero to infinity; Cmax represents peak concentration; MRT represents average residence time; MRT0-last represents average residence time from time zero to the last detectable concentration time point; MRT0-inf represents average residence time from time zero to infinity; Tmax represents peak time; T1/2 represents half-life; C$_0$ represents initial concentration; Cl represents clearance rate; T$_{last}$ represents the last quantifiable time point; and PO represents oral.

Compounds are named by hand or ChemDraw® software, and commercially available compounds are named by the supplier catalog names.

DETAILED DESCRIPTION OF EMBODIMENTS

The present invention will be described in detail with the following examples, but not imply any adverse limitation to the present invention. The present invention has been described in detail herein, and the specific embodiments thereof are also disclosed therein. For a person skilled in the art, without departing from the spirit and scope of the present invention, all the variations and improvements made to the specific embodiments of the present invention would have been obvious.

Reference Example 1: Fragment BB-1

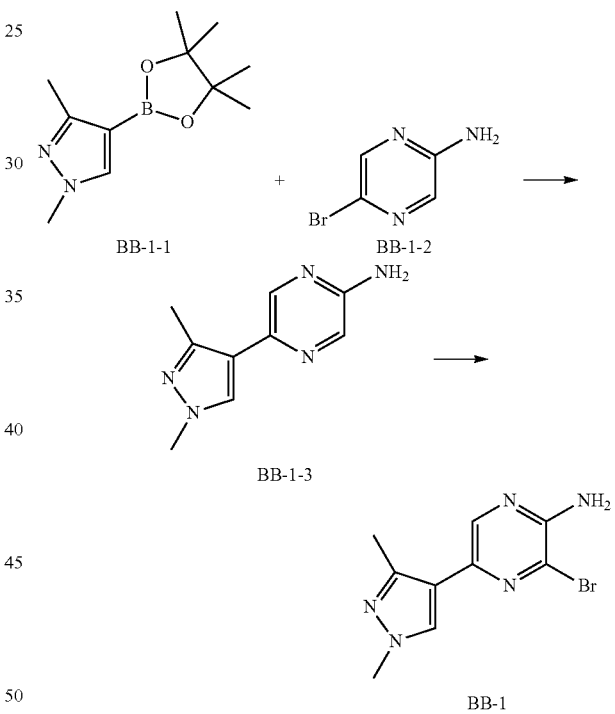

Step 1: Synthesis of Compound BB-1-3

Compound BB-1-2 (2.0 g, 11.49 mmol, 1 eq) and compound BB-1-1 (2.6 g, 11.49 mmol, 1 eq) are dissolved in water (6.0 mL) and dioxane (25.0 mL), and then added with [1,1'-bis(diphenylphosphino)ferrocene]palladium dichloride (841 mg, 1.15 mmol, 0.1 eq) and potassium carbonate (4.8 g, 34.48 mmol, 3 eq), and the solution is heated to 100° C. and reacted for 16 hours under nitrogen protection. The resulting reaction solution is subjected to suction filtration and rotary evaporation, and the crude product is purified by column chromatography (petroleum ether:ethyl acetate=1:0 to 0:1) to obtain compound BB-1-3.

MS (ESI) m/z: 189.0 [M+H]$^+$.

Step 2: Synthesis of Compound BB-1

Compound BB-1-3 (0.5 g, 2.64 mmol, 1 eq) and pyridine (209 mg, 2.64 mmol, 213.28 μL, 1 eq) are added to chloroform (20.0 mL), and cooled to 0° C., and then bromine (422 mg, 2.64 mmol, 136.22 μL, 1 eq) is added. The solution is reacted at room temperature 28° C. for 18 hours. The reactant is quenched with sodium thiosulfate (1.0 mL), and then subjected to suction filtration, and the filtrate is concentrated. The crude product is purified by flash column chromatography on silica gel (petroleum ether:ethyl acetate=1:0 to 1:1) to obtain compound BB-1. MS (ESI) m/z: 267.9 [M+H]$^+$.

$^1$H NMR (400 MHz, MeOH) δ: 8.12 (s, 1H) 7.90 (s, 1H) 3.86 (s, 3H) 2.43 (s, 3H).

Reference Example 2: Fragment BB-2

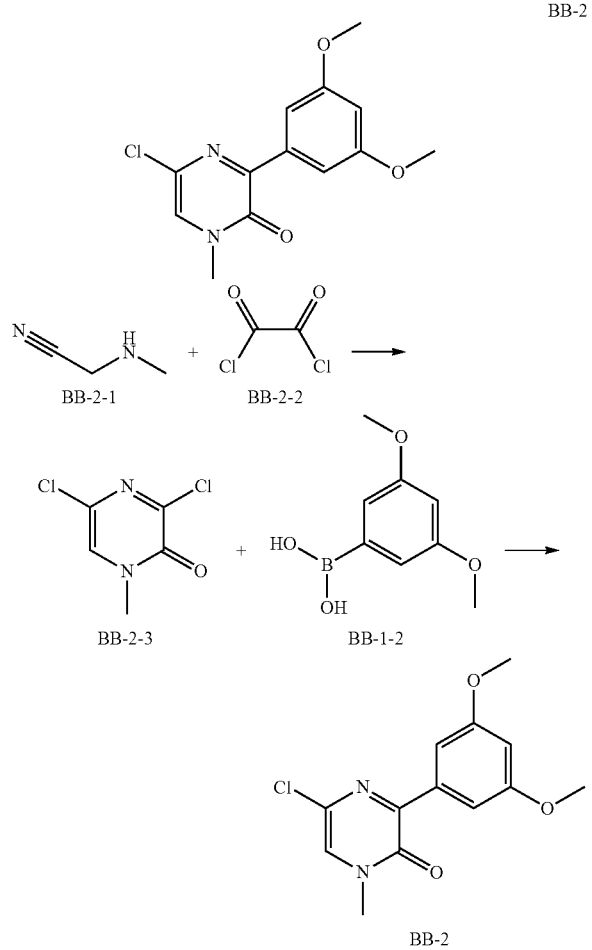

Step 1: Synthesis of Compound BB-2-3

Under nitrogen protection, compound BB-2-1 (2.0 g, 18.77 mmol, 2.17 mL, 1 eq, HCl) is dissolved in chlorobenzene (15.0 mL); compound BB-2-2 (8.3 g, 65.69 mmol, 5.8 mL, 3.5 eq) is added dropwise at 25° C.; and the mixture is slowly heated to 90° C. and stirred for 16 hours. Water (30.0 mL) and ethyl acetate (30.0 mL) are added to the reaction system, and allowed to stand still for layer separation, while the aqueous phase is extracted three times with ethyl acetate (20.0 mL, 20.0 mL, 20.0 mL). The organic phases are combined and washed once with saturated sodium chloride solution (30.0 mL); finally, the organic phase is dried over anhydrous sodium sulfate, filtered and concentrated under reduced pressure. The crude product is separated and purified by column chromatography (petroleum ether:ethyl acetate=1:0 to 2:1) to obtain compound BB-2-3. MS (ESI) m/z: 178.7 [M+1]$^+$.

$^1$H NMR (400 MHz, CHCl$_3$) δ: 7.26 (s, 1H), 3.61 (s, 3H).

Step 2: Synthesis of Compound BB-2

In a microwave tube, under nitrogen protection, compound BB-2-3 (0.2 g, 1.12 mmol, 1 eq) and compound BB-1-2 (213 mg, 1.17 mmol, 1.05 eq) are dissolved in a mixed solution of dioxane (1.5 mL) and water (1.5 mL), and added with tetrakistriphenylphosphorpalladium (65 mg, 55.86 μmol, 0.05 eq) and sodium carbonate (130 mg, 1.23 mmol, 1.1 eq), and the mixture is stirred in a microwave at 120° C. for 30 minutes. The reaction solution is directly concentrated. The crude product is separated by column chromatography (petroleum ether:ethyl acetate=1:0 to 0:1) (TLC detection, petroleum ether:ethyl acetate=1:1) to obtain compound BB-2. MS (ESI) m/z: 279.0 [M+1]$^+$.

$^1$H NMR (400 MHz, CHCl$_3$) δ: 7.64 (d, 2H), 7.28 (s, 1H), 6.59 (t, 1H), 3.86 (s, 6H), 3.61 (s, 3H).

Reference Example 3: Fragment BB-3

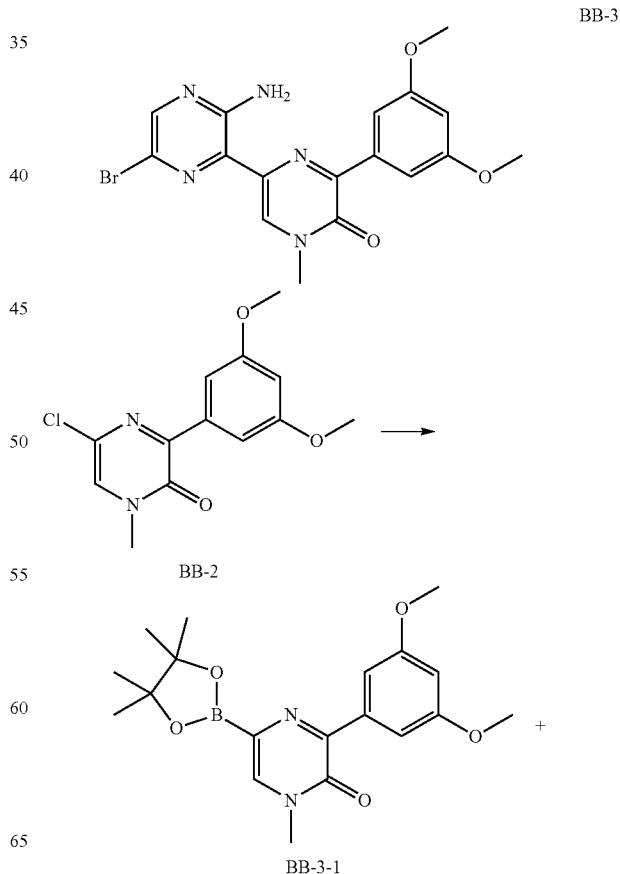

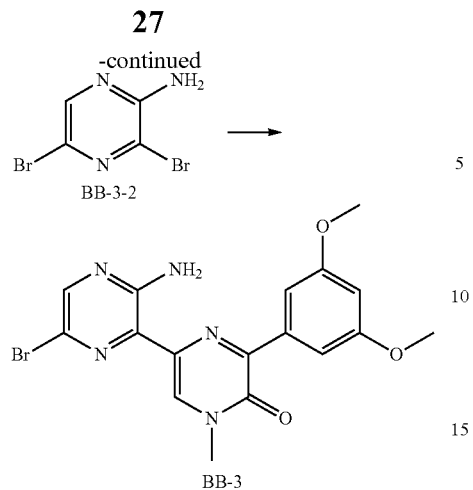

BB-3

Step 1: Synthesis of Compound BB-3-1

Compound BB-2 (150 mg, 660.63 μmol, 1 eq), bis (pinacolato)diboron (252 mg, 990.94 μmol, 1.5 eq), tris (dibenzylideneacetone)dipalladium (30 mg, 33.03 μmol, 0.05 eq), tricyclohexylphosphine (19 mg, 66.06 μmol, 21.42 μL, 0.1 eq) and potassium acetate (194 mg, 1.98 mmol, 3 eq) are dissolved in dioxane (4.0 mL). The mixed solution is heated to 90° C., continued to react for 16 hours under nitrogen protection and filtered while hot. The filtrate is concentrated to dryness under reduced pressure, added with a mixed solution of ethyl acetate and petroleum ether (10.0 mL) (ethyl acetate:petroleum ether=5:1), pulped for 30 minutes, and filtered to obtain compound BB-3-1. MS (ESI) m/z: 290.9 [M+H]$^+$.

Step 2: Synthesis of Compound BB-3

Compound BB-3-1 (450 mg, 1.55 mmol, 1 eq), compound BB-3-2 (510 mg, 2.02 mmol, 1.3 eq), tetratriphenylphosphine palladium (179 mg, 155.13 μmol, 0.1 eq) and potassium carbonate (643.20 mg, 4.65 mmol, 3 eq) are dissolved in dioxane (40.0 mL) and water (10.0 mL). The reaction mixed solution is heated to 100° C. and reacted for 2 hours under nitrogen protection. Ethyl acetate (30.0 mL) and water (50.0 mL) are added to the reaction solution, and stirred for 3 minutes, there being a solid precipitated. After being filtered, the resulting solid is washed with water (10.0 mL×3) three times, and washed with ethyl acetate (10.0 mL×3), and then dissolved in dichloromethane (50.0 mL). The resulting solution is dried over anhydrous sodium sulfate and filtered, and the filtrate is subjected to rotary evaporation under reduced pressure distillation to obtain compound BB-3. MS (ESI) m/z: 420.0 [M+H]$^+$.

$^1$H NMR (400 MHz, CHCl$_3$) δ: 8.35 (s, 1H), 7.96 (s, 1H), 7.36 (d, 2H), 6.53 (t, 1H), 3.78 (s, 6H), 3.69 (s, 3H).

Reference Example 4: Fragment BB-4

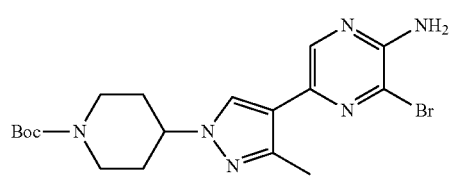

BB-4

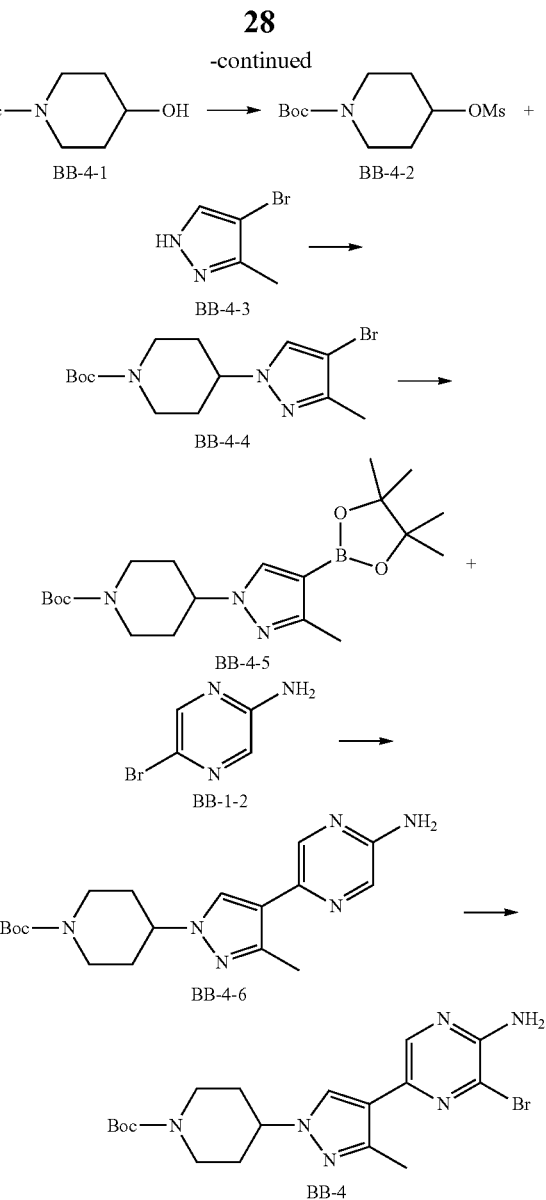

Step 1: Synthesis of Compound BB-4-2

Under nitrogen protection, compound BB-4-1 (5.0 g, 24.84 mmol, 1 eq) is dissolved in dichloromethane (350.0 mL), and methanesulfonyl chloride (3.1 g, 27.33 mmol, 2.1 mL, 1.1 eq) and triethylamine (2.8 g, 27.33 mmol, 3.3 mL, 2 eq) are added under ice bath. After the dropwise addition, the solution is heated to 25° C. and stirred for 2 hours. Water (15.0 mL) is added to the reaction solution to quench the reaction, and dichloromethane (30.0 mL×3) is used for extraction. The organic layers are combined, and washed once with saturated sodium chloride solution (20.0 mL); finally, the organic column is dried over anhydrous sodium sulfate, filtered and concentrated under reduced pressure to obtain compound BB-4-2. MS (ESI) m/z: 180.0 [M-Boc]$^+$.

Step 2: Synthesis of Compound BB-4-4

Compound BB-4-3 (3.3 g, 20.19 mmol, 1 eq) is dissolved in N,N-dimethylformamide (10.0 mL), added with sodium hydrogen (888 mg, 22.21p mol, 1.1 eq, purity: 60%) at 0° C.

under nitrogen protection, and stirred at 0° C. for 1 hour. Then compound BB-4-2 (6.2 g, 22.21 µmol, 1.1 eq) is added, and the solution is heated to 95° C. and reacted for 1 hour. The reaction solution is cooled to 25° C., and water (10.0 mL) is added to quench the reaction. The reaction solution is extracted with ethyl acetate (30.0 mL×3) three times. The organic phases are combined and washed with water (30.0 mL×3); finally, the organic phase is dried over anhydrous sodium sulfate, filtered and concentrated under reduced pressure. The crude product is separated and purified by column chromatography (petroleum ether:ethyl acetate=10:1) (TLC detection, petroleum ether:ethyl acetate=10:1) to obtain compound BB-4-4.

MS (ESI) m/z: 287.9 [M+H]$^+$.

Step 3: Synthesis of Compound BB-4-5

Under nitrogen protection, compound BB-4-4 (2.2 g, 6.39 mmol, 1 eq) and bis(pinacolato)diboron (2.4 g, 9.59 mmol, 1.5 eq) are dissolved in dioxane (10.0 mL), and added with [1,1'-bis(diphenylphosphino)ferrocene]palladium dichloride (468 mg, 639 µmol, 0.1 eq) and potassium acetate (1.3 g, 12.78 mmol, 2 eq). The air in the system is substituted with nitrogen three times, and then heated to 100° C. and stirred for 2 hours. The reaction solution is cooled to 25° C. and filtered through celite to obtain the filtrate, which is extracted with ethyl acetate (30.0 mL×3). The organic phases are combined; finally, the organic phase is dried over anhydrous sodium sulfate, filtered and concentrated under reduced pressure to obtain compound BB-4-5.

MS (ESI) m/z: 392.2 [M+H]$^+$.

Step 4: Synthesis of Compound BB-4-6

With regard to this step, reference can be made to the steps for synthesizing compounds BB-1-1 to BB-1-3, so as to obtain compound BB-4-6. MS (ESI) m/z: 437.0 [M+H]$^+$.

Step 5: Synthesis of Compound BB-4

Compound BB-4-6 (220 mg, 0.61 mmol, 1.0 eq) is dissolved in N,N-dimethylformamide (2.0 mL), and N-bromosuccinimide (109 mg, 0.61 mmol, 1.0 eq) is added at 0° C. After the addition, the solution is heated to 25° C. and reacted for 2 hours. The reaction solution is extracted with ethyl acetate (30.0 mL×3). The organic phases are combined and washed with water (30.0 mL×3); finally, the organic phase is dried over anhydrous sodium sulfate, filtered and concentrated under reduced pressure. The crude product is separated and purified by column chromatography (petroleum ether:ethyl acetate=1:1) (TLC detection, petroleum ether:ethyl acetate=1:1) to obtain compound BB-4. MS (ESI) m/z: 359.0 [M+H]$^+$.

Example 1: 0017

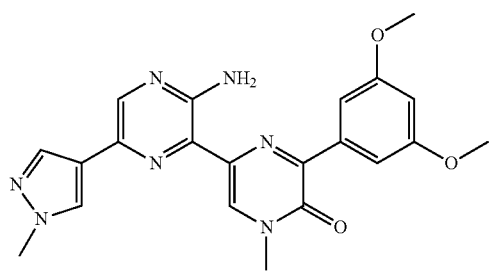

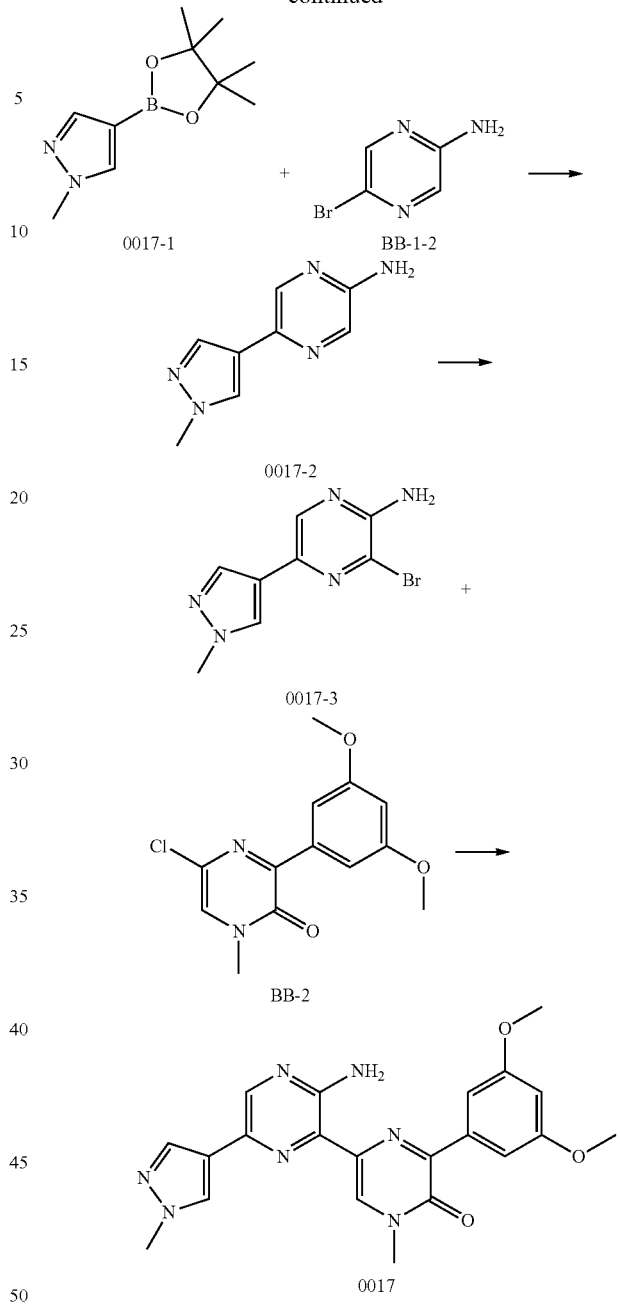

Step 1: Synthesis of Compound 0017-2

With regard to this step, reference can be made to the steps for synthesizing compounds BB-1-1 to BB-1-3, so as to obtain compound 0017-2. MS (ESI) m/z: 175.9 [M+H]$^+$.
$^1$H NMR (400 MHz, CHCl$_3$) δ: 8.20 (d, 1H), 7.96 (d, 1H), 7.86 (s, 1H), 7.78 (s, 1H), 4.63 (s, 2H), 3.99-3.88 (m, 3H).

Step 2: Synthesis of Compound 0017-3

Under nitrogen protection, compound 0017-2 (520 mg, 2.97 mmol, 1 eq) is dissolved in chloroform (20.0 mL), and pyridine (258 mg, 3.27 mmol, 263.53 µL, 1.1 eq) is added in one portion at 25° C. Compound bromine (474 mg, 2.97 mmol, 153 µL, 1 eq) is added dropwise at 0° C., and the mixture is stirred at 25° C. for 6 hours. The reaction solution is cooled to 0° C. The reaction is quench by slowly dropwise adding 10% aqueous sodium thiosulfate solution (20.0 ml), and extracted with dichloromethane (20.0 mL×3). The organic phases are combined and washed once with saturated sodium chloride solution (20.0 mL); finally, the organic phase is dried over anhydrous sodium sulfate, filtered and concentrated under reduced pressure. The crude product is separated and purified by column chromatography (petroleum ether:ethyl acetate:ethanol=1:0:0 to 4:3:1) to obtain compound 0017-3. MS (ESI) m/z: 255.9 [M+H]$^+$.

Step 3: Synthesis of Compound 0017

Compound BB-2 (50 mg, 178.12 μmol, 1 eq) and bis(pinacolato)diboron (45 mg, 178.12 μmol, 1 eq) are dissolved in dioxane (5.0 mL), and palladium acetate (4 mg, 17.81 μmol, 0.1 eq), 2-dicyclohexylphosphono-2,4,6-triisopropylbiphenyl (17 mg, 35.62 μmol, 0.2 eq), potassium acetate (52 mg, 534.37 μmol, 3 eq), compound 0017-3 (50 mg, 195.93 μmol, 1.1 eq), and a dichloromethane complex of [1,1'-bis(diphenylphosphino)ferrocene] palladium dichloride (16 mg, 19.59 μmol, 0.11 eq) and cesium carbonate (174 mg, 534.37 μmol, 3 eq) are added. The air in the system is substituted with nitrogen three times, and the mixture is stirred at 100° C. for 8 hours. The reaction solution is concentrated directly under reduced pressure. The obtained crude product is dissolved in ethyl acetate (4.0 mL), and separated and purified by a preparation plate (petroleum ether:ethyl acetate=0:1). The obtained yellow oily liquid is dissolved in methanol (5.0 mL), and the insoluble substance is filtered off. The filtrate is separated and purified by high-performance liquid chromatography (column: Waters Xbridge 150*25 mm 5 μm; mobile phase: [water (10 mM NH$_4$HCO$_3$)-ACN]; B %: 28%-58%, 6 minutes) to obtain compound 0017.

MS (ESI) m/z: 442.2 [M+H]$^+$.

$^1$H NMR (400 MHz, CHCl$_3$) δ: 8.50 (s, 1H), 8.20 (s, 1H), 7.93 (s, 1H), 7.82 (s, 1H), 7.50 (d, 2H), 6.61 (t, 1H), 3.99 (s, 3H), 3.87 (s, 6H), 3.80 (s, 3H).

Example 2: 0018

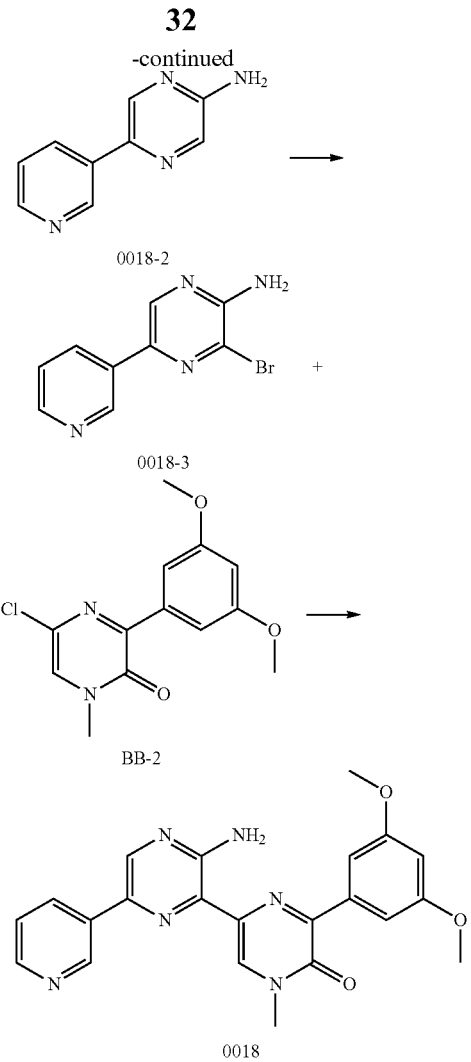

Synthetic Route:

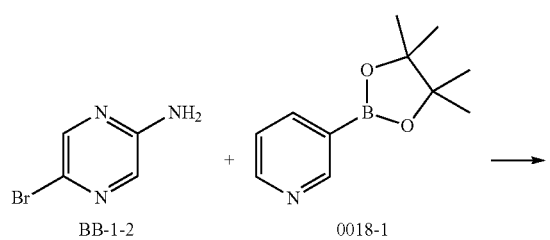

Step 1: Synthesis of Compound 0018-2

With regard to this step, reference can be made to the steps for synthesizing compounds BB-1-1 to BB-1-3, so as to obtain compound 0018-2. MS (ESI) m/z: 172.9 [M+H]$^+$.

$^1$H NMR (400 MHz, MeOH) δ: 9.07-9.01 (m, 1H), 8.49 (dd, 1H), 8.46 (d, 1H), 8.31 (m, 1H), 8.06 (d, 1H), 7.53-7.44 (m, 1H).

Step 2: Synthesis of Compound 0018-3

With regard to this step, reference can be made to the steps for synthesizing compounds 0017-2 to 0017-3, so as to obtain compound 0018-3. MS (ESI) m/z: 250.9 [M+H]$^+$.

Step 3: Synthesis of Compound 0018

Compound BB-2 (61 mg, 219.05 μmol, 1.1 eq) and bis(pinacolato)diboron (61 mg, 238.97 μmol, 1.2 eq) are dissolved in dioxane (3.0 mL), and palladium acetate (5 mg, 23.90 μmol, 0.12 eq), 2-dicyclohexylphosphono-2,4,6-triisopropylbiphenyl (23 mg, 47.79 μmol, 0.24 eq) and potassium acetate (59 mg, 597.41 μmol, 3 eq) are added. The air in the system is substituted with nitrogen three times, and the mixture is stirred at 100° C. for 30 minutes, and cooled to 25° C. Compound 0018-3 (50 mg, 199.14 μmol, 1 eq), a dichloromethane complex of [1,1'-bis(diphenylphosphino) ferrocene] palladium dichloride (18 mg, 21.91 μmol, 0.11 eq), potassium carbonate (83 mg, 597.41 μmol, 3 eq), dioxane (3.0 mL) and water (1.5 mL) are added. The air in the system is substituted with nitrogen three times, and the mixture is stirred at 100° C. for 8 hours. The reaction solution is directly concentrated. The obtained crude product is dissolved in methanol (5.0 mL), and the insoluble substance is filtered off. The filtrate is separated and purified by high-performance liquid chromatography (column: Boston Green ODS 150*30 mm 5 μm; mobile phase: [water (0.1% TFA)-ACN]; B %: 22%-48%, 7 minutes) to obtain the trifluoroacetate salt of compound 0018. The salt is dissolved in ethyl acetate, washed with saturated sodium bicarbonate, dried over anhydrous sodium sulfate and filtered, and the filtrate is concentrated to obtain compound 0018.

Trifluoroacetate salt of compound 0018: MS (ESI) m/z: 417.7 [M+H]+.

$^1$H NMR (400 MHz, DMSO-d$_6$) δ: 9.43 (m, 1H), 9.00 (s, 1H), 8.76 (s, 1H), 8.70 (m, 1H), 8.65 (m, 1H), 7.67 (m, 1H), 7.46 (d, 2H), 6.67 (t, 1H), 3.82 (s, 6H), 3.77 (s, 3H).

Example 3: 0023

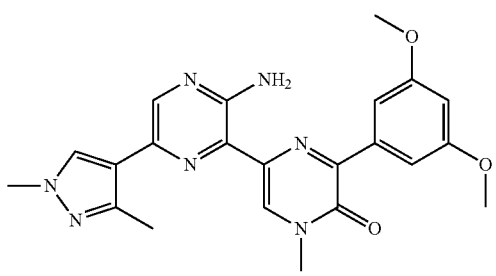

0023

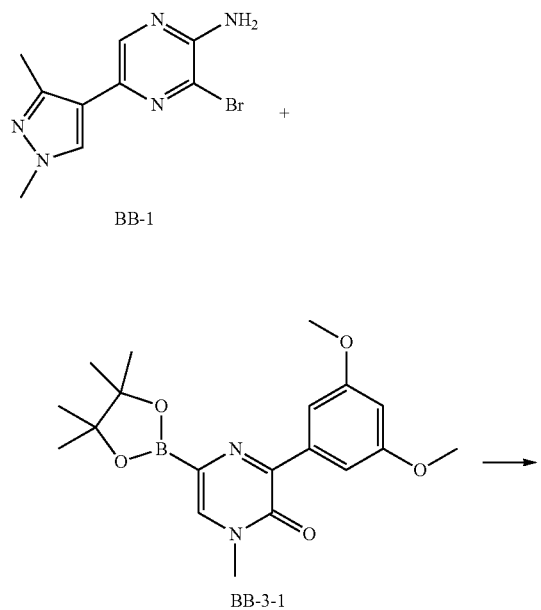

BB-1

BB-3-1

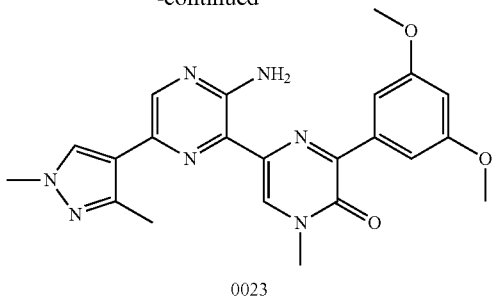

0023

Step 1: Synthesis of Compound 0023

Compound BB-3-1 (100 mg, 268.66 μmol, 1 eq) is added to dioxane (2.0 mL) and water (1.0 mL), and then compound BB-1 (72 mg, 268.66 μmol, 1 eq), tetratriphenylphosphine palladium (31 mg, 26.87 μmol, 0.1 eq) and potassium carbonate (111 mg, 805.97 μmol, 3 eq) are added. The reaction solution is reacted at 100° C. for 3 hours. The reaction solution is added with ethyl acetate (50.0 mL), washed with saturated brine (20.0 mL) once, dried over anhydrous sodium sulfate and filtered, and the filtrate is concentrated to obtain a crude black solid. The crude product is separated and purified by high-performance liquid chromatography (column: YMC-Actus Triart C18 100*30 mm*5 μm; mobile phase: [water (0.05% HCl)-ACN]; B %: 40%-70%, 10 minutes) to obtain the hydrochloride salt of compound 0023. The salt is dissolved in ethyl acetate, washed with saturated sodium bicarbonate, dried over anhydrous sodium sulfate and filtered, and the filtrate is concentrated to obtain compound 0023.

Hydrochloride salt of compound 0023: MS (ESI) m/z: 433.8 [M+H]+.

$^1$H NMR (400 MHz, MeOH) δ: 8.88 (s, 1H) 8.29 (s, 1H) 7.98 (s, 1H) 7.39 (s, 2H) 6.67 (s, 1H) 3.95 (s, 3H) 3.87 (s, 6H) 3.83 (s, 3H), 2.57 (s, 3H).

Example 4: 0027

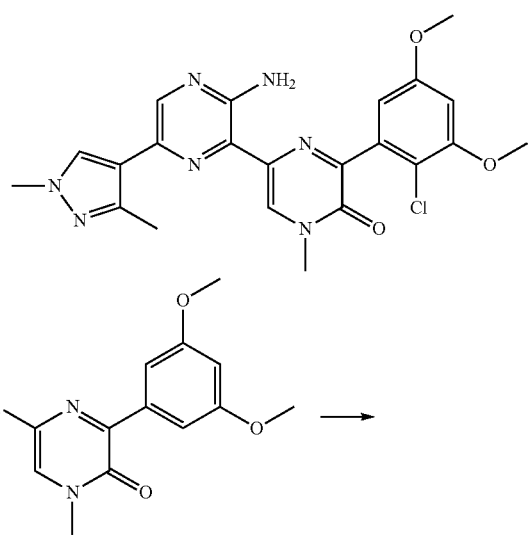

0027

BB-2

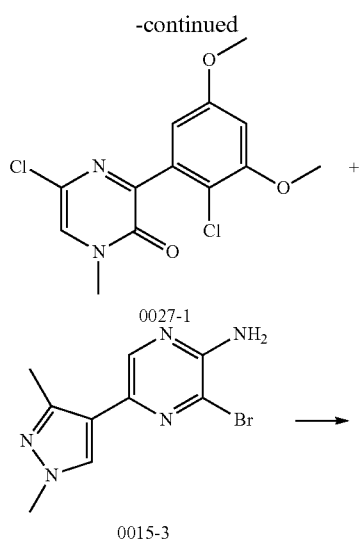

Step 1: Synthesis of Compound 0027-1

Under nitrogen protection, compound BB-2 (250 mg, 890.61 μmol, 1 eq) is dissolved in a mixed solvent of acetonitrile (20.0 mL) and dichloromethane (5.0 mL). A solution of sulfonyl chloride (84 mg, 623.43 μmol, 62.33 μL, 0.7 eq) in acetonitrile (2.5 mL) is slowly added dropwise at 0° C., and the mixture is stirred at 0° C. for 10 minutes. The reaction solution is added with methanol (5.0 mL) to quench the reaction, and concentrated to dryness under reduced pressure. The crude product is separated by column chromatography (petroleum ether:ethyl acetate=1:0 to 1:1) (TLC detection petroleum ether:ethyl acetate=1:1) to obtain compound 0027-1. MS (ESI) m/z: 314.9 [M+H]⁺.

Step 2: Synthesis of Compound 0027

In a three-necked flask, compound 0027-1 (59 mg, 186.49 μmol, 1 eq), bis(pinacolato)diboron (52 mg, 205.14 μmol, 1.1 eq), palladium acetate (5 mg, 20.51 μmol, 0.11 eq), 2-dicyclohexylphosphono-2,4,6-triisopropylbiphenyl (20 mg, 41.03 μmol, 0.22 eq) and potassium acetate (60 mg, 615.42 μmol, 3.3 eq) are added to dioxane (4.0 mL) solution. The air in the reaction system is substituted with nitrogen, and under nitrogen saturation, the solution is heated to 100° C. to reflux and stirred for 30 minutes, and cooled to 25° C. Compound 0015-3 (50 mg, 186.49 μmol, 1 eq), a dichloromethane complex of [1,1'-bis(diphenylphosphino)ferrocene] palladium dichloride (15 mg, 18.65 μmol, 0.1 eq), potassium carbonate (77 mg, 559.47 μmol, 3 eq), dioxane (4.0 mL) and water (2.0 mL) are added. The air in the reaction system is substituted with nitrogen, and under nitrogen saturation, the solution is heated to 100° C. to reflux and stirred for 8 hours. The reaction solution is directly concentrated. The obtained crude product is separated and purified by high-performance liquid chromatography (chromatographic column: Boston Green ODS150×30 mm 5 μm; mobile phase: [water (0.1% TFA)-ACN]; B %: 30%-60%, 8 minutes) to obtain the trifluoroacetate salt of compound 0027. The salt is dissolved in ethyl acetate, washed with saturated sodium bicarbonate, dried over anhydrous sodium sulfate and filtered, and the filtrate is concentrated to obtain compound 0027.

Trifluoroacetate salt of compound 0027: MS (ESI) m/z: 468.2 [M+H]⁺.

¹H NMR (400 MHz, MeOH) δ: 8.79 (s, 1H), 8.09 (m, 2H), 6.76 (m, 2H), 3.93 (s, 3H), 3.89 (s, 3H), 3.84 (s, 3H), 3.80 (s, 3H), 2.54 (s, 3H).

Example 5: 0029

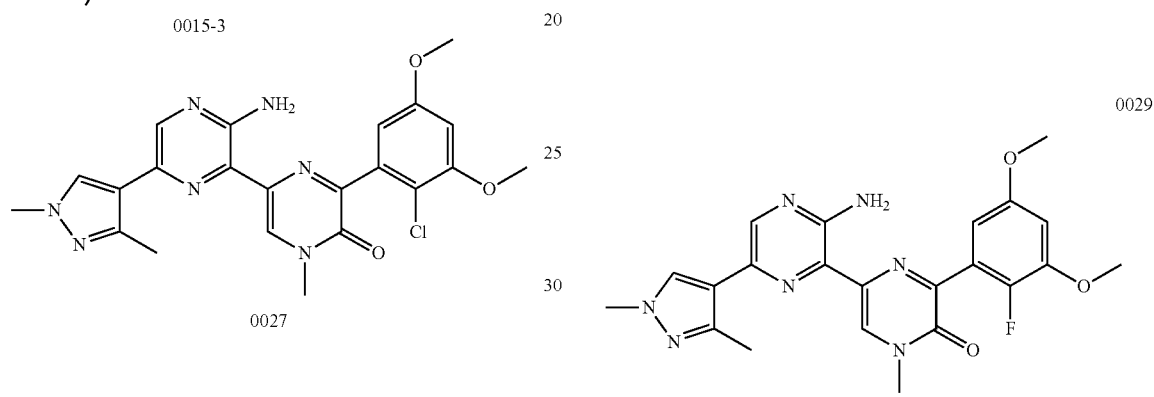

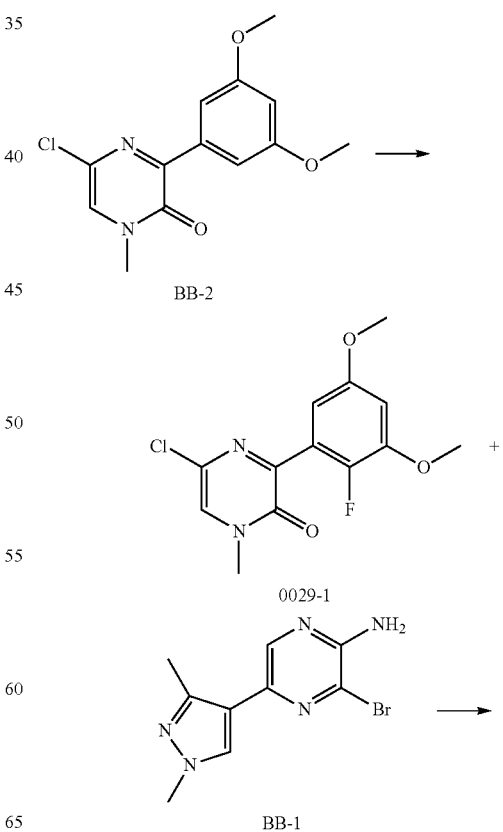

Example 6: 0033

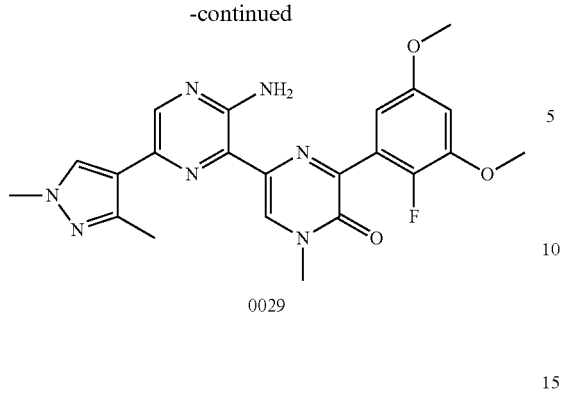
0029

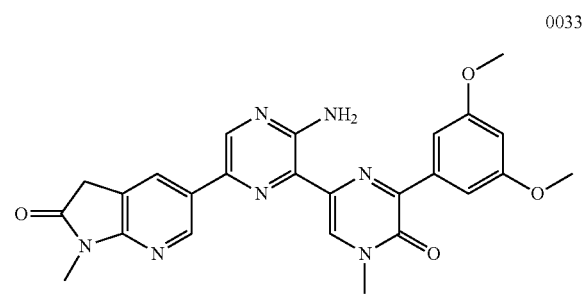 [SMILES: COc1cc(OC)cc(-c2nc(-c3nc(-c4cnc5c(c4)CC(=O)N5C)cnc3N)cn(C)c2=O)c1]
0033

Step 1: Synthesis of Compound 0029-1

Compound BB-2 (600 mg, 2.14 mmol, 1 eq) is added to acetonitrile (10.0 mL) at 0° C., and then 1-chloromethyl-4-fluoro-1,4-diazabicyclo[2.2.2] octane bis(tetrafluoroborate) salt (833 mg, 2.35 mmol, 1.1 eq) is added, and the reaction solution is reacted at 20° C. for 2 hours. The reaction solution is subjected to rotary evaporation to obtain a crude yellow solid. The crude product is separated by column chromatography (dichloromethane:ethyl acetate=1:0 to 10:1) (TLC detection dichloromethane:ethyl acetate=10:1) to obtain compound 0029-1. MS (ESI) m/z: 299.0 [M+H]$^+$.

Step 2: Synthesis of Compound 0029

Compound 0029-1 (800 mg, 267.83 μmol, 1 eq) is added to dioxane (3.0 mL), and then bis(pinacolato)diboron (95 mg, 374.96 μmol, 1.4 eq), potassium acetate (79 mg, 803.49 μmol, 3 eq), tris(dibenzylideneacetone) dipalladium (25 mg, 26.78 μmol, 0.10 eq) and tricyclohexylphosphine (11 mg, 40.17 μmol, 13.02 μL, 0.15 eq) are added. The reaction solution is reacted at 100° C. for 30 minutes under nitrogen protection, and cooled to 25° C., and then potassium carbonate (74 mg, 535.66 μmol, 2 eq), compound BB-1 (72 mg, 267.83 μmol, 1 eq), a dichloromethane complex of [1,1'-bis(diphenylphosphino)ferrocene] palladium dichloride (22 mg, 26.78 μmol, 0.1 eq) and water (2.0 mL) are added. The air in the system is substituted with nitrogen three times, and the reaction solution is reacted at 100° C. for 16 hours under nitrogen protection. The reaction solution is added with ethyl acetate (50.0 mL), washed with saturated brine (25.0 mL, 25.0 mL) twice, dried over anhydrous sodium sulfate and filtered, and the filtrate is concentrated to obtain a crude product. The obtained crude product is separated and purified by high-performance liquid chromatography (chromatographic column: Boston Green ODS 150*30 mm 5 μm; mobile phase: [water (0.1% TFA)-ACN]; B %: 35% to 61.25%, 7 minutes) to obtain the trifluoroacetate salt of compound 0029. The salt is dissolved in ethyl acetate, washed with saturated sodium bicarbonate, dried over anhydrous sodium sulfate and filtered, and the filtrate is concentrated to obtain compound 0029.

Trifluoroacetate salt of compound 0029: MS (ESI) m/z: 452.0 [M+H]$^+$.

$^1$H NMR (400 MHz, MeOH) δ: 8.67 (s, 1H) 8.19 (s, 1H), 8.14 (s, 1H) 6.82-6.86 (m, 2H) 3.87 (s, 3H), 3.79 (s, 3H), 3.77 (s, 3H), 3.69 (s, 3H) 2.43 (s, 3H).

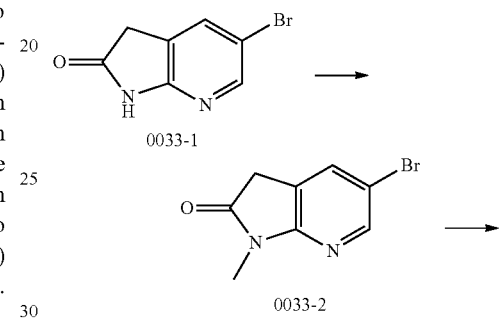
0033-1

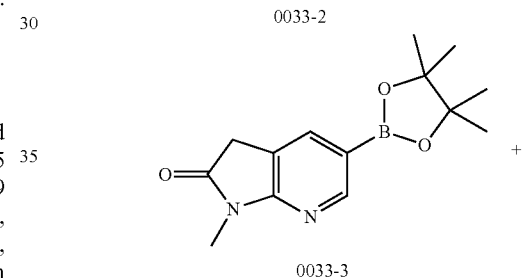
0033-2

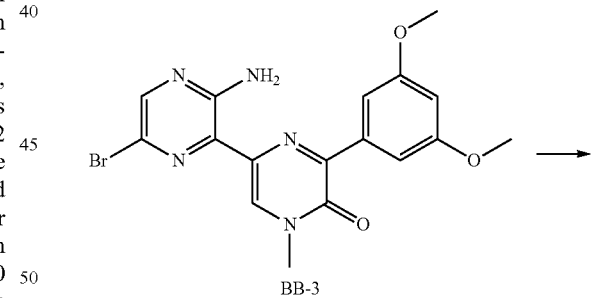
0033-3

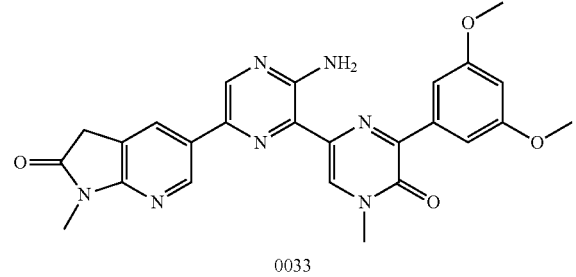
0033

Step 1: Synthesis of Compound 0033-2

Compound 0033-1 (2.0 g, 9.39 mmol, 1 eq) is dissolved in toluene (24.0 mL), methanol (45.0 mL) and tetrahydrofuran (10.0 mL), cooled to 0° C. and slowly added with a solution of trimethylsilazodimethane in n-hexane (2 M, 18.8 mL, 4 eq), and the solution is continued to react at 0° C. for 1 hour, and then heated to 20° C. and reacted for 22 hours. The reaction solution is directly subjected to rotary evaporation under reduced pressure distillation to obtain a crude product. The crude product is separated by column chromatography (petroleum ether:ethyl acetate=1:0 to 30:1) (TLC detection petroleum ether:ethyl acetate=10:1) to obtain compound 0033-2.

MS (ESI) m/z: 226.9 [M+H]⁺.

Step 2: Synthesis of Compound 0033-3

Compound 0033-2 (150 mg, 660.63 μmol, 1 eq), bis (pinacolato)diboron (252 mg, 990.94 μmol, 1.5 eq), tris (dibenzylideneacetone)dipalladium (30 mg, 33.03 μmol, 0.05 eq), tricyclohexylphosphine (19 mg, 66.06 μmol, 21.42 μL, 0.1 eq) and potassium acetate (1945 mg, 1.98 mmol, 3 eq) are dissolved in dioxane (4.0 mL), and the mixed solution is heated to 90° C. and reacted for 16 hours under nitrogen protection. The reaction solution is added with water (10.0 mL), and extracted with ethyl acetate (10.0 mL×3). The organic phases are combined, dried over anhydrous sodium sulfate, and filtered, and the filtrate is subjected to rotary evaporation under reduced pressure distillation to obtain a crude product. The crude product is separated and purified by a preparation plate (petroleum ether:ethyl acetate:ethanol=7:3:1) to obtain compound 0033-3. MS (ESI) m/z: 275.0 [M+H]⁺.

Step 3: Synthesis of Compound 0033

With regard to this step, reference can be made to the steps for synthesizing compounds BB-1 to 0023, so as to obtain the crude product of compound 0033. The crude product is separated and purified by high-performance liquid chromatography (column: YMC-Actus Triart C18 100*30 mm*5 μm; mobile phase: [water (0.05% HCl)-ACN]; B %: 50-74%, 7.5 minutes) to obtain the hydrochloride salt of compound 0033. The salt is dissolved in ethyl acetate, washed with saturated sodium bicarbonate, dried over anhydrous sodium sulfate and filtered, and the filtrate is concentrated to obtain compound 0033.

Hydrochloride salt of compound 0033: MS (ESI) m/z: 486.1 [M+H]⁺.

1H NMR (400 MHz, DMSO-d₆) δ: 8.92 (m, 2H), 8.62 (s, 1H), 8.36 (s, 1H), 7.44 (d, 2H), 6.65 (t, 1H), 3.81 (s, 6H), 3.76 (s, 3H), 3.69 (s, 2H), 2.54 (s, 3H).

Example 7: 0036

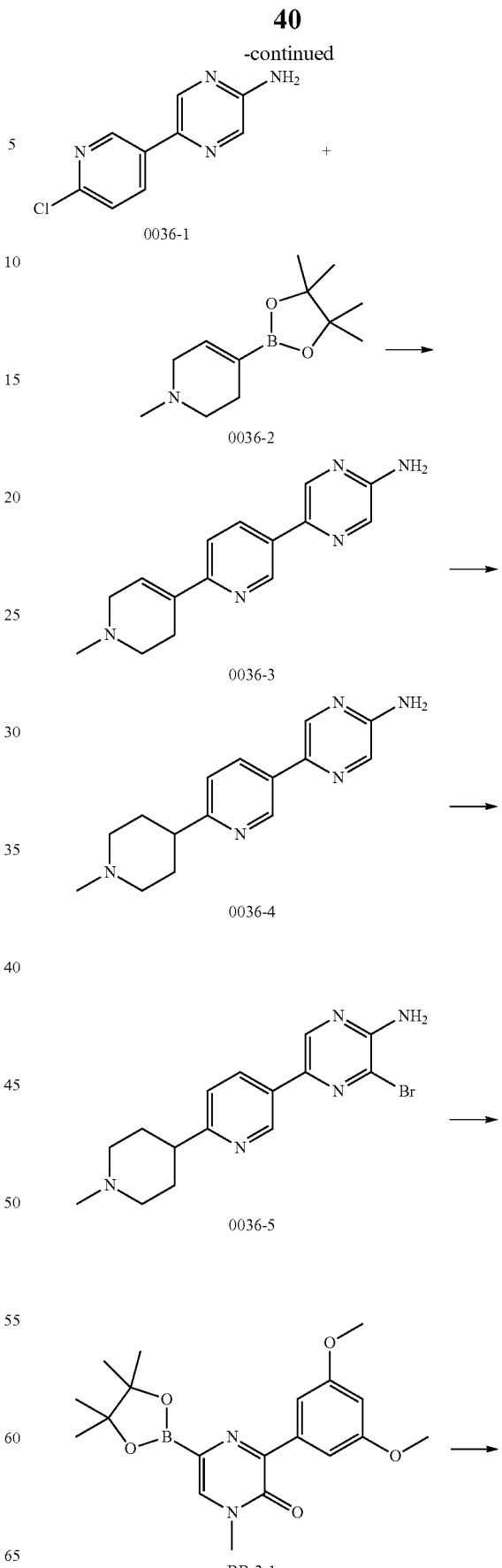

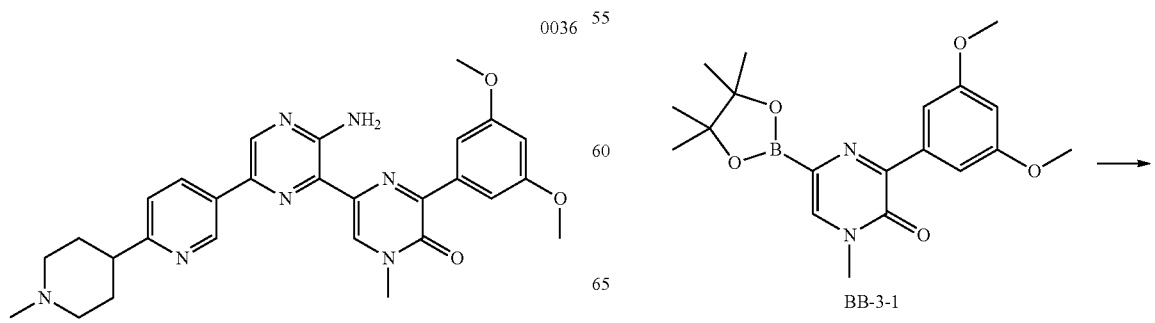

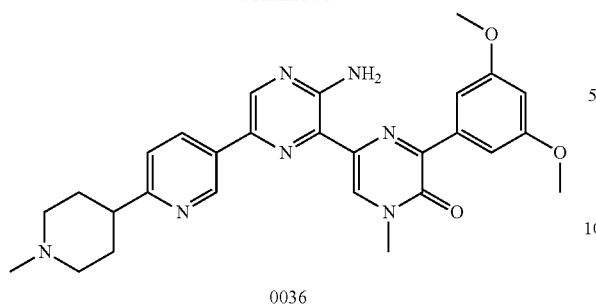

0036

Step 1: Synthesis of Compound 0036-3

With regard to this step, reference can be made to the steps for synthesizing compounds BB-1 to 0023, so as to obtain compound 0036-3. MS (ESI) m/z: 267.9 [M+H]⁺.

Step 2: Synthesis of Compound 0036-4

Wet palladium carbon (80 mg, purity: 10%) is dissolved in methanol (50.0 mL), and compound 0036-3 (500 mg, 1.87 mmol, 1 eq) is added. The reaction solution is reacted at 20° C. for 3 hours under a hydrogen pressure of 40 psi in a hydrogenation bottle. The reaction solution is filtered, and the filtrate is directly subjected to rotary evaporation under reduced pressure distillation to obtain compound 0036-4. MS (ESI) m/z: 270.0 [M+H]⁺.

Step 3: Synthesis of Compound 0036-5

With regard to this step, reference can be made to the steps for synthesizing compounds BB-4-6 to BB-4, so as to obtain compound 0036-5. MS (ESI) m/z: 347.9 [M+H]⁺.

Step 4: Synthesis of Compound 0036

With regard to this step, reference can be made to the steps for synthesizing compounds BB-1 to 0023, so as to obtain the crude product of compound 0036. The crude product is separated and purified by high-performance liquid chromatography (column: YMC-Actus Triart C18 100*30 mm*5 μm; mobile phase: [water (0.05% HCl)-ACN]; B %: 35%-65%, 9 minutes) to obtain the hydrochloride salt of compound 0036. The salt is dissolved in ethyl acetate, washed with saturated sodium bicarbonate, dried over anhydrous sodium sulfate and filtered, and the filtrate is concentrated to obtain compound 0036.

Hydrochloride salt of compound 0036: MS (ESI) m/z: 514.1 [M+H]⁺.

¹H NMR (400 MHz, DMSO-d₆) δ: 10.14 (m, 1H), 9.35 (d, 1H), 8.98 (s, 1H), 8.76-8.69 (m, 1H), 8.60 (m, 1H), 7.51 (m, 1H), 7.46 (d, 2H), 6.67 (t, 1H), 3.82 (s, 6H), 3.77 (s, 3H), 3.17-3.04 (m, 3H), 2.86-2.78 (m, 3H), 2.68 (s, 1H), 2.34 (s, 1H), 2.13 (m, 4H).

Example 8: 0060

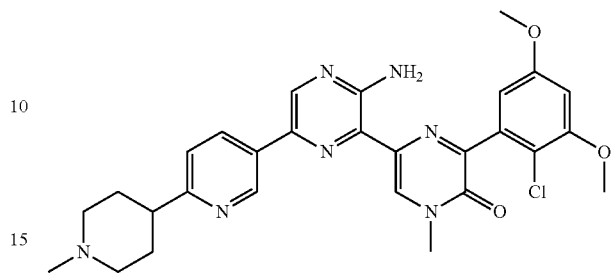

0060

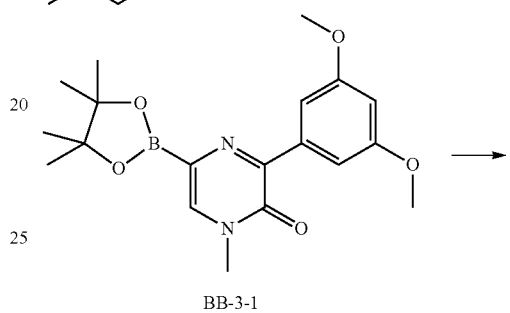

BB-3-1

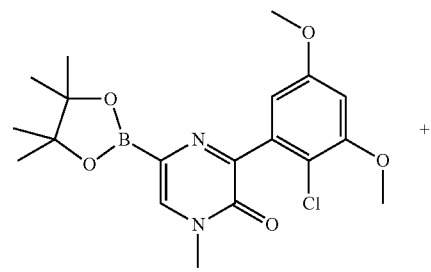

0060-1

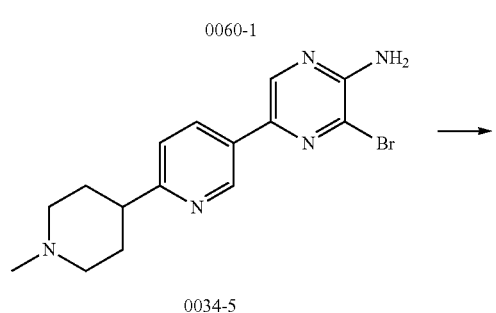

0034-5

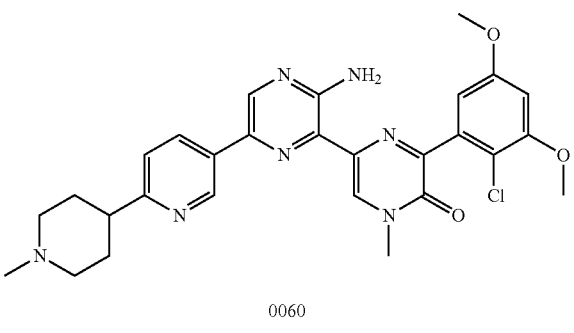

0060

43

Step 1: Synthesis of Compound 0060-1

With regard to this step, reference can be made to the steps for synthesizing compounds BB-2 to 0027-1, so as to obtain compound 0060-1. MS (ESI) m/z: 324.9 [M+H]$^+$.

Step 2: Synthesis of Compound 0060

With regard to this step, reference can be made to the steps for synthesizing compounds BB-1 to 0023, so as to obtain the crude product of compound 0060. The crude product is separated and purified by high-performance liquid chromatography (column: Boston Green ODS 150*30 5 μm; mobile phase: [water (0.1% TFA)-ACN]; B %: 12%-42%, 8 minutes) to obtain the trifluoroacetate salt of compound 0060. The salt is dissolved in ethyl acetate, washed with saturated sodium bicarbonate, dried over anhydrous sodium sulfate and filtered, and the filtrate is concentrated to obtain compound 0060.

Trifluoroacetate salt of compound 0060: MS (ESI) m/z: 548.1 [M+H]$^+$.

$^1$H NMR (400 MHz, MeOH) δ: (d, 1H), 8.92 (s, 1H), 8.53 (m, 2H), 7.53 (d, 1H), 6.78 (d, 1H), 6.74 (d, 1H), 3.93 (s, 3H), 3.85 (s, 3H), 3.82 (s, 3H), 3.68 (m, 2H), 3.26-3.12 (m, 3H), 2.95 (s, 3H), 2.31-2.22 (m, 2H), 2.20-2.08 (m, 2H).

Examples 9 and 10: 0048 and 0049

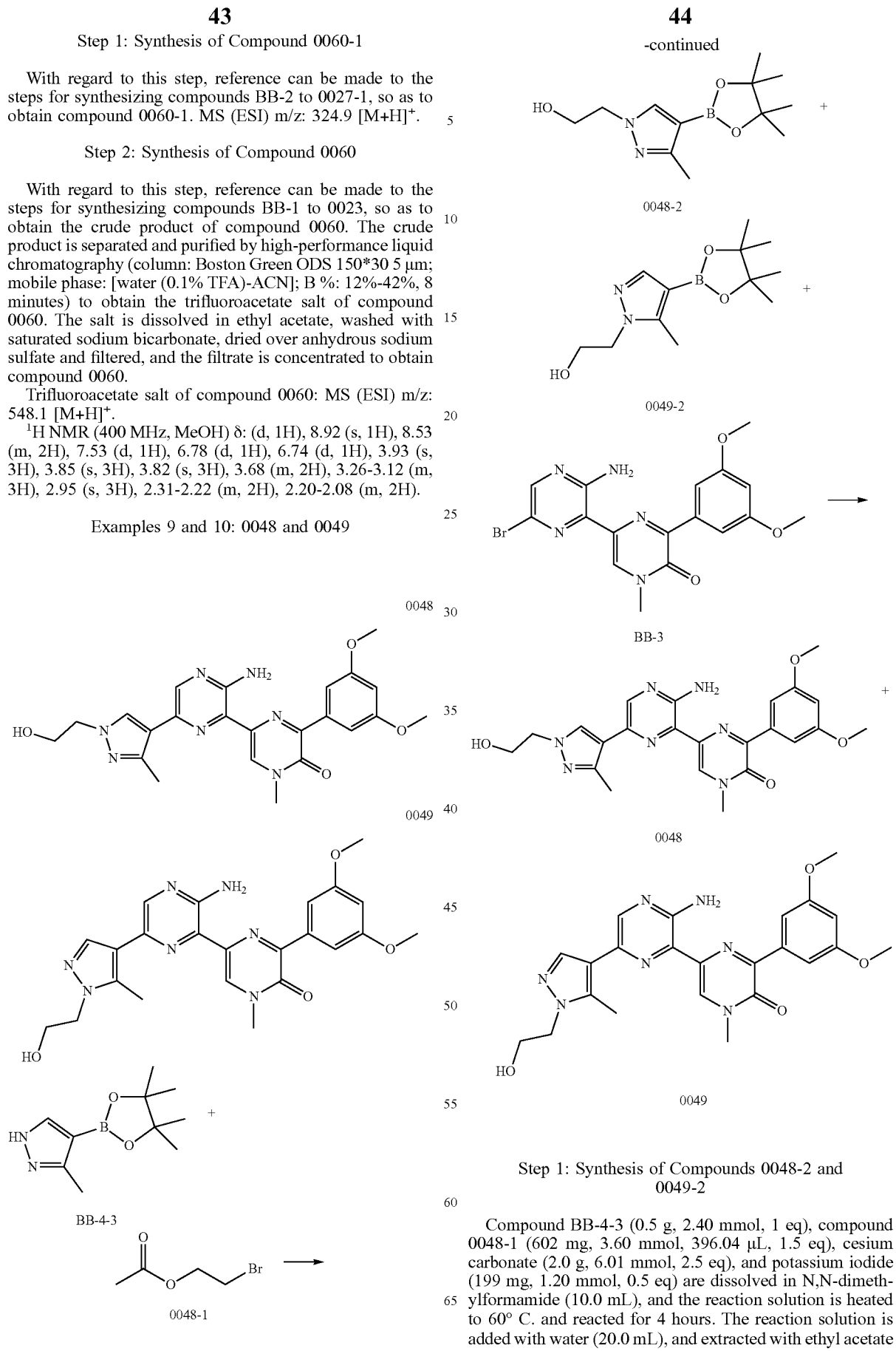

Step 1: Synthesis of Compounds 0048-2 and 0049-2

Compound BB-4-3 (0.5 g, 2.40 mmol, 1 eq), compound 0048-1 (602 mg, 3.60 mmol, 396.04 μL, 1.5 eq), cesium carbonate (2.0 g, 6.01 mmol, 2.5 eq), and potassium iodide (199 mg, 1.20 mmol, 0.5 eq) are dissolved in N,N-dimethylformamide (10.0 mL), and the reaction solution is heated to 60° C. and reacted for 4 hours. The reaction solution is added with water (20.0 mL), and extracted with ethyl acetate (20.0 mL×3). The organic phases are combined, dried over anhydrous sodium sulfate, and filtered, and the filtrate is subjected to rotary evaporation under reduced pressure distillation to obtain a mixture of compounds 0048-2 and 0049-2. MS (ESI) m/z: 3253.0 [M+H]+.

Step 2: Synthesis of Compounds 0048 and 0049

With regard to this step, reference can be made to the steps for synthesizing compounds BB-1 to 0023, so as to obtain a mixture of compounds 0048 and 0049. The mixture is then subjected to chiral resolution (column: DAICEL CHIRALPAK AS-H (250 mm×30 mm, 5 μm); mobile phase: [0.1% NH$_3$H$_2$O EtOH]; B %: 30-30%, minutes) to obtain compound 0048 (retention time: 3.87 minutes) and compound 0049 (retention time: 4.11 minutes).

MS (ESI) m/z: 464.0 [M+H]+.

0048: $^1$H NMR (400 MHz, DMSO-d$_6$) δ: 8.67 (s, 1H), 8.20 (d, 2H), 7.46 (s, 2H), 7.38 (s, 1H), 7.31-7.28 (s, 1H), 6.65 (t, 1H), 4.96 (s, 1H), 4.10 (t, 2H), 3.81 (s, 6H), 3.76 (t, 2H), 3.72 (s, 3H), 2.45 (s, 3H).

0049: $^1$H NMR (400 MHz, DMSO-d$_6$) δ: 8.62 (s, 1H), 8.23 (s, 1H), 7.91 (s, 1H), 7.45 (d, 2H), 7.38 (s, 2H), 6.64 (t, 1H), 5.00 (s, 1H), 4.14 (t, 2H), 3.80 (s, 6H), 3.77-3.72 (t, 2H), 3.71 (s, 3H), 2.57 (s, 3H).

Examples 11 and 12: 0043, 0051

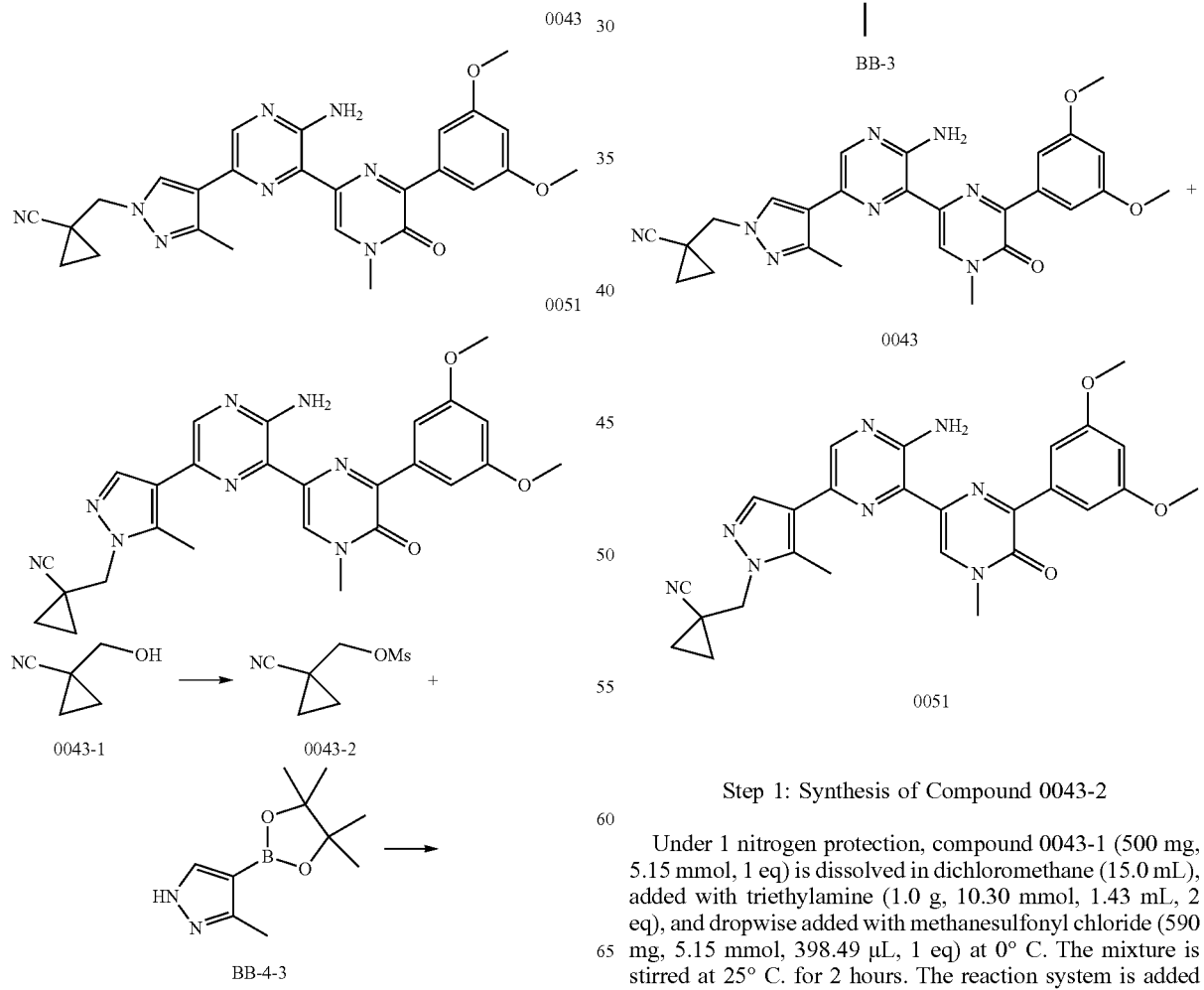

Step 1: Synthesis of Compound 0043-2

Under 1 nitrogen protection, compound 0043-1 (500 mg, 5.15 mmol, 1 eq) is dissolved in dichloromethane (15.0 mL), added with triethylamine (1.0 g, 10.30 mmol, 1.43 mL, 2 eq), and dropwise added with methanesulfonyl chloride (590 mg, 5.15 mmol, 398.49 μL, 1 eq) at 0° C. The mixture is stirred at 25° C. for 2 hours. The reaction system is added with water (20.0 mL) to quench the reaction, and extracted for layer separation, and at the same time, the organic phase is extracted three times with water (5.0 mL×3). The organic phases are combined and washed once with saturated sodium chloride solution (10.0 mL); finally, the organic phase is dried over anhydrous sodium sulfate, filtered and concentrated under reduced pressure to obtain compound 0043-2.

Step 2: Synthesis of Compound 0043-3

Under nitrogen protection, compound 0043-2 (200 mg, 1.14 mmol, 1 eq) and compound BB-4-3 (238 mg, 1.14 mmol, 1 eq) are dissolved in N,N-dimethylformamide (5.0 mL), and cesium carbonate (744 mg, 2.28 mmol, 2 eq) is added. The mixture is stirred at 100° C. for 2 hours and 30 minutes. The reaction solution is diluted with ethyl acetate (100.0 mL) and washed with water (10.0 mL×5). The organic phases are combined and washed once with saturated sodium chloride solution (50.0 mL); finally, the organic phase is dried over anhydrous sodium sulfate, filtered and concentrated under reduced pressure to obtain a mixture of compound 0043-3 and compound 0051-3. MS (ESI) m/z: 288.4 [M+H]$^+$.

Step 3: Synthesis of Compounds 0043 and 0051

With regard to this step, reference can be made to the steps for synthesizing compounds BB-1 to 0023, so as to obtain a mixture of compound 0043 and compound 0051. The mixture is then subjected to chiral resolution (column: DAICEL CHIRALPAK AS-H (250 mm*30 mm, 5 μm); mobile phase: [0.1% NH$_3$H$_2$O EtOH]; B %: 40%-40%, minutes) to obtain compound 0043 (retention time: 3.97 minutes) and compound 0051 (retention time: 4.315 minutes). MS (ESI) m/z: 499.2 [M+H]$^+$.

0043: $^1$H NMR (400 MHz, CHCl$_3$) δ: 8.47 (s, 1H), 8.49-8.45 (s, 1H), 7.91 (s, 1H), 7.52-7.46 (d, 2H), 6.62-6.60 (m, 3H), 4.21 (s, 2H), 3.89-3.84 (s, 6H), 3.77 (s, 3H), 2.54 (s, 3H), 1.43-1.38 (m, 2H), 1.30-1.24 (m, 2H).

0051: $^1$H NMR (400 MHz, CHCl$_3$) δ: 8.44 (s, 1H), 8.17 (s, 1H), 7.84 (s, 1H), 7.49 (d, 2H), 6.70 (s, 2H), 6.61 (t, 1H), 4.28 (s, 2H), 3.87 (s, 6H), 3.78 (s, 3H), 2.71 (s, 3H), 1.45-1.28 (m, 4H).

Example 13: 0056

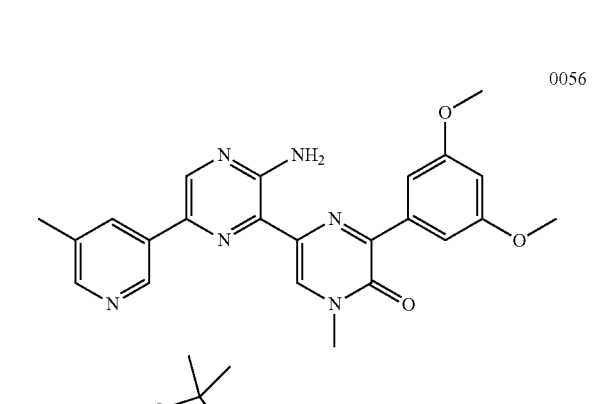

0056-1

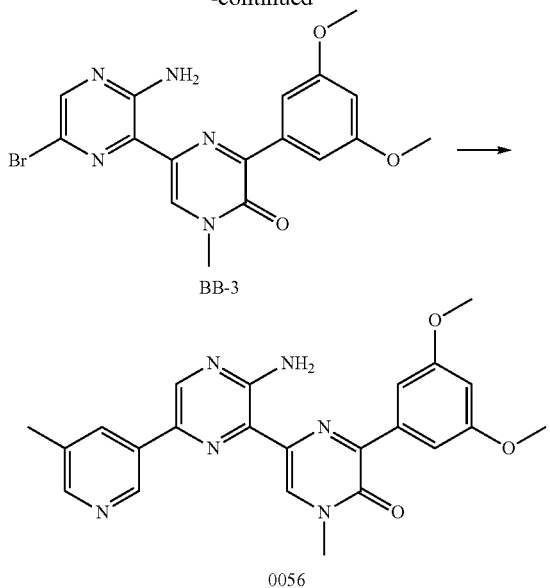

BB-3

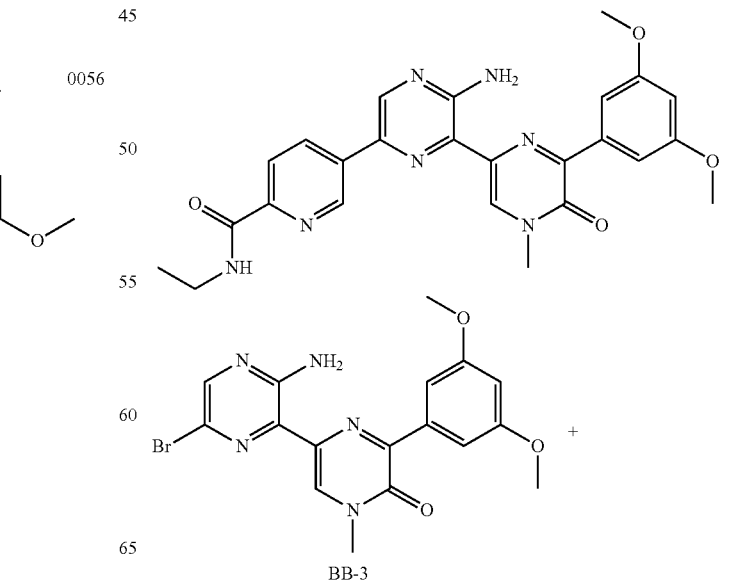

0056

Step 1: Synthesis of Compound 0056

With regard to this step, reference can be made to the steps for synthesizing compounds BB-1 to 0023, so as to obtain the crude product of compound 0056. The crude product is dissolved in dichloromethane (1 mL), and separated and purified by a preparation plate (dichloromethane:methanol=15:1) to obtain compound 0056. MS (ESI) m/z: 431.0 [M+H]$^+$.

$^1$H NMR (400 MHz, CHCl$_3$) δ: 9.02 (s, 1H), 8.58 (s, 1H), 8.49-8.43 (m, 2H), 7.99 (s, 1H), 7.50 (d, 2H), 6.63 (t, 1H), 3.88 (s, 6H), 3.82 (s, 3H), 3.50 (s, 2H), 2.46 (s, 3H).

Example 14: 0038

-continued

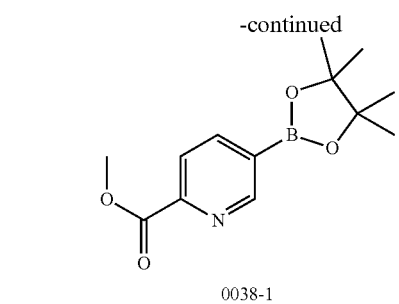

0038-1

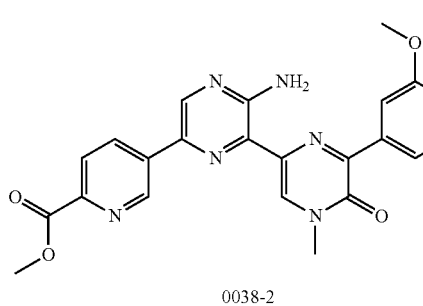

0038-2

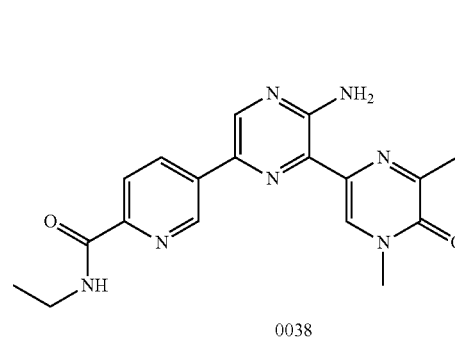

0038

Step 1: Synthesis of Compound 0038-2

Compound BB-3 (20 mg, 47.82 μmol, 1 eq), potassium phosphate (20 mg, 95.64 μmol, 2 eq), tetratriphenylphosphine palladium (1 mg, 9.564 μmol, 0.2 eq) and 0038-1 (25.16 mg, 95.64 μmol, 2 eq) are dissolved in dioxane (5.0 mL), and reacted at 100° C. for 8 hours under nitrogen protection. Water (3.0 mL) is added, there being a solid precipitated, and compound 0038-2 is obtained by suction filtration. MS (ESI) m/z: 475.1 [M+H]+.

Step 2: Synthesis of Compound 0038

Compound 0038-2 (13 mg, 27.40 μmol, 2.80 mL, 1 eq) and ethylamine (25 mg, 547.98 μmol, 35.86 μL, 20 eq) are dissolved in ethanol (20.0 mL), and reacted at 25° C. for 2 hours under nitrogen protection. Compound 0038 is separated and obtained by concentration under reduced pressure. MS (ESI) m/z: 488.0 [M+H]+.

$^1$H NMR (400 MHz, DMSO-$d_6$) δ: 9.43 (s, 1H), 9.05 (s, 1H), 8.87 (m, 1H), 8.82-8.73 (m, 1H), 8.16 (d, 1H), 7.52 (d, 2H), 6.73 (t, 1H), 3.88 (s, 6H), 3.83 (s, 3H), 2.64-2.61 (m, 2H), 1.22 (s, 3H).

Examples 15 and 16: 0046 and 0045

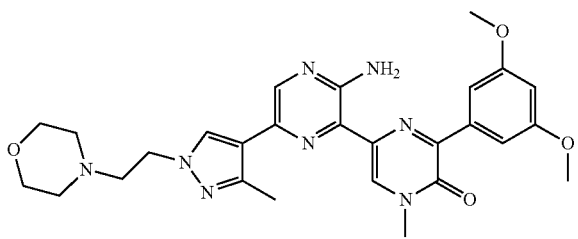

0046

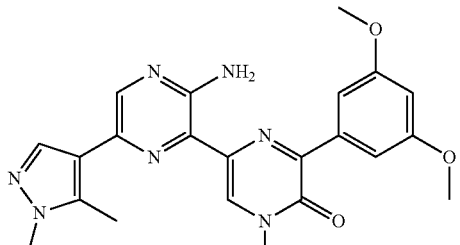

0045

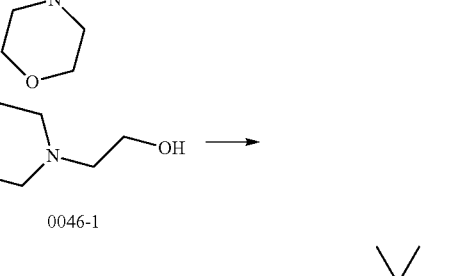

0046-1

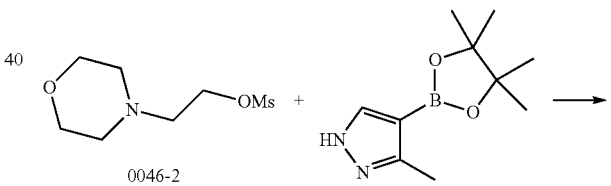

0046-2     0046-3

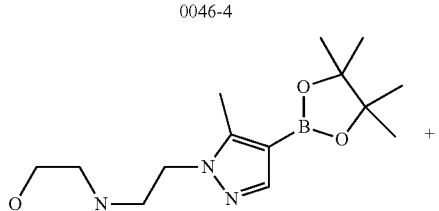

0046-4

0045-4

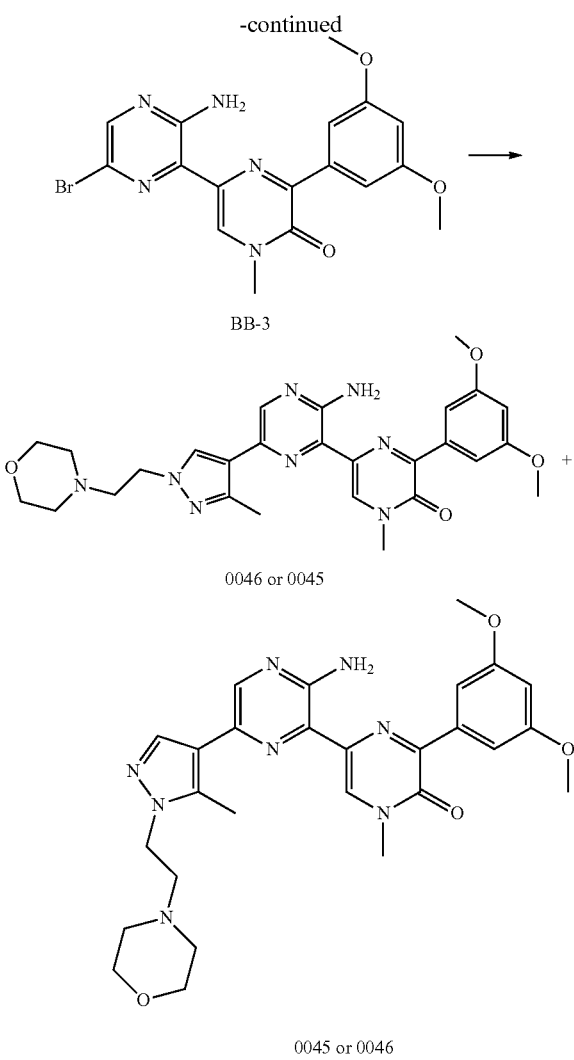

Step 1: Synthesis of Compound 0046-2

With regard to this step, reference can be made to the steps for synthesizing compounds 0043-1 to 0043-2, so as to obtain compound 0046-2.

Step 2: Synthesis of Compound 0046-4

Compound 0046-3 (3.0 g, 14.42 mmol, 1 eq), cesium carbonate (23.4 g, 72.09 mmol, 5 eq) and compound 0046-2 (3.6 g, 17.30 mmol, 1.2 eq) are dissolved in N,N-dimethylformamide (30.0 mL), and reacted at 160° C. for 2 hours under nitrogen protection. The reaction solution is subjected to suction filtration, added with water (50.0 mL), and then extracted by adding ethyl acetate (50.0 mL). The organic phase is dried over anhydrous sodium sulfate, subjected to suction filtration, and concentrated to obtain a mixture of compound 0046-4 and compound 0045-4. MS (ESI) m/z: 322.1 [M+H]⁺.

Step 3: Synthesis of Compounds 0046 and 0045

Compound BB-3 (60.0 mg, 143.46 μmol, 1 eq), potassium phosphate (61 mg, 286.91 μmol, 2 eq), tetratriphenylphosphine palladium (33 mg, 28.69 μmol, 0.2 eq) and a mixture of compound 0046-4 and compound 0045-4 (92 mg, 286.91 μmol, 2 eq) are dissolved in dioxane (5.0 mL), and reacted at 100° C. for 8 hours under nitrogen protection. The solution is concentrated under reduced pressure to obtain a crude product, which is separated by high-performance liquid chromatography to obtain a mixture of compound 0046 and compound 0045. Finally, the mixture is subjected to chiral resolution (column: Chiralpak AS-H 150*4.6 mm I.D., 5 μm, mobile phase: A: CO₂ B: ethanol (0.05% DEA); gradient: 5% (B)—0.5 minutes, 5% to 40% (B)—3.5 minutes, 40% (B)—2.5 minutes, 5% (B)—1.5 minutes; flow rate: 3 mL/min; column temperature: 40° C.) to obtain compound 0046 (retention time: 3.87 minutes) and compound 0045 (retention time: 4.11 minutes). MS (ESI) m/z: 533.1 [M+H]⁺.

0046: $^1$H NMR (400 MHz, DMSO-d₆) δ: 8.84-8.67 (m, 1H), 8.34-8.19 (m, 2H), 7.61-7.38 (m, 3H), 6.77-6.67 (m, 1H), 4.23 (m, 2H), 3.87 (s, 6H), 3.77 (s, 3H), 3.66-3.55 (m, 3H), 3.66-3.55 (m, 1H), 2.79 (t, 2H), 2.51 (s, 7H).

0045: $^1$H NMR (400 MHz, DMSO-d₆) δ: 8.71-8.61 (m, 1H), 8.28-8.20 (m, 1H), 7.97-7.87 (m, 1H), 7.52-7.34 (m, 4H), 6.70-6.63 (m, 1H), 4.22 (m, 2H), 3.81 (s, 6H), 3.72 (s, 3H), 3.60-3.54 (m, 4H), 2.72-2.67 (m, 2H), 2.63-2.59 (m, 2H), 2.44 (m, 5H).

Example 17: 0028

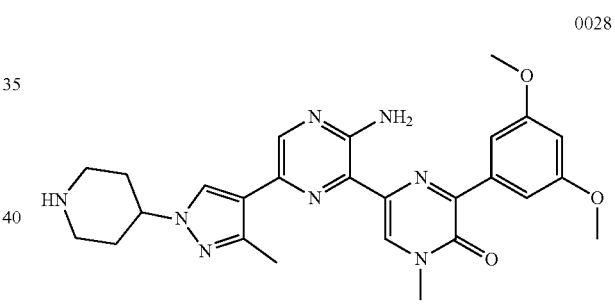

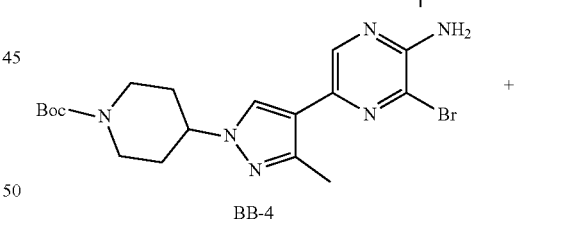

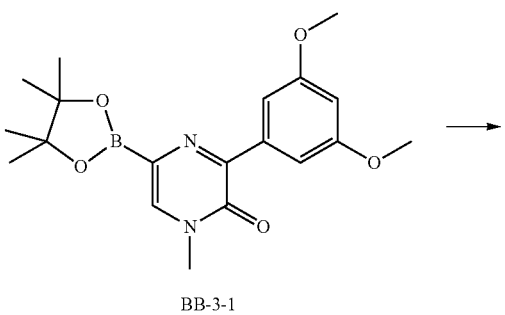

53

-continued

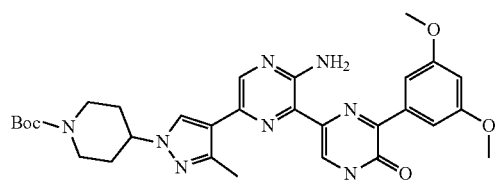

0028-1

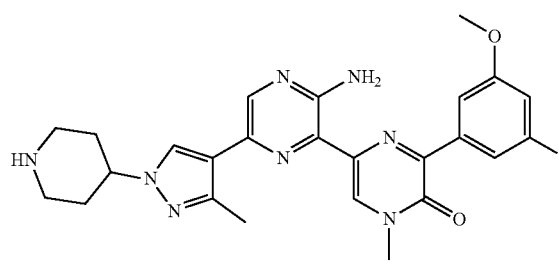

0028

Step 1: Synthesis of Compound 0028-1

With regard to this step, reference can be made to the steps for synthesizing compounds BB-3-1 to BB-3, so as to obtain compound 0028-1. MS (ESI) m/z: 603.0 [M+H]⁺.

Step 2: Synthesis of Compound 0028

Compound 0028-1 (43 mg) is dissolved in a solution of hydrochloride in ethyl acetate (2.0 mL, 4 M), and stirred at 25° C. for 2 hours. After the reaction, the reaction solution is directly subjected to rotary evaporation to dryness. The obtained crude product is separated and purified by high-performance liquid chromatography (column: Waters Xbridge 150*25 mm 5 μm; mobile phase: [water (0.05% ammonia hydroxide v/v)-ACN]; B %: 41%-71%, 7 minutes) to obtain compound 0028. MS (ESI) m/z: 503.2 [M+H]⁺.

¹H NMR (400 MHz, CHCl₃) δ: 8.45 (s, 1H) 8.16 (s, 1H) 7.76 (s, 1H) 7.49 (d, 2H) 6.60-6.62 (t, 1H) 4.21 (m, 1H) 3.87 (s, 6H) 3.78 (s, 3H) 3.27 (m, 2H) 2.78 (m, 2H) 2.54 (s, 3H) 2.21 (m, 2H) 1.87-2.00 (m, 2H).

Example 18: 0016

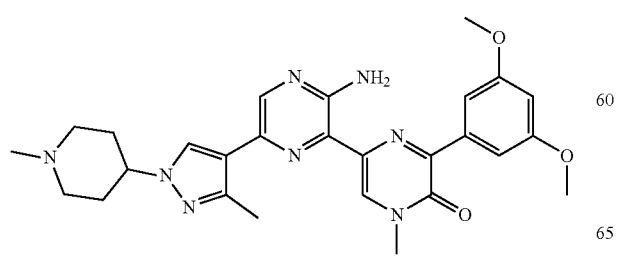

0016

54

-continued

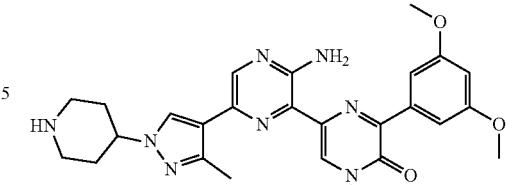

0028

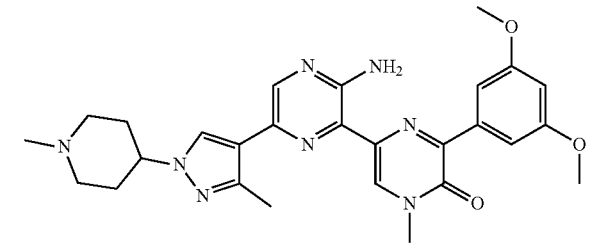

0016

Step 1: Synthesis of Compound 0016

Compound 0028 (100 mg, 162.18 μmol, 1 eq, TFA) is added to dichloromethane (2.0 mL) and methanol (2.0 mL), and then aqueous formaldehyde solution (131 mg, 1.62 mmol, 120.75 μL, 37% purity, 10 eq), sodium borohydride acetate (51 mg, 810.91 μmol, 5 eq) and sodium sulfate (46 mg, 324.36 μmol, 32.91 μL, 2 eq) are added. The reaction solution is reacted at 20° C. for 1 hour. The reaction solution is filtered, and the filtrate is concentrated to obtain a crude product. The crude product is separated and purified by high-performance liquid chromatography (column: Boston Green ODS 150*30 mm 5 μm; mobile phase: [water (0.1% TFA)-ACN]; B %: 27% to 45.75%, 7 minutes) to obtain the trifluoroacetate salt of compound 0016. The salt is dissolved in ethyl acetate, washed with saturated sodium bicarbonate, dried over anhydrous sodium sulfate and filtered, and the filtrate is concentrated to obtain compound 0016.

Trifluoroacetate salt of compound 0016: MS (ESI) m/z: 517.0 [M+H]⁺.

¹H NMR (400 MHz, MeOH) δ: 8.66 (s, 1H) 8.18 (s, 1H), 8.14 (s, 1H) 7.47 (d, 2H) 6.65 (t, 1H), 4.47-4.50 (m, 1H), 3.87 (s, 6H) 3.80 (s, 3H), 3.61-3.64 (m, 2H), 3.20-3.24 (m, 2H), 2.92 (s, 3H), 2.57 (s, 3H), 2.36-2.37 (m, 4H).

Example 19: 0031

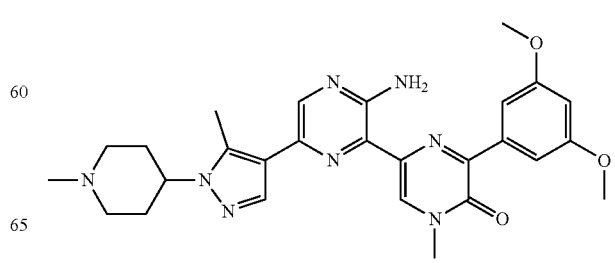

0031

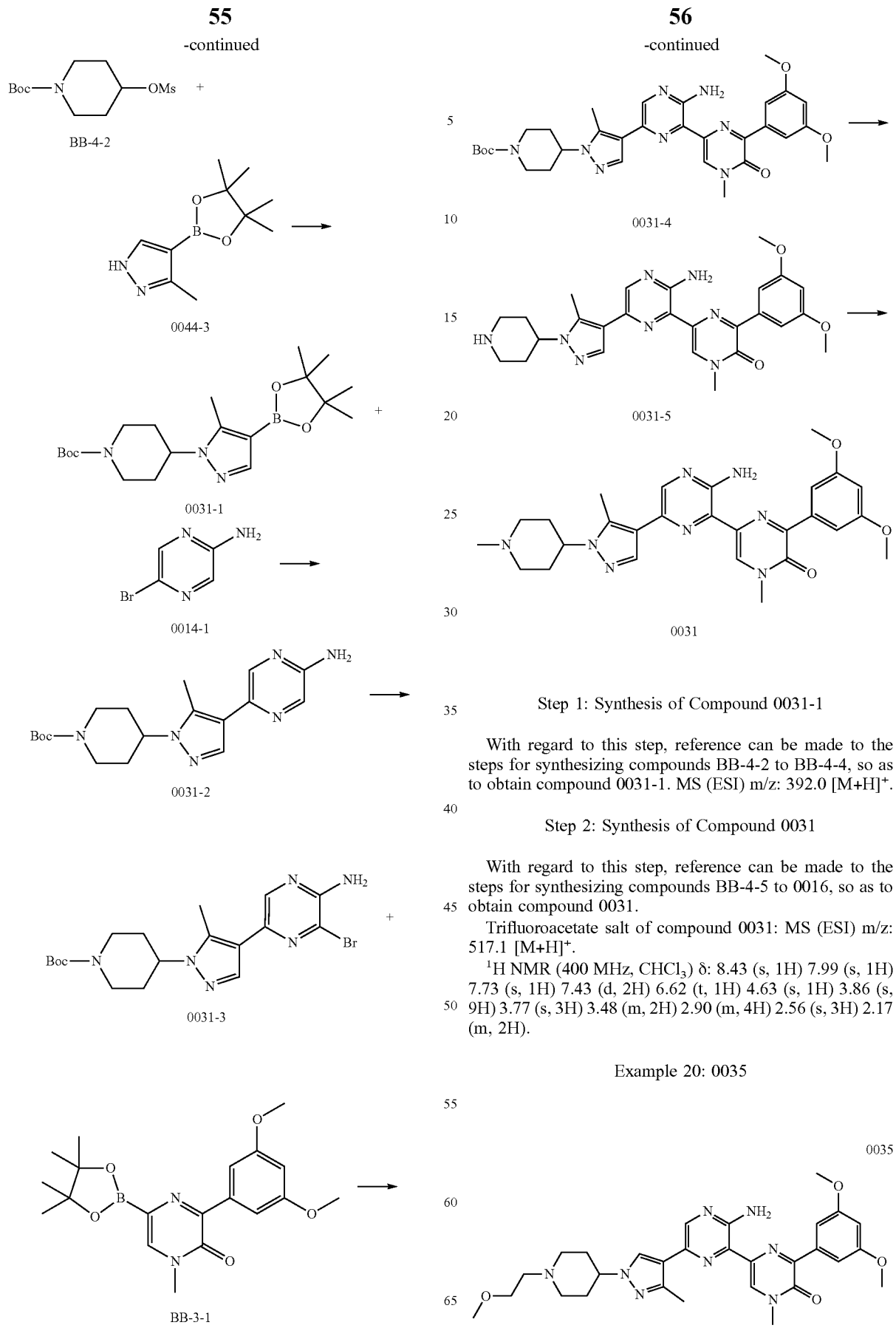

Step 1: Synthesis of Compound 0031-1

With regard to this step, reference can be made to the steps for synthesizing compounds BB-4-2 to BB-4-4, so as to obtain compound 0031-1. MS (ESI) m/z: 392.0 [M+H]$^+$.

Step 2: Synthesis of Compound 0031

With regard to this step, reference can be made to the steps for synthesizing compounds BB-4-5 to 0016, so as to obtain compound 0031.

Trifluoroacetate salt of compound 0031: MS (ESI) m/z: 517.1 [M+H]$^+$.

$^1$H NMR (400 MHz, CHCl$_3$) δ: 8.43 (s, 1H) 7.99 (s, 1H) 7.73 (s, 1H) 7.43 (d, 2H) 6.62 (t, 1H) 4.63 (s, 1H) 3.86 (s, 9H) 3.77 (s, 3H) 3.48 (m, 2H) 2.90 (m, 4H) 2.56 (s, 3H) 2.17 (m, 2H).

Example 20: 0035

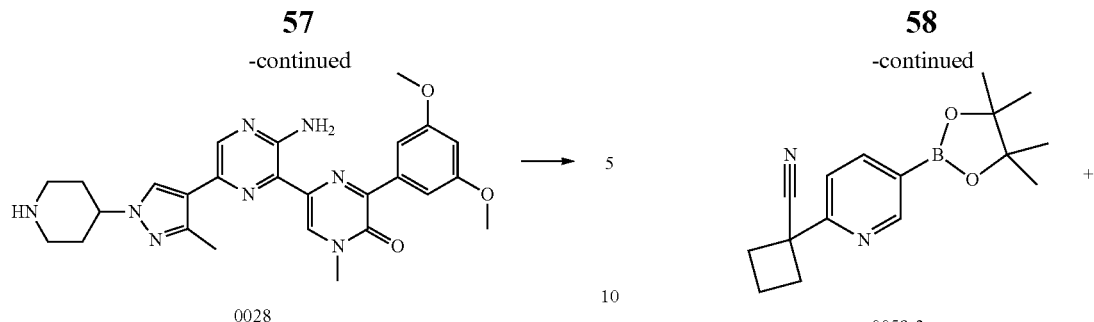

0028

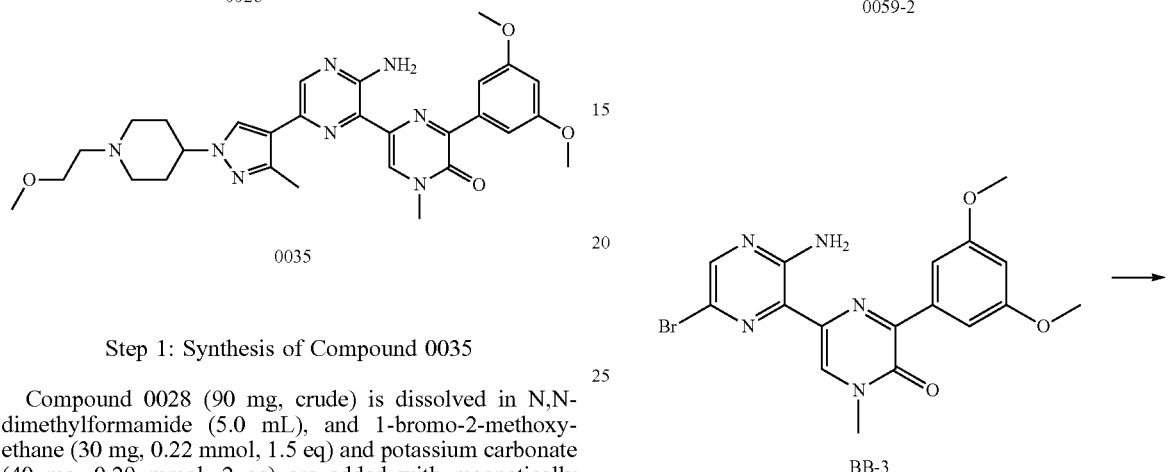

0035

Step 1: Synthesis of Compound 0035

Compound 0028 (90 mg, crude) is dissolved in N,N-dimethylformamide (5.0 mL), and 1-bromo-2-methoxy-ethane (30 mg, 0.22 mmol, 1.5 eq) and potassium carbonate (40 mg, 0.29 mmol, 2 eq) are added with magnetically stirring and reacted at 25° C. for 16 hours. After the reaction, the reaction solution is extracted with ethyl acetate (30.0 mL, 30.0 mL, 30.0 mL) three times. The organic phases are combined, and washed with water (30.0 mL, 30.0 mL, 30.0 mL) three times; finally, the organic phase is dried over anhydrous sodium sulfate, filtered and concentrated under reduced pressure. The obtained crude product is separated and purified by high-performance liquid chromatography to obtain compound 0035. MS (ESI) m/z: 561.2 [M+H]+.

$^1$H NMR (400 MHz, CHCl$_3$) δ: 8.61 (s, 1H) 8.03 (s, 1H) 7.89 (s, 1H) 7.39 (d, 2H) 6.59 (t, 1H) 4.43 (m, 1H) 3.74-3.87 (m, 12H) 3.54-3.69 (m, 1H) 3.36-3.40 (m, 3H) 3.28 (m, 2H) 2.96 (m, 2H) 2.65 (m, 2H) 2.46 (s, 3H) 2.40 (m, 2H).

Example 21: 0059

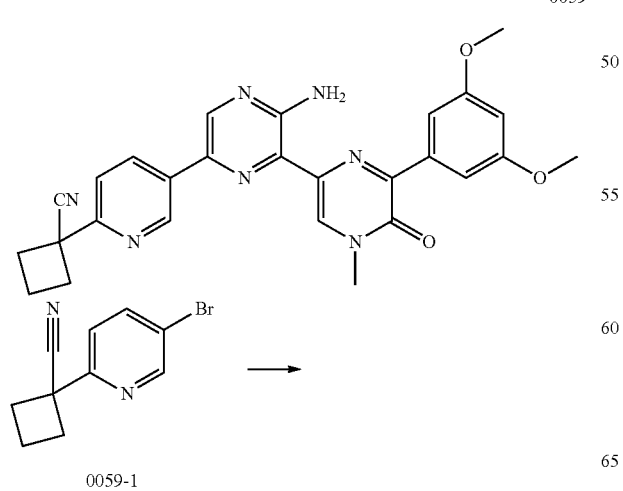

0059

0059-1

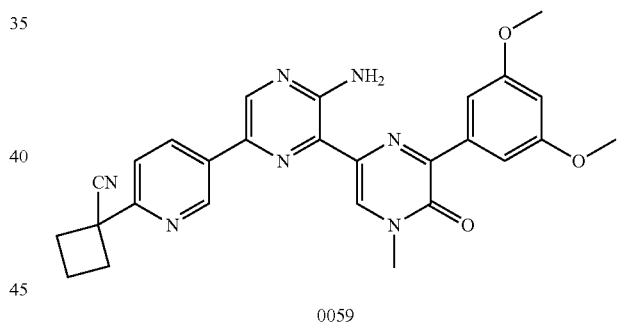

0059-2

BB-3

0059

Step 1: Synthesis of Compound 0059-2

With regard to this step, reference can be made to the steps for synthesizing compounds BB-4-4 to BB-4-5, and the reaction is performed for 16 hours so as to obtain compound 0059-2.

MS (ESI) m/z: 202.9 [M+H]+.

Step 2: Synthesis of Compound 0059

With regard to this step, reference can be made to the steps for synthesizing compounds BB-1 to 0023, so as to obtain compound 0059. MS (ESI) m/z: 496.1 [M+H]+.

$^1$H NMR (400 MHz, DMSO-d$_6$) δ: 9.43 (d, 1H), 8.98 (s, 1H), 8.71 (s, 1H), 8.56 (n, 1H), 7.65 (d, 1H), 7.45 (d, 2H), 6.65 (t, 1H), 3.81 (s, 6H), 3.76 (s, 3H), 2.89-2.66 (m, 4H) 2.35-2.26 (m, 1H), 2.15-2.05 (m, 1H).

Examples 22, 23, 24 and 25: 0062, 0063, 0064 and 0065
0062 or 0063
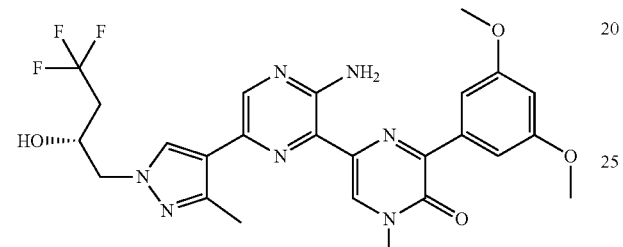
0063 or 0062
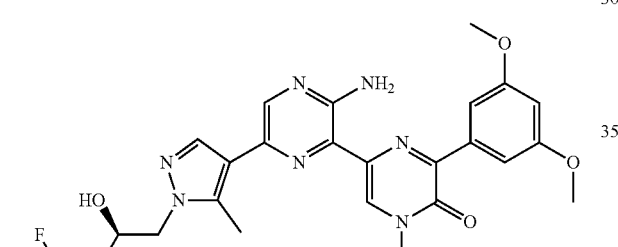
0064 or 0065
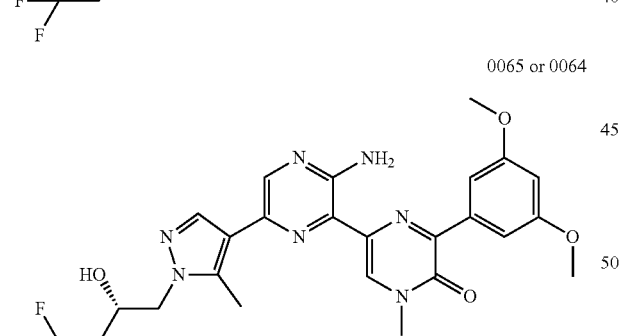
0065 or 0064
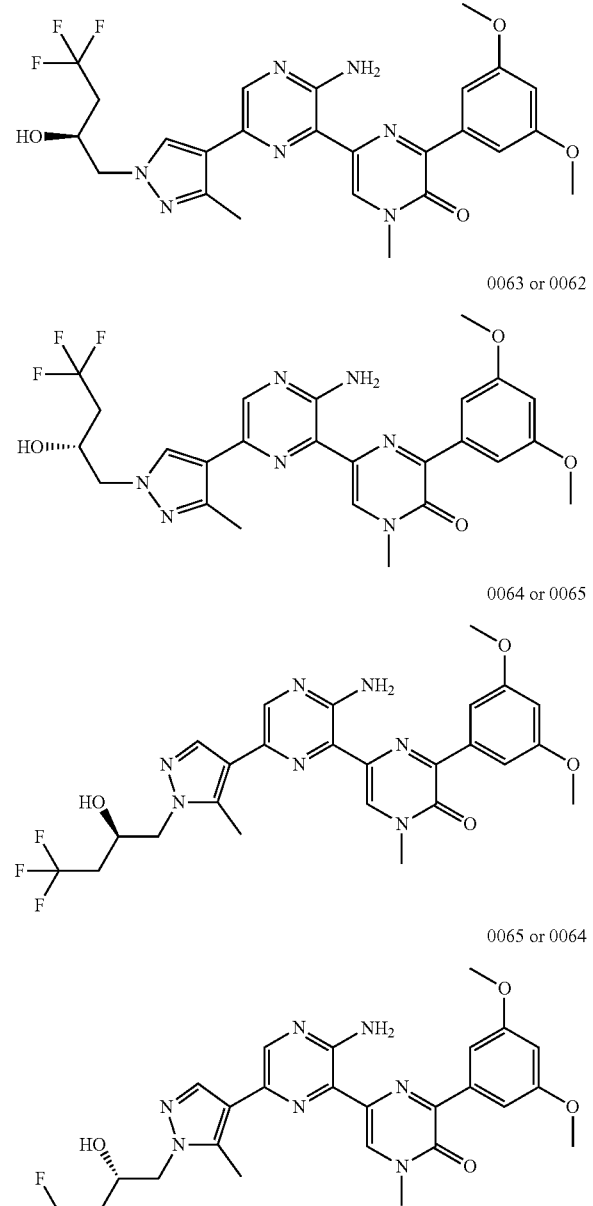
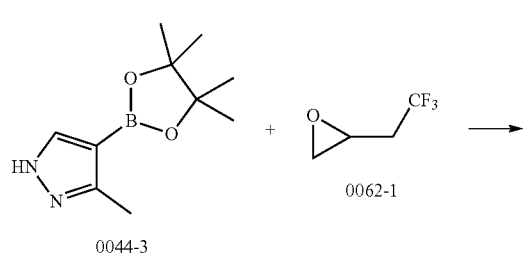
0044-3     0062-1
-continued
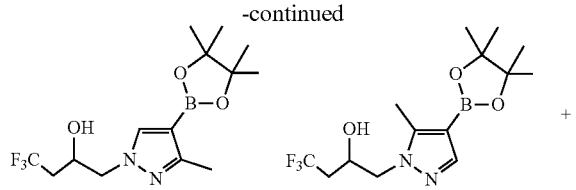
0062-2     0062-3
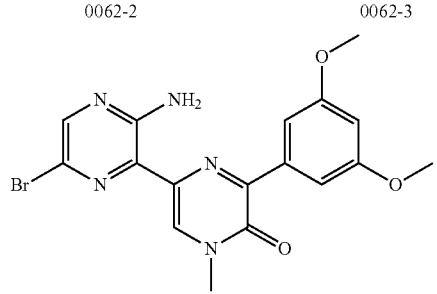
BB-3
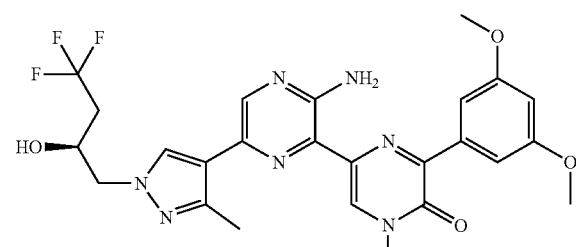
0062 or 0063
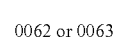
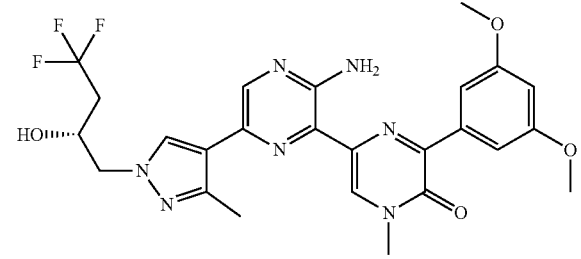
0063 or 0062
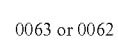
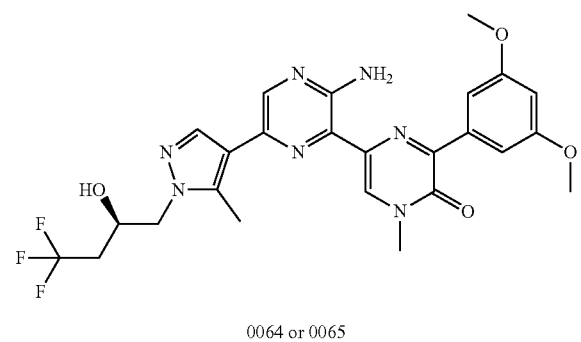
0064 or 0065

-continued

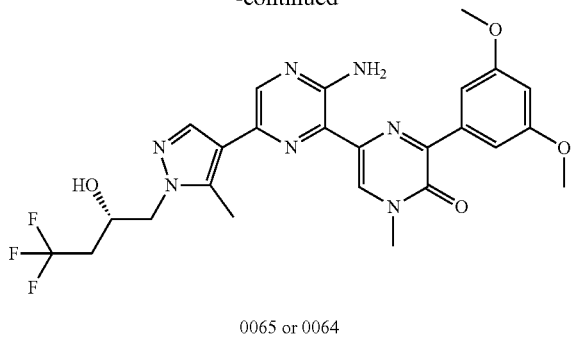

0065 or 0064

Step 1: Synthesis of Compounds 0062-2 and 0062-3

Compound 0044-3 (2.0 g, 9.61 mmol, 1 eq), compound 0062-1 (1.5 g, 11.53 mmol, 1.2 eq) and cesium carbonate (9.4 g, 28.84 mmol, 3 eq) are dissolved in isopropanol (60.0 mL), and are reacted at 86° C. for 8 hours. The reaction solution is subjected to suction filtration and concentrated to obtain the product. The product is separated and purified by column chromatography (petroleum ether:ethyl acetate=1:0 to 1:1) to obtain a mixture of compounds 0062-2 and 0062-3.

Step 2: Synthesis of Compounds 0062, 0063, 0064 and 0065

Compound BB-3 (120 mg, 286.91 μmol, 1 eq), tetratriphenyphosphine palladium (66 mg, 57.38 μmol, 0.2 eq), potassium phosphate (183 mg, 860.74 μmol, 3 eq), and a mixture of compounds 0062-2 and 0062-3 (192 mg 573.83 μmol, 2 eq) are dissolved in dioxane (20.0 mL), and reacted at 100° C. for 8 hours under nitrogen protection. Water (3.0 mL) is added, there being a solid precipitated, and a mixture product is obtained by suction filtration. The mixture product is subjected to chiral resolution (column: YMC CHIRAL Amylose-C (250 mm×30 mm, 10 μm; mobile phase: [0.1% NH$_3$.H$_2$O IPA]; B %: 55% to 55%, minutes) to obtain compounds 0062 (retention time: 1.697 minutes), 0063 (retention time: 2.59 minutes), 0064 (retention time: 2.881 minutes), and 0065 (retention time: 4.411 minutes). MS (ESI) m/z: 546.0 [M+H]$^+$.

0062: $^1$H NMR (400 MHz, DMSO-d$_6$) δ: 8.55-8.48 (m, 1H), 8.12-8.02 (m, 1H), 8.00-7.88 (m, 1H), 7.37-7.29 (m, 2H), 6.57-6.48 (m, 1H), 4.23 (br s, 1H), 4.11-4.04 (m, 1H), 4.12-3.95 (m, 1H), 3.74 (s, 6H), 3.66 (s, 3H), 2.43 (s, 3H), 2.36-2.19 (m, 2H).

0063: $^1$H NMR (400 MHz, DMSO-d$_6$) δ: 8.55-8.48 (m, 1H), 8.12-8.02 (m, 1H), 8.00-7.88 (m, 1H), 7.37-7.29 (m, 2H), 6.57-6.48 (m, 1H), 4.23 (br s, 1H), 4.11-4.04 (m, 1H), 4.12-3.95 (m, 1H), 3.74 (s, 6H), 3.66 (s, 3H), 2.43 (s, 3H), 2.36-2.19 (m, 2H).

0064: $^1$H NMR (400 MHz, DMSO-d$_6$) δ: 8.28 (s, 1H), 7.96-7.87 (m, 1H), 7.76-7.67 (m, 1H), 7.25 (d, 2H), 6.47-6.32 (m, 1H), 4.32-4.20 (m, 1H), 4.05 (d, 2H), 3.69 (s, 6H), 3.56 (s, 3H), 2.46 (s, 3H), 2.40-2.20 (m, 2H).

0065: $^1$H NMR (400 MHz, DMSO-d$_6$) δ: 8.28 (s, 1H), 7.96-7.87 (m, 1H), 7.76-7.67 (m, 1H), 7.25 (d, 2H), 6.47-6.32 (m, 1H), 4.32-4.20 (m, 1H), 4.05 (d, 2H), 3.69 (s, 6H), 3.56 (s, 3H), 2.46 (s, 3H), 2.40-2.20 (m, 2H).

Experimental Example 1: Evaluation of In-Vitro Inhibitory Activity of Wild-Type Kinase The IC$_{50}$ value is determined using $^{33}$P isotope-labeled kinase activity test (Reaction Biology Corp) to evaluate the inhibitory ability of the compounds to be tested on human FGFR1 and FGFR4.

Buffer conditions: 20 mM 4-(2-hydroxyethyl)-1-piperazineethanesulfonic acid (Hepes) (pH 7.5), 10 mM MgCl$_2$, 1 mM ethylene glycol-bis-(2-aminoethyl ether)tetraacetic acid (EGTA), 0.02% polyoxyethylene lauryl ether (Brij35), 0.02 mg/ml bovine serum albumin (BSA), 0.1 mM sodium vanadate (Na$_3$VO$_4$), 2 mM dithiothreitol (DTT), and 1% DMSO.

Test steps: At room temperature, the compounds to be tested are dissolved in DMSO to prepare a 10 mM solution for use. The substrate is dissolved in the newly prepared buffer, and the kinase to be tested is added and mixed well. The DMSO solution in which the compounds to be tested are dissolved is added to the above-mentioned homogeneous reaction solution using acoustic technology (Echo 550). The concentrations of the compounds in the reaction solution are 10 μM, 3.33 μM, 1.11 μM, 0.370 μM, 0.123 μM, 41.2 nM, 13.7 nM, 4.57 nM, 1.52 nM, 0.508 nM, or 10 μM, 2.50 μM, 0.62 μM, 0.156 μM, 39.1 nM, 9.8 nM, 2.4 nM, 0.61 nM, 0.15 nM, and 0.038 nM. After incubating for 15 minutes, $^{33}$P-ATP (activity: 0.01 μCi/μl, with corresponding concentration being listed in table 1) is added to start the reaction. The supplier article number, batch number, and the concentration information in the reaction solution of FGFR1, FGFR4 and substrates thereof are listed in table 1. After the reaction is carried out at room temperature for 120 minutes, the reaction solution is spotted on P81 ion exchange filter paper (Whatman #3698-915). After the filter paper is repeatedly washed with 0.75% phosphoric acid solution, the radioactivity of the phosphorylated substrate remaining on the filter paper is measured. The kinase activity data is expressed by comparing the kinase activity of the groups containing the compounds to be tested with that of the blank group (containing only DMSO). The IC$_{50}$ value is obtained by curve fitting using Prism4 software (GraphPad), and the experimental results are shown in table 2.

TABLE 1

Related information about kinases, substrates and ATP in in-vitro tests.

| Kinase | Supplier | Cat # | Lot # | ATP concentration (μM) |
|---|---|---|---|---|
| FGFR1 | Invitrogen | PV3146 | 28427Q | 5 |
| FGFR2 | Invitrogen | PV3368 | 31517I | 5 |
| FGFR3 | Invitrogen | PV3145 | 28459R | 30 |
| FGFR4 | Invitrogen | P3054 | 26967J | 2.5 |

TABLE 1-continued

Related information about kinases, substrates and ATP in in-vitro tests.

| Substrate | Supplier | Cat # | Lot # | Substrate concentration in reaction solution (μM) |
|---|---|---|---|---|
| pEY (mg/ml) + Mn | Sigma | P7244-250MG | 062K5104V | 0.2 |
| pEY (mg/ml) + Mn | Sigma | P7244-250MG | 062K5104V | 0.2 |
| pEY (mg/ml) + Mn | Sigma | P7244-250MG | 062K5104V | 0.2 |
| pEY (mg/ml) + Mn | Sigma | P7244-250MG | 062K5104V | 0.2 |

TABLE 2

Results of in-vitro screening tests of compounds of the present invention

| Compound | IC$_{50}$ (nM) | | | | Selectivity | |
|---|---|---|---|---|---|---|
| | FGFR1 | FGFR2 | FGFR3 | FGFR4 | FGFR1/2 | FGFR1/3 |
| Trifluoroacetate salt of 0018 | 726.90 | 15.06 | 8.11 | / | 48.27 | 89.67 |
| 0017 | 78.74 | 8.79 | 6.31 | / | 8.95 | 12.48 |
| Hydrochloride salt of 0023 | 164.10 | 32.13 | 29.75 | / | 5.11 | 5.52 |
| Trifluoroacetate salt of 0027 | 2.12 | 0.53 | 0.69 | 106 | 4.02 | 3.06 |
| 0028 | 53.98 | 7.66 | 10.54 | / | 7.05 | 5.12 |
| Trifluoroacetate salt of 0029 | 2.33 | 0.56 | 1.54 | / | 4.14 | 1.52 |
| Trifluoroacetate salt of 0016 | 29.21 | 4.21 | 4.93 | 8638 | 6.94 | 5.92 |
| 0038 | >10000 | 146.20 | 10.22 | / | >68.4 | >978.5 |
| Hydrochloride salt of 0036 | 13.19 | 2.48 | 1.81 | >10000 | 5.31 | 7.28 |
| 0040 | >10000 | 801.50 | 55.57 | / | >12.5 | >179.95 |
| 0035 | 29.28 | 5.83 | 5.04 | / | 5.02 | 5.81 |
| Trifluoroacetate salt of 0031 | 182.70 | 43.99 | 27.80 | / | 4.15 | 6.57 |
| Hydrochloride salt of 0033 | 2281.00 | 313.60 | 119.10 | / | 7.27 | 19.15 |
| 0046 | 40.65 | 6.78 | 4.48 | 5820 | 6.00 | 9.08 |
| 0045 | 226.10 | 29.80 | 17.44 | / | 7.59 | 12.96 |
| 0048 | 268.80 | 56.11 | 57.76 | / | 4.79 | 4.65 |
| 0043 | 53.01 | 12.71 | 7.99 | / | 4.17 | 6.63 |
| 0049 | 200.90 | 65.50 | 34.34 | / | 3.07 | 5.85 |
| 0051 | 29.28 | 6.54 | 4.11 | / | 4.48 | 7.12 |
| 0056 | 126.40 | 11.90 | 10.75 | / | 10.62 | 11.76 |
| 0059 | >10000 | 3058.00 | 49.40 | / | / | / |
| Trifluoroacetate salt of 0060 | 3.081 | 0.5333 | 0.9443 | / | 5.78 | 3.26 |
| 0062 | 61.56 | 11.25 | 7.327 | / | 5.47 | 8.40 |
| 0063 | 70.81 | 16.13 | 12.25 | / | 4.39 | 5.78 |
| 0064 | 180.7 | 22.68 | 16.17 | / | 7.97 | 11.18 |
| 0065 | 407.3 | 53.89 | 45.23 | / | 7.56 | 9.01 |

Conclusion: The compounds of the present invention exhibit good inhibitory activity against all wild-type FGFR, and show a higher selectivity on FGFR2 and 3 than FGFR1 and 4.

Experimental Example 2: Pharmacokinetic Evaluation of Compounds

Experimental purpose: testing pharmacokinetics of the compounds in mice

Experimental Materials:

CD-1 mouse (male), vehicle (an aqueous solution of 0.5% (w/v) methylcellulose and 0.5% (v/v) Tween 80), and trfluoroacetate salt of compound 0027.

Formulation of Preparations for Administration the vehicle is an aqueous solution of 0.5% (w/v) methylcellulose and 0.5% (v/v) Tween 80, and is formulated according to the following procedures:

adding approximately 50% volume of purified water to a suitable container and heating to approximately 60° C. to 70° C.;

turning off the heater when the water temperature reaches the specified value range, slowly adding the required amount of methylcellulose into the above-mentioned container, and stirring same continuously;

continue stirring at 4° C. until a clear solution is obtained visually;

adding the required volume of Tween 80 to the above-mentioned solution, and continue stirring until Tween 80 being evenly dispersed and a clear solution are obtained visually;

making up the above-mentioned solution to the final volume with appropriate amount of purified water; and continue stirring until a homogeneous solution is formed.

Formulation of preparations for intragastric administration:

weighing an appropriate amount of a sample to be test into a glass bottle;

adding 70% volume of the vehicle (an aqueous solution of 0.5% (w/v) methylcellulose and 0.5% (v/v) Tween 80);

stirring same until being visually homogeneous, and performing ultrasound in a water bath as needed; and making up the remaining volume of 0.5% methylcellulose+0.5% Tween 80, and stirring same until being visually homogeneous.

Administration

The animals in groups 1 and 2 are administrated 5 mg/mL and 30 mg/mL of the compounds by single gavage, respectively, and the administration volume is 10 mL/kg.

The body weight of the animals is weighed before administration, and the administration volume is calculated based on the bodyweight.

Sample Collection and Processing

Whole blood samples (30 μl) are collected at the prescribed time points (0.25, 0.5, 1, 2, 4, 6, 8, 24 h) by saphenous vein blood collection, and the actual blood collection time is recorded in the test record. The acceptable error of the collection time point is a time point within 1 hour of administration time ±1 minute, and the acceptable error of other time points is a theoretical time ±5%.

All blood samples are immediately transferred to labeled commercial centrifuge tubes containing K2-EDTA. After being collected, the blood samples are centrifuged at 3200 rpm/min for 10 minutes at 4° C. to aspirate the supernatant plasma, which is quickly placed in dry ice, and kept at −20° C. or a lower temperature for LC-MS/MS analysis. The pharmacokinetic parameters are calculated, and the experimental results are shown in table 3:

Experimental results: See table 3.

TABLE 3

Pharmacokinetic test results

| Parameter | Compound Trifluoroacetate salt of compound 0027 Dose | |
|---|---|---|
| | 50 mpk | 300 mpk |
| $C_{max}$ (nM) | 14800 | 42100 |
| $T_{max}$ (hr) | 1.00 | 7.00 |
| $T_{1/2}$ (hr) | 2.46 | ND |
| $T_{last}$ (hr) | ND | 24.0 |
| $AUC_{0-last}$ (nM · hr) | 85826 | 699413 |
| $AUC_{0-inf}$ (nM · hr) | 95847 | ND |
| $MRT_{0-last}$ (h) | 4.33 | 11.1 |
| $MRT_{0-inf}$ (h) | 5.39 | ND |

ND represents: not determined

Conclusion: The compounds of the present invention have good pharmacokinetic indexes in mice.

What is claimed is:

1. A compound as shown in formula (I), a tautomer or stereoisomer thereof or a pharmaceutically acceptable salt thereof, wherein

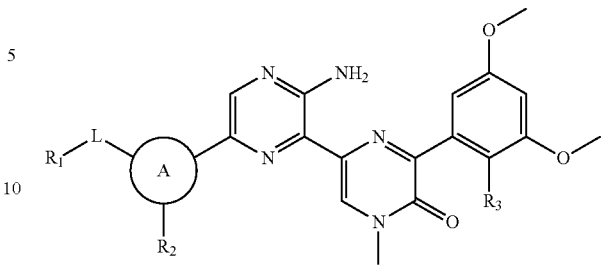

(I)

L is selected from a single bond, —CH$_2$—, —CH$_2$CH$_2$— and —NHC(=O)—;

R$_1$ is selected from H, C$_{1-6}$ alkyl, C$_{3-6}$ cycloalkyl and 5- to 6-membered heterocycloalkyl, wherein the C$_{1-6}$ alkyl, C$_{3-6}$ cycloalkyl and 5- to 6-membered heterocycloalkyl are optionally substituted with 1, 2 or 3 R$_a$;

R$_a$ is each independently selected from F, Cl, Br, I, OH, NH$_2$, CN, C$_{1-3}$ alkyl and C$_{1-3}$ heteroalkyl, wherein the C$_{1-3}$ alkyl and C$_{1-3}$ heteroalkyl are optionally substituted with 1, 2, or 3 R;

R is each independently selected from F, Cl, Br, I, OH, NH$_2$, CN, Me, CF$_3$ and

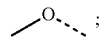

R$_2$ is selected from F, Cl, Br, I, OH, NH$_2$, CN, C$_{1-3}$ alkyl and C$_{1-3}$ heteroalkyl;

or R$_1$ and R$_2$ are connected together to form a 5- to 6-membered ring, wherein the 5- to 6-membered ring is optionally substituted with 1, 2 or 3 R;

R$_3$ is selected from H, F, Cl, Br, I, OH and NH$_2$;

ring A is selected from 5- to 6-membered heteroaryl; and the C$_{1-3}$ heteroalkyl, 5- to 6-membered heterocycloalkyl and 5- to 6-membered heteroaryl respectively comprise 1, 2 or 3 heteroatoms or heteroatomic groups independently selected from —O—, —NH—, —S— and N.

2. The compound, tautomer or stereoisomer thereof or pharmaceutically acceptable salt thereof as defined in claim 1, wherein R$_a$ is each independently selected from F, Cl, Br, I, OH, NH$_2$, CN, C$_{1-3}$ alkyl and C$_{1-3}$ alkoxy, and wherein the C$_{1-3}$ alkyl and C$_{1-3}$ alkoxy are optionally substituted with 1, 2, or 3 R.

3. The compound, tautomer or stereoisomer thereof or pharmaceutically acceptable salt thereof as defined in claim 2, wherein R$_a$ is each independently selected from F, Cl, Br, I, OH NH$_2$, CN, Me, Et and

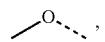

and wherein the Me, Et and

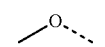

are optionally substituted with 1, 2 or 3 R.

4. The compound, tautomer or stereoisomer thereof or pharmaceutically acceptable salt thereof as defined in claim 3, wherein R$_a$ is each independently selected from F, Cl, Br, I, OH, NH$_2$, CN, Me, CF$_3$,

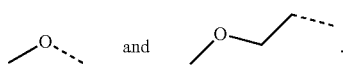 and

5. The compound, tautomer or stereoisomer thereof or pharmaceutically acceptable salt thereof as defined in claim 1, wherein $R_1$ is selected from H, $C_{1-3}$ alkyl, $C_{3-6}$ cycloalkyl, piperidinyl and morpholinyl, and wherein the $C_{1-3}$ alkyl, $C_{3-6}$ cycloalkyl, piperidinyl and morpholinyl are optionally substituted with 1, 2 or 3 $R_a$.

6. The compound, tautomer or stereoisomer thereof or pharmaceutically acceptable salt thereof as defined in claim 5, wherein $R_1$ is selected from H, Me,

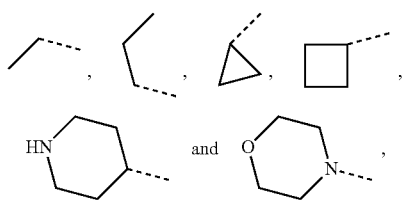

and wherein the Me,

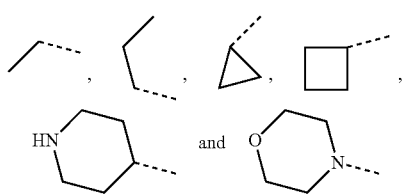

are optionally substituted with 1, 2 or 3 $R_a$.

7. The compound, tautomer or stereoisomer thereof or pharmaceutically acceptable salt thereof as defined in claim 6, wherein $R_1$ is selected from H, Me,

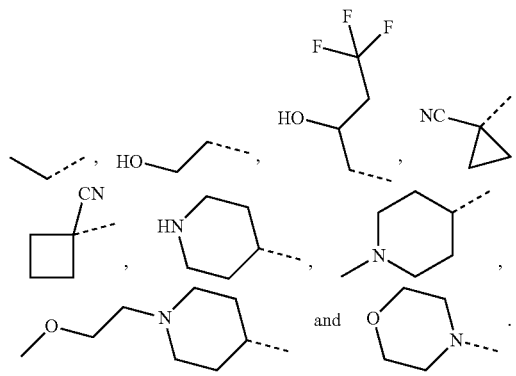

8. The compound, tautomer or stereoisomer thereof or pharmaceutically acceptable salt thereof as defined in claim 1, wherein $R_2$ is Me.

9. The compound, tautomer or stereoisomer thereof or pharmaceutically acceptable salt thereof as defined in claim 1, wherein structural unit $R_1$-L- is selected from H, Me,

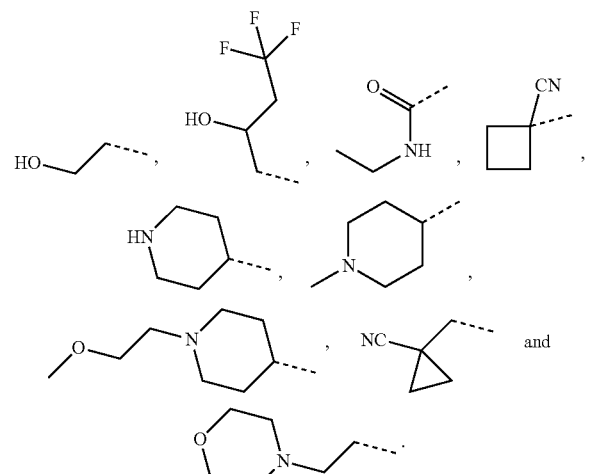

10. The compound, tautomer or stereoisomer thereof or pharmaceutically acceptable salt thereof as defined in claim 1, wherein ring A is selected from pyrazolyl, imidazolyl and pyridyl.

11. The compound, tautomer or stereoisomer thereof or pharmaceutically acceptable salt thereof as defined in claim 10, wherein structural unit

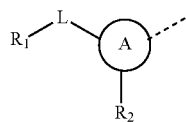

is selected from

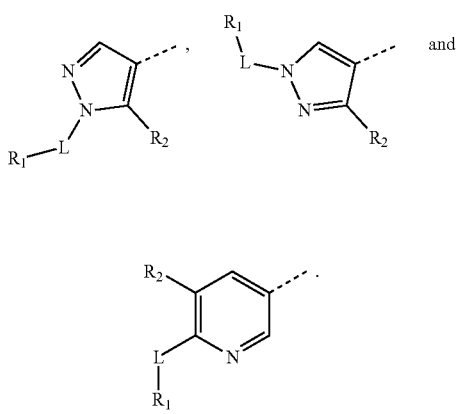

12. The compound, tautomer or stereoisomer thereof or pharmaceutically acceptable salt thereof as defined in claim 1, wherein $R_1$ and $R_2$ are connected together to form pyrrolidin-2-one, and wherein the pyrrolidine-2-one is optionally substituted with 1, 2 or 3 R.

13. The compound, tautomer or stereoisomer thereof or pharmaceutically acceptable salt thereof as defined in claim 12, wherein $R_1$ and $R_2$ are connected together, and structural unit

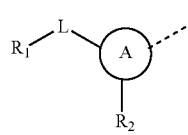
is selected from
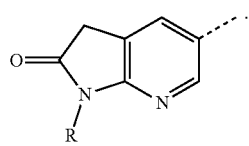
14. The compound, tautomer or stereoisomer thereof or pharmaceutically acceptable salt thereof as defined in claim 1, wherein structural unit
is selected from
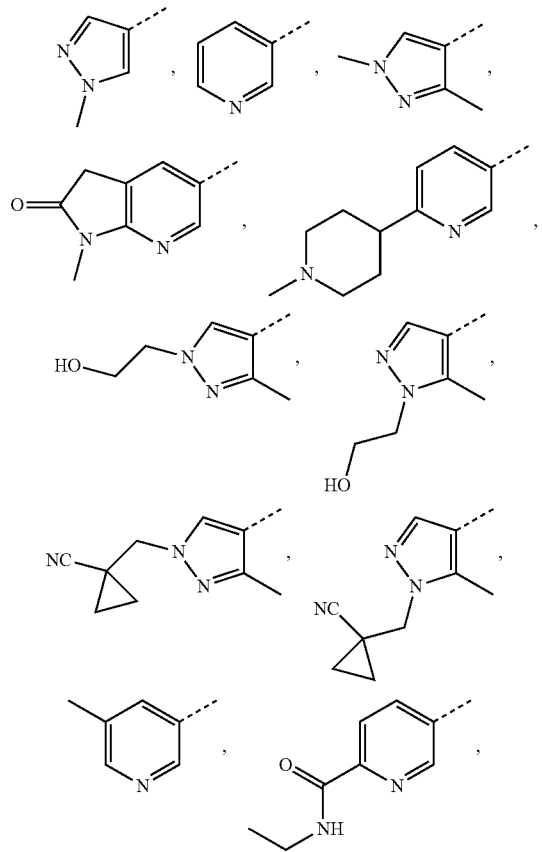
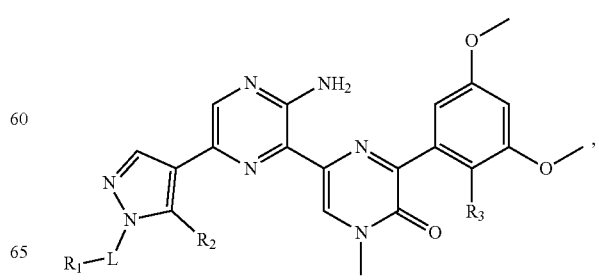
15. The compound, tautomer or stereoisomer thereof or pharmaceutically acceptable salt thereof as defined in claim 1, wherein the compound is selected from -continued
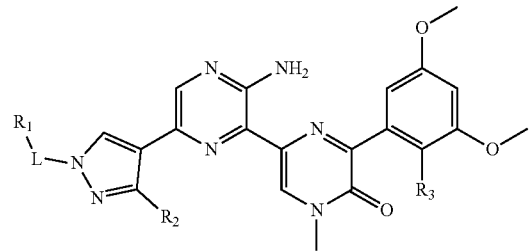
(I-2)
and
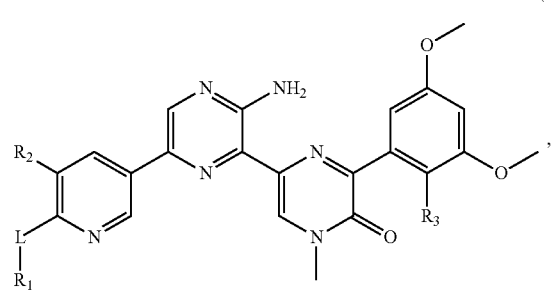
(I-4)
wherein
R₁, R₂, R₃ and L are as defined in claim 1.
16. A compound, a tautomer or stereoisomer thereof or a pharmaceutically acceptable salt thereof, wherein the compound is selected from:
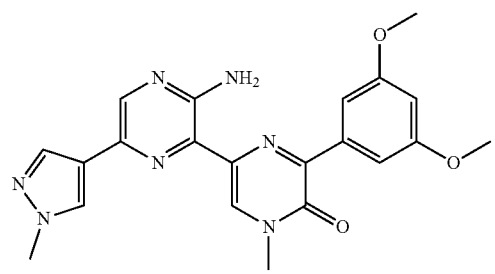
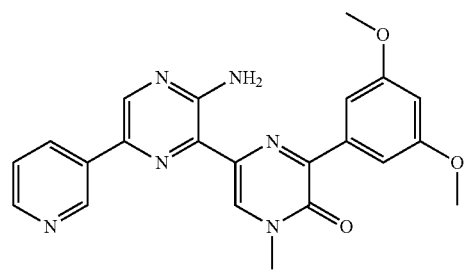
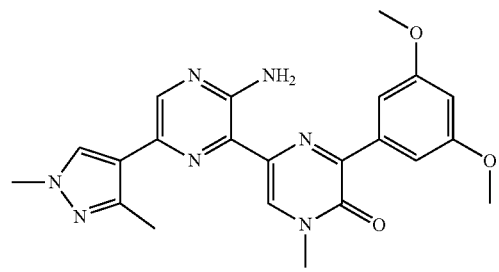
-continued
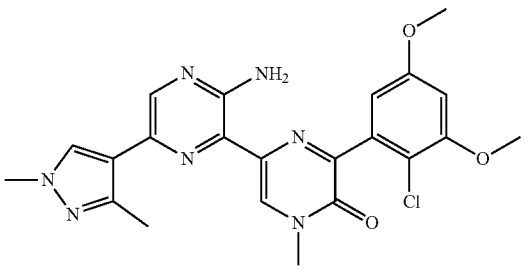
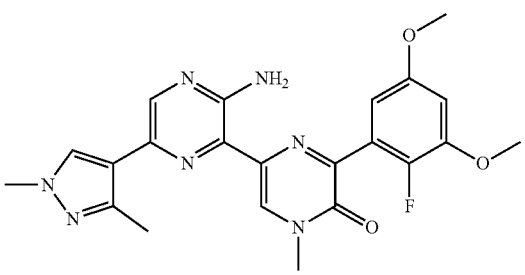
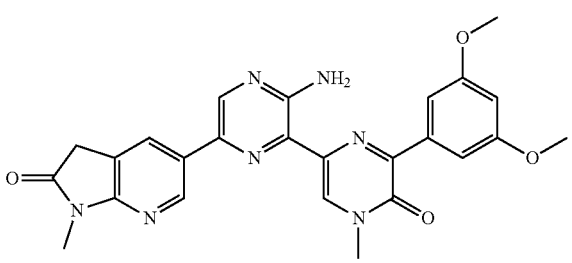
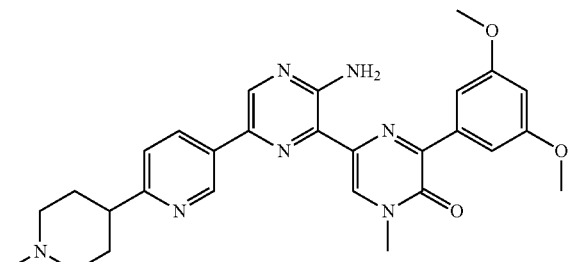
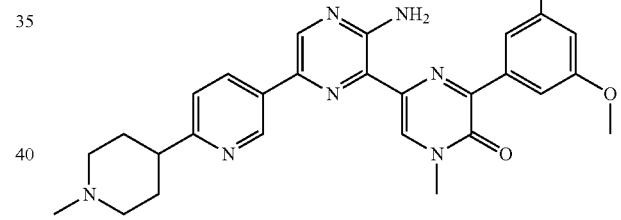
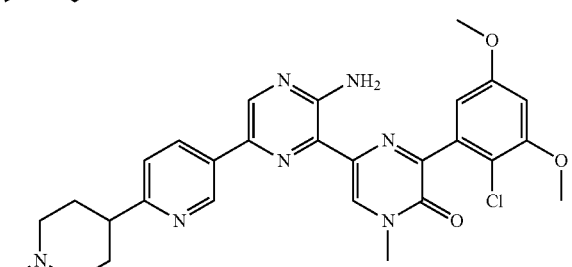
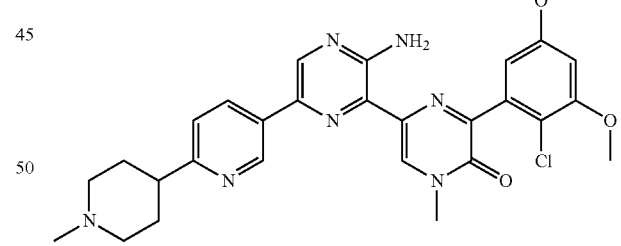
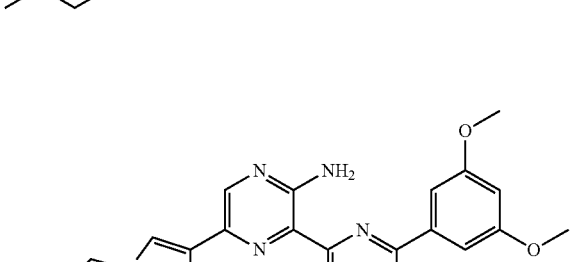
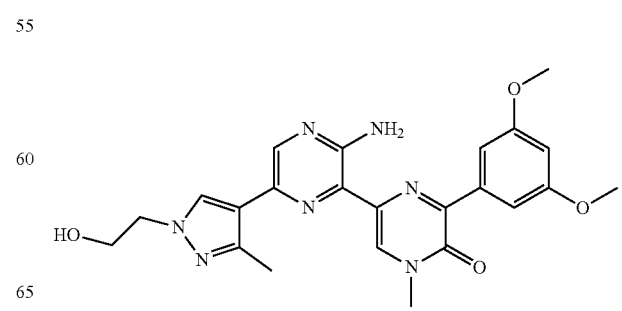

73
-continued
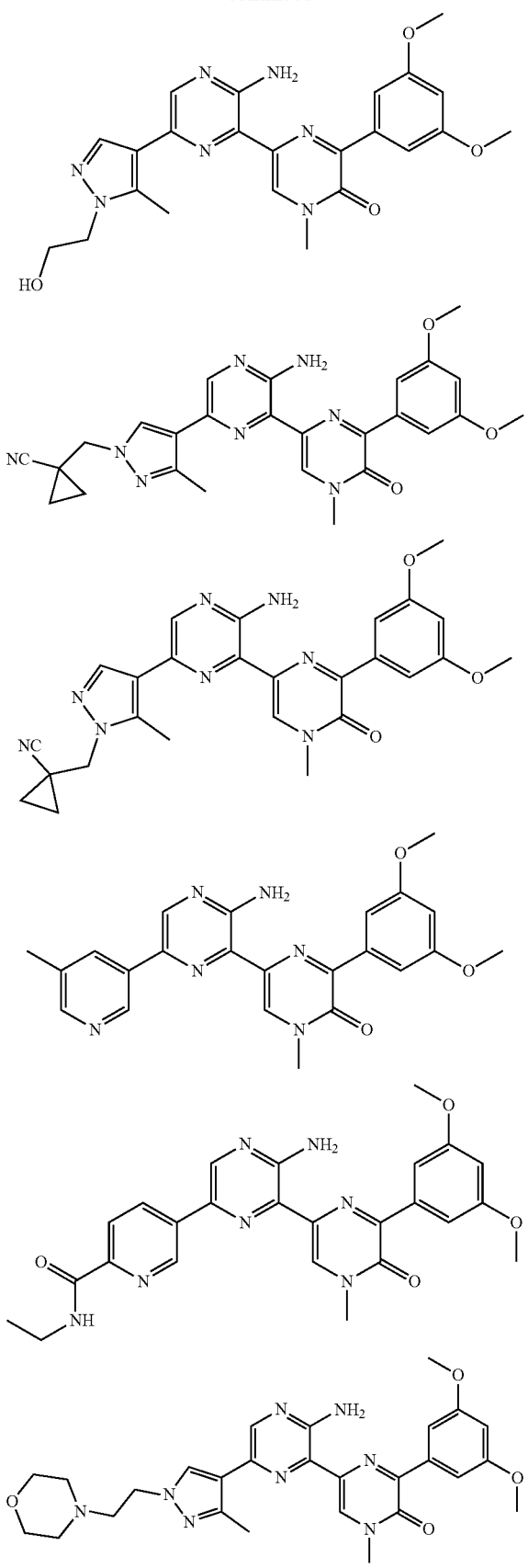
74
-continued
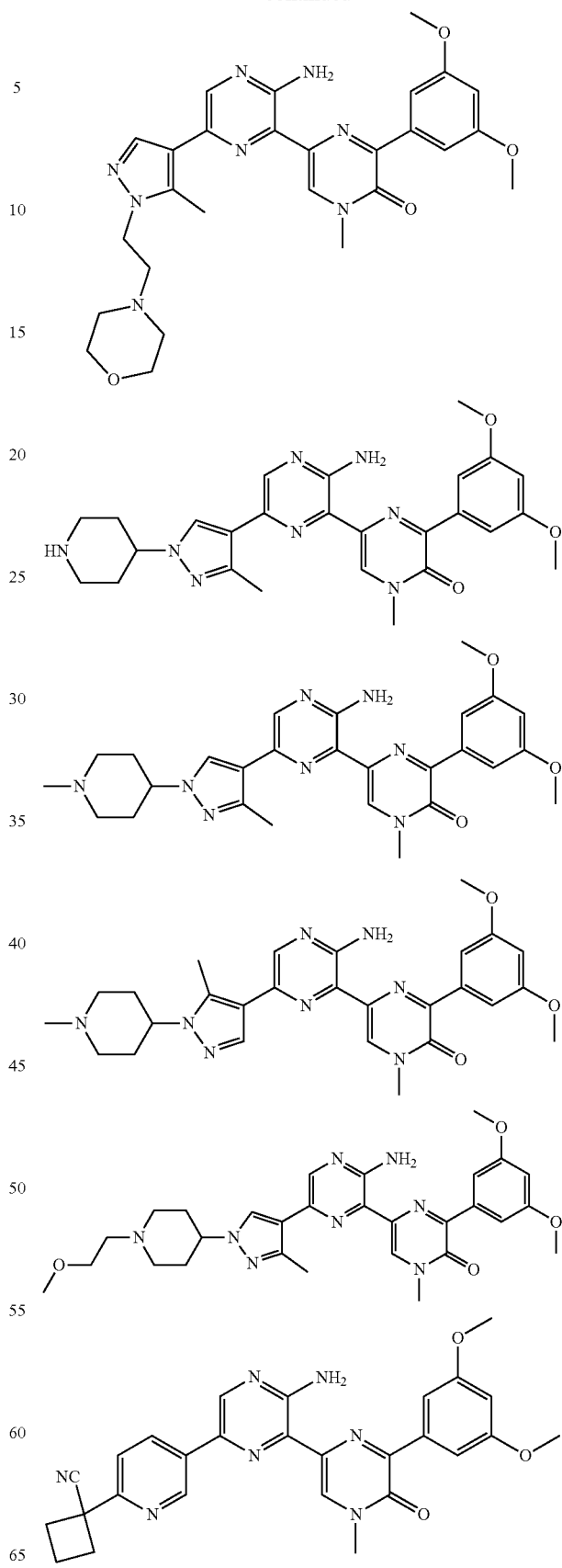

-continued

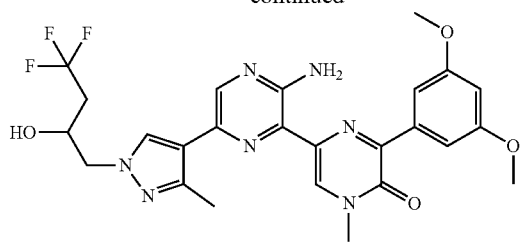

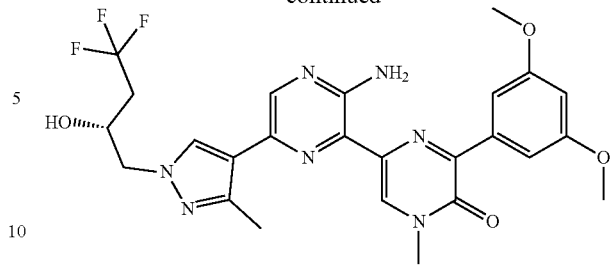

and

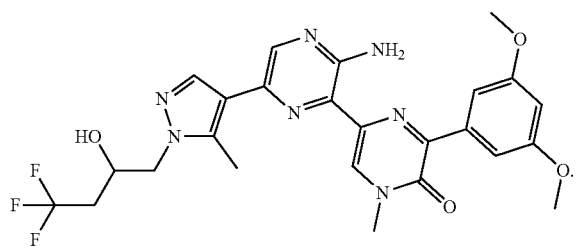

17. The compound, tautomer or stereoisomer thereof or pharmaceutically acceptable salt thereof as defined in claim 16, wherein the compound is selected from

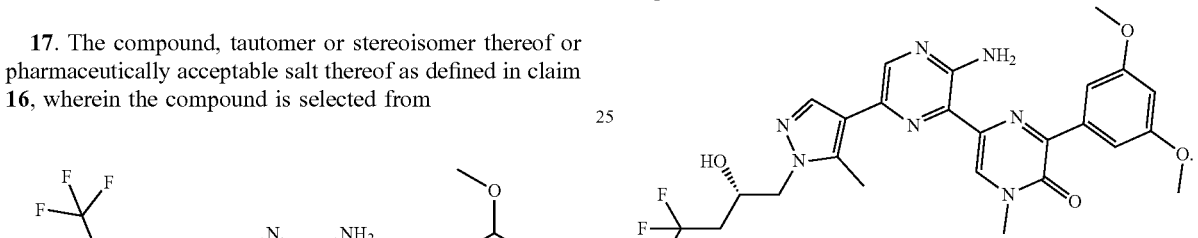

and

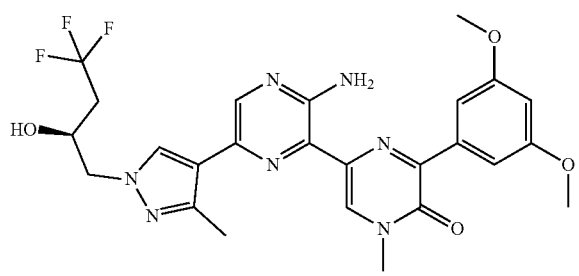

18. A method for inhibiting fibroblast growth factor receptor in a subject in need thereof, comprising administering a therapeutically effective amount of the compound, the tautomer or stereoisomer or the pharmaceutically acceptable salt thereof according to claim 1 to the subject.

* * * * *